US012611226B2

(12) United States Patent
Tori et al.

(10) Patent No.: US 12,611,226 B2
(45) Date of Patent: Apr. 28, 2026

(54) LAPAROSCOPIC TISSUE CONTAINMENT DEVICE

(71) Applicant: Ark Surgical Ltd., Nazareth (IL)

(72) Inventors: Stav Tori, RaAnana (IL); Abraham J. Yaari, Zikhron-Yaakov (IL)

(73) Assignee: Ark Surgical Ltd., Nazareth (IL)

( * ) Notice: Subject to any disclaimer, the term of this patent is extended or adjusted under 35 U.S.C. 154(b) by 154 days.

(21) Appl. No.: 18/267,481

(22) PCT Filed: Dec. 16, 2021

(86) PCT No.: PCT/IL2021/051499
§ 371 (c)(1),
(2) Date: Jun. 15, 2023

(87) PCT Pub. No.: WO2022/130385
PCT Pub. Date: Jun. 23, 2022

(65) Prior Publication Data
US 2024/0050123 A1 Feb. 15, 2024

Related U.S. Application Data

(60) Provisional application No. 63/126,640, filed on Dec. 17, 2020.

(51) Int. Cl.
*A61B 17/34* (2006.01)
*A61B 17/00* (2006.01)

(52) U.S. Cl.
CPC .... *A61B 17/3439* (2013.01); *A61B 17/00234* (2013.01); *A61B 2017/00287* (2013.01)

(58) Field of Classification Search
CPC ............ A61B 17/3439; A61B 17/3423; A61B 17/3431; A61B 17/02; A61B 2017/0225;
(Continued)

(56) References Cited

U.S. PATENT DOCUMENTS

| | | | |
|---|---|---|---|
| 3,634,938 A | 1/1972 | Hutchinson | |
| 4,447,227 A | 5/1984 | Kotsanis | |
| | (Continued) | | |

FOREIGN PATENT DOCUMENTS

| | | |
|---|---|---|
| AU | 2012202287 | 5/2012 |
| CN | 1939224 | 4/2007 |
| | (Continued) | |

OTHER PUBLICATIONS

International Preliminary Report on Patentability Dated Jun. 29, 2023 From the International Bureau of WIPO Re. Application No. PCT/IL2021/051499 (15 Pages).

(Continued)

*Primary Examiner* — Eduardo C Robert
*Assistant Examiner* — Tara Rose E Carter

(57) ABSTRACT

A workspace device having a body which is collapsible to a collapsed state to fit through a laparoscopic passageway in a body cavity wall, and expandable to an expanded state within a body cavity into which the passageway extends, including:
a workspace body having a workspace wall including a plurality of expandable segments defining an internal lumen, and a plurality of radial rigidizers positioned within the wall;
wherein in the expanded state:
the workspace device extends defining a workspace axis, and has an opening to the internal volume; and
the plurality of expandable segments rigidize the work-space body to resist collapse by intra-abdominal forces, and the plurality of radially extending rigidizers positioned within the wall resist radial forces.

19 Claims, 36 Drawing Sheets

(58) Field of Classification Search
    CPC .............. A61B 17/025; A61B 17/0256; A61B
                                                17/0287
    USPC ................................................. 600/201–245
    See application file for complete search history.

(56)                    References Cited

U.S. PATENT DOCUMENTS

| | | |
|---|---|---|
| 4,478,580 A | 10/1984 | Barrut |
| 4,571,180 A | 2/1986 | Kulick |
| 4,665,621 A | 5/1987 | Ackerman et al. |
| 4,764,114 A | 8/1988 | Jeffcoat et al. |
| 4,790,751 A | 12/1988 | Reinhardt et al. |
| 4,873,651 A | 10/1989 | Raviv |
| 4,883,425 A | 11/1989 | Zimble |
| 4,935,635 A | 6/1990 | O'Harra |
| 5,051,823 A | 9/1991 | Cooper et al. |
| 5,176,687 A | 1/1993 | Hasson et al. |
| 5,178,537 A | 1/1993 | Currie |
| 5,215,521 A | 6/1993 | Cochran et al. |
| 5,224,049 A | 6/1993 | Mushabac |
| 5,230,621 A | 7/1993 | Jacoby |
| 5,244,387 A | 9/1993 | Fuierer |
| 5,257,184 A | 10/1993 | Mushabac |
| 5,308,327 A | 5/1994 | Heaven et al. |
| 5,313,053 A | 5/1994 | Koenck et al. |
| 5,318,442 A | 6/1994 | Jeffcoat et al. |
| 5,320,462 A | 6/1994 | Johansson et al. |
| 5,361,752 A | 11/1994 | Moll et al. |
| 5,368,597 A | 11/1994 | Pagedas |
| 5,372,502 A | 12/1994 | Massen et al. |
| 5,423,677 A | 6/1995 | Brattesani |
| 5,524,633 A | 6/1996 | Heaven et al. |
| 5,618,296 A | 4/1997 | Sorensen et al. |
| 5,743,731 A | 4/1998 | Lares et al. |
| 5,850,289 A | 12/1998 | Fowler et al. |
| 5,862,559 A | 1/1999 | Hunter |
| 5,897,509 A | 4/1999 | Toda et al. |
| 5,919,129 A | 7/1999 | Vandre |
| 5,944,523 A | 8/1999 | Badoz |
| 5,947,992 A | 9/1999 | Zadini et al. |
| 5,969,321 A | 10/1999 | Danielson et al. |
| 5,993,209 A | 11/1999 | Matoba et al. |
| 6,000,939 A | 12/1999 | Ray et al. |
| 6,007,333 A | 12/1999 | Callan et al. |
| 6,116,899 A | 9/2000 | Takeuchi |
| 6,142,936 A | 11/2000 | Beane et al. |
| 6,179,611 B1 | 1/2001 | Everett et al. |
| 6,276,934 B1 | 8/2001 | Rakocz |
| 6,309,219 B1 | 10/2001 | Robert |
| 6,406,440 B1 | 6/2002 | Stefanchik |
| 6,423,803 B1 | 7/2002 | Nagpal et al. |
| 6,468,079 B1 | 10/2002 | Fischer et al. |
| 6,589,268 B1 | 7/2003 | McEwen |
| 6,819,318 B1 | 11/2004 | Geng |
| 6,885,464 B1 | 4/2005 | Pfeiffer et al. |
| 6,942,679 B1 | 9/2005 | Terai |
| 7,041,056 B2 | 5/2006 | Deslauriers et al. |
| 7,056,329 B2 | 6/2006 | Kerr |
| 7,097,648 B1 | 8/2006 | Globerman et al. |
| 7,235,066 B1 | 6/2007 | Narini et al. |
| 7,346,417 B2 | 3/2008 | Lueth et al. |
| 7,494,338 B2 | 2/2009 | Durbin et al. |
| 7,625,335 B2 | 12/2009 | Deichmann et al. |
| 7,668,583 B2 | 2/2010 | Fegert et al. |
| 7,766,823 B2 | 8/2010 | Moll et al. |
| 7,813,591 B2 | 10/2010 | Paley et al. |
| 8,280,152 B2 | 10/2012 | Thiel et al. |
| 8,287,561 B2 | 10/2012 | Nunez et al. |
| 8,371,848 B2 | 2/2013 | Okawa et al. |
| 8,744,194 B2 | 6/2014 | Kawasaki et al. |
| 8,764,646 B2 | 7/2014 | Grundeman |
| 8,936,470 B2 | 1/2015 | Pruckner et al. |
| 9,137,511 B1 | 9/2015 | LeGrand, III et al. |
| 9,179,987 B2 | 11/2015 | Goodacre |
| 9,463,081 B2 | 10/2016 | Urakabe |
| 9,522,054 B2 | 12/2016 | Kim et al. |
| 9,603,675 B2 | 3/2017 | Pruckner |
| 9,918,805 B2 | 3/2018 | Pruckner |
| 10,136,970 B2 | 11/2018 | Pesach |
| 10,182,875 B2 | 1/2019 | Yates |
| 10,206,666 B2 | 2/2019 | Dickson |
| 10,226,599 B2 | 3/2019 | Schaffer |
| 10,299,880 B2 | 5/2019 | Ramirez Luna et al. |
| 10,470,846 B2 | 11/2019 | Kopelman et al. |
| 10,695,150 B2 | 6/2020 | Kopelman et al. |
| 11,253,239 B2 | 2/2022 | Bar-Yoseph et al. |
| 2002/0103420 A1 | 8/2002 | Coleman et al. |
| 2002/0133096 A1 | 9/2002 | Toda et al. |
| 2004/0087937 A1 | 5/2004 | Eggers et al. |
| 2004/0097792 A1 | 5/2004 | Moll et al. |
| 2004/0106868 A1 | 6/2004 | Liew et al. |
| 2004/0158261 A1 | 8/2004 | Vu |
| 2005/0116673 A1 | 6/2005 | Carl et al. |
| 2006/0154198 A1 | 7/2006 | Durbin et al. |
| 2007/0037125 A1 | 2/2007 | Maev et al. |
| 2007/0042315 A1 | 2/2007 | Boutoussov et al. |
| 2007/0064242 A1 | 3/2007 | Childers |
| 2007/0065782 A1 | 3/2007 | Maschke |
| 2007/0172112 A1 | 7/2007 | Paley et al. |
| 2007/0225744 A1 | 9/2007 | Nobles et al. |
| 2007/0260231 A1 | 11/2007 | Rose et al. |
| 2008/0002011 A1 | 1/2008 | Mizutani et al. |
| 2008/0002869 A1 | 1/2008 | Scharlack et al. |
| 2008/0038688 A1 | 2/2008 | Kopelman et al. |
| 2008/0051817 A1 | 2/2008 | Leahy |
| 2008/0145817 A1 | 6/2008 | Brennan et al. |
| 2008/0160477 A1 | 7/2008 | Stookey et al. |
| 2008/0201101 A1 | 8/2008 | Hebert et al. |
| 2008/0261165 A1 | 10/2008 | Steingart et al. |
| 2009/0017416 A1 | 1/2009 | Nguyen et al. |
| 2009/0043314 A1 | 2/2009 | Sevensson et al. |
| 2009/0061383 A1 | 3/2009 | Kang |
| 2009/0087050 A1 | 4/2009 | Gandyra |
| 2009/0306506 A1 | 12/2009 | Heger et al. |
| 2009/0326383 A1 | 12/2009 | Barnes et al. |
| 2010/0047733 A1 | 2/2010 | Nahlieli |
| 2010/0092908 A1 | 4/2010 | Rothenwaender et al. |
| 2010/0189341 A1 | 7/2010 | Oota et al. |
| 2010/0238279 A1 | 9/2010 | Thoms et al. |
| 2010/0239136 A1 | 9/2010 | Gandyra et al. |
| 2010/0239996 A1 | 9/2010 | Ertl |
| 2010/0268069 A1 | 10/2010 | Liang |
| 2010/0268071 A1 | 10/2010 | Kim |
| 2010/0305435 A1 | 12/2010 | Magill |
| 2011/0087235 A1 | 4/2011 | Taylor et al. |
| 2011/0184245 A1 | 7/2011 | Xia et al. |
| 2011/0184432 A1* | 7/2011 | Parihar ............ A61B 17/00234 606/114 |
| 2011/0190781 A1 | 8/2011 | Collier et al. |
| 2011/0301419 A1 | 12/2011 | Craft et al. |
| 2012/0015329 A1 | 1/2012 | Gross et al. |
| 2012/0040305 A1 | 2/2012 | Karazivan et al. |
| 2012/0046536 A1 | 2/2012 | Cheung et al. |
| 2012/0097002 A1 | 4/2012 | Thiedig |
| 2012/0158033 A1 | 6/2012 | Deal |
| 2012/0179281 A1 | 7/2012 | Steingart et al. |
| 2012/0189182 A1 | 7/2012 | Liang et al. |
| 2012/0270177 A1 | 10/2012 | Nakashima et al. |
| 2012/0271176 A1 | 10/2012 | Moghaddam et al. |
| 2013/0000666 A1 | 1/2013 | Hu |
| 2013/0017507 A1 | 1/2013 | Moffson et al. |
| 2013/0027515 A1 | 1/2013 | Vinther et al. |
| 2013/0188012 A1 | 7/2013 | Bellis et al. |
| 2013/0209953 A1 | 8/2013 | Arlinsky et al. |
| 2013/0253278 A1 | 9/2013 | Smith |
| 2013/0273492 A1 | 10/2013 | Suttin, Sr. et al. |
| 2014/0066784 A1 | 3/2014 | Yokota |
| 2014/0093835 A1 | 4/2014 | Levin |
| 2014/0111616 A1 | 4/2014 | Blayvas |
| 2014/0120492 A1 | 5/2014 | Loannidis et al. |
| 2014/0120493 A1 | 5/2014 | Levin |
| 2014/0146142 A1 | 5/2014 | Duret et al. |
| 2014/0178832 A1 | 6/2014 | Choi et al. |
| 2014/0194696 A1 | 7/2014 | Fischvogt |

(56) References Cited

U.S. PATENT DOCUMENTS

| | | | |
|---|---|---|---|
| 2014/0199650 A1 | 7/2014 | Moffson et al. | |
| 2014/0221819 A1 | 8/2014 | Sarment | |
| 2014/0248577 A1 | 9/2014 | Tahmasebi et al. | |
| 2014/0275801 A1 | 9/2014 | Menchaca et al. | |
| 2014/0276055 A1 | 9/2014 | Barthe et al. | |
| 2014/0309523 A1 | 10/2014 | Daon et al. | |
| 2014/0330285 A1 | 11/2014 | Rosenblatt et al. | |
| 2014/0343395 A1 | 11/2014 | Choi et al. | |
| 2015/0015701 A1 | 1/2015 | Yu | |
| 2015/0118638 A1 | 4/2015 | Cowburn | |
| 2015/0182299 A1 | 7/2015 | Koubi et al. | |
| 2015/0223910 A1 | 8/2015 | Pruckner | |
| 2015/0223916 A1 | 8/2015 | Kim et al. | |
| 2015/0229911 A1 | 8/2015 | Ge et al. | |
| 2015/0297254 A1 | 10/2015 | Sullivan et al. | |
| 2015/0348320 A1 | 12/2015 | Pesach et al. | |
| 2016/0100857 A1* | 4/2016 | Wachli | A61B 17/3423 |
| | | | 600/204 |
| 2016/0120615 A1 | 5/2016 | Scurtescu | |
| 2016/0259515 A1 | 9/2016 | Sabina et al. | |
| 2016/0262856 A1 | 9/2016 | Atiya et al. | |
| 2016/0270878 A1 | 9/2016 | Fulton, III | |
| 2016/0278757 A1 | 9/2016 | Piskun et al. | |
| 2016/0302783 A1 | 10/2016 | Greenberg et al. | |
| 2016/0338682 A1 | 11/2016 | Hoyte et al. | |
| 2016/0338803 A1 | 11/2016 | Pesach | |
| 2017/0007377 A1 | 1/2017 | Pesach et al. | |
| 2017/0079708 A1 | 3/2017 | Gilbert et al. | |
| 2017/0128059 A1 | 5/2017 | Coe et al. | |
| 2017/0202483 A1 | 7/2017 | Sorimoto et al. | |
| 2017/0252026 A1 | 9/2017 | Gupta et al. | |
| 2018/0008250 A1 | 1/2018 | Joseph | |
| 2018/0049830 A1 | 2/2018 | Yates et al. | |
| 2018/0360481 A1 | 12/2018 | Bonadio et al. | |
| 2019/0117241 A1 | 4/2019 | Sherman et al. | |
| 2019/0192262 A1 | 6/2019 | Pesach | |
| 2019/0247033 A1 | 8/2019 | Yaari | |
| 2019/0262098 A1 | 8/2019 | Pesach et al. | |
| 2019/0328376 A1 | 10/2019 | Bar-Yoseph et al. | |
| 2019/0343598 A1 | 11/2019 | Knobel et al. | |
| 2020/0060550 A1 | 2/2020 | Pesach et al. | |
| 2020/0155285 A1 | 5/2020 | Pesach et al. | |
| 2020/0268410 A1 | 8/2020 | Yaari et al. | |
| 2022/0071737 A1 | 3/2022 | Pesach et al. | |
| 2022/0160342 A1 | 5/2022 | Bar-Yoseph et al. | |

FOREIGN PATENT DOCUMENTS

| | | |
|---|---|---|
| CN | 101677757 | 3/2010 |
| EP | 1707130 | 10/2006 |
| EP | 1901033 | 3/2008 |
| EP | 2165674 | 3/2010 |
| EP | 2485664 | 8/2012 |
| EP | 2630929 | 8/2013 |
| EP | 3558143 | 8/2021 |
| ES | 2115544 | 6/1998 |
| FR | 2692773 | 12/1993 |
| GB | 2495522 | 4/2013 |
| JP | 63-005742 | 1/1988 |
| JP | 07-155297 | 6/1995 |
| JP | 10-165425 | 6/1998 |
| JP | 10-262996 | 10/1998 |
| JP | 11-192207 | 7/1999 |
| JP | 2000-505657 | 5/2000 |
| JP | 2002-125927 | 5/2002 |
| JP | 2003-325451 | 11/2003 |
| JP | 2006-102497 | 4/2006 |
| JP | 2007-152004 | 6/2007 |
| JP | 2007-296249 | 11/2007 |
| JP | 2009-268614 | 11/2009 |
| JP | 2010-104652 | 5/2010 |
| JP | 2012-016573 | 1/2012 |
| JP | 5016311 | 6/2012 |
| JP | 2014-236957 | 12/2014 |
| JP | 5661255 | 1/2015 |
| KR | 10-1782740 | 9/2017 |
| WO | WO 95/30375 | 11/1995 |
| WO | WO 98/06352 | 2/1998 |
| WO | WO 98/09569 | 3/1998 |
| WO | WO 2004/002327 | 1/2004 |
| WO | WO 2005/104959 | 11/2005 |
| WO | WO 2007/063980 | 6/2007 |
| WO | WO 2008/013181 | 1/2008 |
| WO | WO 2011/044448 | 4/2011 |
| WO | WO 2014/020247 | 2/2014 |
| WO | WO 2014/102779 | 7/2014 |
| WO | WO 2015/028646 | 3/2015 |
| WO | WO 2015/084769 | 6/2015 |
| WO | WO 2015/107520 | 7/2015 |
| WO | WO 2016/028429 | 2/2016 |
| WO | WO 2016/028789 | 2/2016 |
| WO | WO 2016/064617 | 4/2016 |
| WO | WO 2016/068825 | 5/2016 |
| WO | WO 2016/110855 | 7/2016 |
| WO | WO 2016/113745 | 7/2016 |
| WO | WO 2016/178212 | 11/2016 |
| WO | WO 2017/125926 | 7/2017 |
| WO | WO 2017/216803 | 12/2017 |
| WO | WO 2018/047180 | 8/2018 |
| WO | WO 2019/008586 | 1/2019 |
| WO | WO 2019/021285 | 1/2019 |
| WO | WO 2019/049152 | 3/2019 |
| WO | WO 2020/144692 | 7/2020 |
| WO | WO 2022/130385 | 6/2022 |

OTHER PUBLICATIONS

Applicant-Initiated Interview Summary Dated Aug. 2, 2017 From the US Patent and Trademark Office Re. U.S. Appl. No. 15/115,196. (3 pages).

Communication Pursuant to Article 94(3) EPC Dated Oct. 5, 2021 From the European Patent Office Re. Application No. 18759184.7. (6 Pages).

Communication Pursuant to Article 94(3) EPC Dated Oct. 7, 2020 From the European Patent Office Re. Application No. 177805300.6. (5 Pages).

Communication Pursuant to Article 94(3) EPC Dated Aug. 10, 2017 From the European Patent Office Re. Application No. 13830124.7. (6 Pages).

Communication Pursuant to Article 94(3) EPC Dated Mar. 10, 2023 From the European Patent Office Re. Application No. 17780530.6 (3 Pages).

Communication Pursuant to Article 94(3) EPC Dated Nov. 16, 2021 From the European Patent Office Re. Application No. 17707964.7. (4 Pages).

Communication Pursuant to Article 94(3) EPC Dated Nov. 19, 2018 From the European Patent Office Re. Application No. 13830124.7. (8 Pages).

Communication Pursuant to Article 94(3) EPC Dated Nov. 19, 2020 From the European Patent Office Re. Application No. 13830124.7. (6 Pages).

Communication Pursuant to Article 94(3) EPC Dated Jun. 22, 2023 From the European Patent Office Re. Application No. 17812894.8. (7 Pages).

Communication Pursuant to Article 94(3) EPC Dated Jan. 29, 2021 From the European Patent Office Re. Application No. 18769813.9. (9 Pages).

Communication Pursuant to Article 94(3) EPC Dated Nov. 30, 2021 From the European Patent Office Re. Application No. 17780530.6. (4 Pages).

Communication Pursuant to Article 94(3) EPC Dated Jan. 31, 2020 From the European Patent Office Re. Application No. 17780530.6. (3 Pages).

Communication Pursuant to Rules 70(2) and 70a(2) EPC Dated Sep. 7, 2018 From the European Patent Office Re. Application No. 16789407.0. (1 Page).

Communication Relating to the Results of the Partial International Search and the Provisional Opinion Dated Jun. 14, 2017 From the International Searching Authority Re. Application No. PCT/IL2017/050072. (12 Pages).

(56) References Cited

OTHER PUBLICATIONS

Communication Relating to the Results of the Partial International Search Dated May 8, 2014 From the International Searching Authority Re. Application No. PCT/IL2013/051059.

Decision of Rejection Dated Jan. 14, 2020 From the Japan Patent Office Re. Application No. 2017-228103 and Its Translation Into English. (7 Pages).

Decision to Refuse A European Patent Application Dated Oct. 18, 2022 From the European Patent Office Re. Application No. 18769813.9. (15 Pages).

English Translation Dated Nov. 30, 2021 of Ground(s) of Reason of Rejection Dated Nov. 19, 2021 From the Korean Intellectual Property Office Re. Application No. 2010-7032325. (2 Pages).

European Search Report and the European Search Opinion Dated Jan. 3, 2022 From the European Patent Office Re. Application No. 21200149.9. (10 Pages).

European Search Report and the European Search Opinion Dated Feb. 4, 2020 From the European Patent Office Re. Application 19211372.8. (10 Pages).

Final Official Action Dated Apr. 12, 2021 From the US Patent and Trademark Office Re. U.S. Appl. No. 16/310,435. (19 Pages).

Final Official Action Dated Dec. 28, 2020 from the US Patent and Trademark Office Re. U.S. Appl. No. 16/634,152. (29 pages).

Ground(s) of Reason of Rejection Dated Nov. 19, 2021 From the Korean Intellectual Property Office Re. Application No. 2010-7032325. (2 Pages).

International Preliminary Report on Patentability Dated Aug. 2, 2018 From the International Bureau of WIPO Re. Application No. PCT/IL2017/050072. (10 Pages).

International Preliminary Report on Patentability Dated Feb. 6, 2020 From the International Bureau of WIPO Re. Application No. PCT/IL2018/050825. (10 Pages).

International Preliminary Report on Patentability Dated Jul. 9, 2015 From the International Bureau of WIPO Re. Application No. PCT/IL2013/051059.

International Preliminary Report on Patentability Dated Jan. 16, 2020 From the International Bureau of WIPO Re. Application No. PCT/IL2018/050731. (9 Pages).

International Preliminary Report on Patentability Dated Nov. 16, 2017 From the International Bureau of WIPO Re. Application No. PCT/IL2016/050449. (11 Pages).

International Preliminary Report on Patentability Dated Mar. 19, 2020 From the International Bureau of WIPO Re. Application No. PCT/IL2017/051014. (10 Pages).

International Preliminary Report on Patentability Dated Jul. 20, 2017 From the International Bureau of WIPO Re. Application No. PCT/IL2016/050023. (10 Pages).

International Preliminary Report on Patentability Dated Mar. 21, 2019 From the International Bureau of WIPO Re. Application No. PCT/IL2017/051015. (13 Pages).

International Preliminary Report on Patentability Dated Jul. 22, 2021 From the International Bureau of WIPO Re. Application No. PCT/IL2020/050040. (10 Pages).

International Preliminary Report on Patentability Dated Dec. 27, 2018 From the International Bureau of WIPO Re. Application No. PCT/IL2017/050674. (9 Pages).

International Preliminary Report on Patentability Dated Jul. 27, 2017 From the International Bureau of WIPO Re. Application No. PCT/IL2016/050058. (7 Pages).

International Search Report and the Written Opinion Dated Oct. 1, 2018 From the International Searching Authority Re. Application No. PCT/IL2018/050731. (16 Pages).

International Search Report and the Written Opinion Dated Sep. 2, 2014 From the International Searching Authority Re. Application No. PCT/IL2013/051059.

International Search Report and the Written Opinion Dated Jul. 6, 2022 From the International Searching Authority Re. Application No. PCT/IL2021/051499. (24 Pages).

International Search Report and the Written Opinion Dated Nov. 7, 2018 From the International Searching Authority Re. Application No. PCT/IL2018/050825. (17 Pages).

International Search Report and the Written Opinion Dated Aug. 8, 2017 From the International Searching Authority Re. Application No. PCT/IL2017/050072. (17 Pages).

International Search Report and the Written Opinion Dated Dec. 11, 2018 From the International Searching Authority Re. Application No. PCT/IL2017/051014. (18 Pages).

International Search Report and the Written Opinion Dated Apr. 18, 2016 From the International Searching Authority Re. Application No. PCT/IL2016/050058.

International Search Report and the Written Opinion Dated Sep. 18, 2017 From the International Searching Authority Re. Application No. PCT/IL2017/050674. (12 Pages).

International Search Report and the Written Opinion Dated Apr. 21, 2016 From the International Searching Authority Re. Application No. PCT/IL2016/050023.

International Search Report and the Written Opinion Dated Aug. 23, 2016 From the International Searching Authority Re. Application No. PCT/IL2016/050449.

International Search Report and the Written Opinion Dated Jul. 23, 2020 From the International Searching Authority Re. Application No. PCT/IL2020/050040. (14 Pages).

International Search Report and the Written Opinion Dated Jan. 24, 2018 From the International Searching Authority Re. Application No. PCT/IL2017/051015. (23 Pages).

Interview Summary Dated Nov. 15, 2022 from the US Patent and Trademark Office Re. U.S. Appl. No. 16/645,803. (2 pages).

Invitation to Pay Additional Fees Dated May 12, 2020 From the International Searching Authority Re. Application No. PCT/IL2020/050040. (3 Pages).

Invitation to Pay Additional Fees, Communication Relating to the Results of the Partial International Search and the Provisional Opinion Dated Apr. 8, 2022 From the International Searching Authority Re. Application No. PCT/IL2021/051499. (15 Pages).

Invitation to Pay Additional Fees, Communication Relating to the Results of the Partial International Search and the Provisional Opinion Dated Nov. 17, 2017 From the International Searching Authority Re. Application No. PCT/IL2017/051015. (17 Pages).

Notice of Allowance Dated Mar. 7, 2023 from the US Patent and Trademark Office Re. U.S. Appl. No. 16/331,974. (14 pages).

Notice of Allowance Dated Aug. 9, 2018 From the US Patent and Trademark Office Re. U.S. Appl. No. 15/571,231. (17 pages).

Notice of Allowance Dated Jul. 11, 2018 From the US Patent and Trademark Office Re. U.S. Appl. No. 15/115,196. (8 pages).

Notice of Allowance Dated May 12, 2016 From the US Patent and Trademark Office Re. U.S. Appl. No. 14/655,286.

Notice of Allowance Dated Jul. 13, 2021 from the US Patent and Trademark Office Re. U.S. Appl. No. 16/227,995. (7 pages).

Notice of Allowance Dated Dec. 15, 2021 from US Patent and Trademark Office Re. U.S. Appl. No. 16/310,435. (6 pages).

Notice of Allowance Dated Nov. 30, 2020 from the US Patent and Trademark Office Re. U.S. Appl. No. 16/071,058. (10 pages).

Notice of Reasons for Rejection Dated May 7, 2019 From the Japan Patent Office Re. Application No. 2017-228103 and Its Translation Into English. (8 Pages).

Notice of Reasons for Rejection Dated Jul. 11, 2017 From the Japan Patent Office Re. Application No. 2015-548888 and Its Translation Into English. (5 Pages).

Notice of Reasons for Rejection Dated Feb. 14, 2017 From the Japan Patent Office Re. Application No. 2015-548888 and Its Translation Into English. (10 Pages).

Notice of Reasons for Rejection Dated Sep. 25, 2018 From the Japan Patent Office Re. Application No. 2017-228103 and Its Translation Into English. (15 Pages).

Notice Requesting Submission of Opinion Dated Feb. 3, 2021 From the Korean Intellectual Property Office Re. Application No. 10-2020-7032325 and Its Translation Into English. (14 Pages).

Notice Requesting Submission of Opinion Dated Jan. 21, 2020 From the Korean Intellectual Property Office Re. Application No. 10-2019-7034814. (3 Pages).

(56) References Cited

OTHER PUBLICATIONS

Notice Requesting Submission of Opinion Dated Apr. 26, 2019 From the Korean Intellectual Property Office Re. Application No. 10-2015-7020305. (4 Pages).

Notification of Office Action and Search Report Dated Jan. 5, 2017 From the State Intellectual Property Office of the People's Republic of China Re. Application No. 201380071840.0. (7 Pages).

Notification of Office Action Dated Apr. 15, 2016 From the State Intellectual Property Office of the People's Republic of China Re. Application No. 201380071840.0.

Office Action Dated Aug. 6, 2019 From the Israel Patent Office Re. Application No. 264237 and Its Translation Into English. (6 Pages).

Official Action Dated Sep. 3, 2021 from the US Patent and Trademark Office Re. U.S. Appl. No. 16/634,152. (43 pages).

Official Action Dated Nov. 4, 2020 From the US Patent and Trademark Office Re. U.S. Appl. No. 15/274,756. (19 Pages).

Official Action Dated Mar. 9, 2017 From the US Patent and Trademark Office Re. U.S. Appl. No. 15/115,196. (26 pages).

Official Action Dated Jun. 12, 2020 from the US Patent and Trademark Office Re. U.S. Appl. No. 16/634,152. (41 pages).

Official Action Dated Dec. 13, 2017 From the US Patent and Trademark Office Re. U.S. Appl. No. 15/115,196. (26 pages).

Official Action Dated Jun. 13, 2019 From the US Patent and Trademark Office Re. U.S. Appl. No. 15/274,756. (39 pages).

Official Action Dated Oct. 13, 2022 From the US Patent and Trademark Office Re. U.S. Appl. No. 16/331,974. (83 Pages).

Official Action Dated May 15, 2020 from the US Patent and Trademark Office Re. U.S. Appl. No. 16/071,058. (31 pages).

Official Action Dated Aug. 19, 2021 From the US Patent and Trademark Office Re. U.S. Appl. No. 16/310,435. (7 Pages).

Official Action Dated Feb. 19, 2021 From the US Patent and Trademark Office Re. U.S. Appl. No. 16/227,995. (27 Pages).

Official Action Dated Oct. 27, 2020 From the US Patent and Trademark Office Re. U.S. Appl. No. 16/310,435. (11 Pages).

Official Action Dated Sep. 27, 2022 from US Patent and Trademark Office Re. U.S. Appl. No. 16/645,803. (76 pages).

Official Action Dated Sep. 28, 2016 From the US Patent and Trademark Office Re. U.S. Appl. No. 15/115,196. (19 pages).

Official Action Dated Apr. 3, 2020 from the US Patent and Trademark Office Re. U.S. Appl. No. 16/199,954. (31 pages).

Provision of the Minutes in Accordance With Rule 124(4) EPC Dated Oct. 12, 2022 From the European Patent Office Re. Application No. 18769813.9. (11 Pages).

Requisition by the Examiner Dated Oct. 4, 2019 From the Innovation, Science and Economic Development Canada, Canadian Intellectual Property Office Re. Application No. 2,896,210. (3 Pages).

Restriction Official Action Dated May 3, 2022 from US Patent and Trademark Office Re. U.S. Appl. No. 16/645,803. (7 pages).

Restriction Official Action Dated May 5, 2023 from the US Patent and Trademark Office Re. U.S. Appl. No. 17/670,56. (6 pages).

Restriction Official Action Dated Nov. 14, 2019 From the US Patent and Trademark Office Re. U.S. Appl. No. 16/199,954. (6 pages).

Restriction Official Action Dated May 17, 2022 from US Patent and Trademark Office Re. U.S. Appl. No. 16/331,974. (10 pages).

Restriction Official Action Dated Sep. 26, 2018 From the US Patent and Trademark Office Re. U.S. Appl. No. 15/274,756. (10 Pages).

Summons to Attend Oral Proceedings Pursuant to Rule 115(1) EPC Dated Mar. 18, 2022 From the European Patent Office Re. Application No. 18769813.9. (9 Pages).

Summons to Attend Oral Proceedings Pursuant to Rule 115(1) EPC Dated Mar. 19, 2020 From the European Patent Office Re. Application No. 13830124.7. (13 Pages).

Summons to Attend Oral Proceedings Pursuant to Rule 115(1) EPC Dated Mar. 19, 2021 From the European Patent Office Re. Application No. 17780530.6. (7 Pages).

Summons to Attend Oral Proceedings Pursuant to Rule 115(1) EPC Dated Apr. 20, 2021 From the European Patent Office Re. Application No. 17780530.6. (2 Pages).

Supplementary European Search Report and the European Search Opinion Dated Feb. 7, 2023 From the European Patent Office Re. Application No. 22213874.5. (11 Pages).

Supplementary European Search Report and the European Search Opinion Dated Feb. 19, 2021 From the European Patent Office Re. Application No. 18837606.5. (7 Pages).

Supplementary European Search Report and the European Search Opinion Dated Aug. 21, 2018 From the European Patent Office Re. Application No. 16789407.0. (6 Pages).

Supplementary European Search Report and the European Search Opinion Dated Jan. 21, 2020 From the European Patent Office Re. Application No. 17812894.8. (10 Pages).

Translation Dated Feb. 2, 2020 of Notice Requesting Submission of Opinion Dated Jan. 21, 2020 From the Korean Intellectual Property Office Re. Application No. 10-2019-7034814. (3 Pages).

Translation Dated May 9, 2019 of Notice Requesting Submission of Opinion Dated Apr. 26, 2019 From the Korean Intellectual Property Office Re. Application No. 10-2015-7020305. (4 Pages).

Translation Dated Nov. 30, 2021 of Ground(s) of Reason of Rejection Dated Nov. 19, 2021 From the Korean Intellectual Property Office Re. Application No. 2010-7032325. (2 Pages).

Translation of Notification of Apr. 15, 2016 From the State Intellectual Property Office of the People's Republic of China Re. Application No. 201380071840.0.

Translation of Notification of Office Action Dated Jan. 5, 2017 From the State Intellectual Property Office of the People's Republic of China Re. Application No. 201380071840.0. (4 Pages).

Bouguet et al. "3D Photography Using Shadows in Dual-Space Geometry", The International Journal of Computer Vision, 35(2): 129-149, Nov./Dec. 1999.

Fluegge et al. "Precision of Intraoral Digital Dental Impressions With iTero and Extraoral Digitization With the iTero and a Model Scanner", American Journal of Orthodontics and Dentofacial Orthopedics, 144(3): 471-478, Sep. 2013.

Geng "Structured-Light 3D Surface Imaging: A Tutorial", Advances in Optics and Photonics, 3: 128-160, 2011.

Goshtasby et al. "A System for Digital Reconstruction of Gypsum Dental Casts", IEEE Transactions on Medical Imaging, 16(5): , Oct. 1997.

Logozzo et al. "Recent Advances in Dental Optics—Part I: 3D Intraoral Scanners for Restorative Dentistry", Optics and Lasers in Engineering, 54: 203-221, Mar. 2014.

Maintz et al. "A Survey of Medical Image Registration", Medical Image Analysis, 2(1): 1-36, Mar. 1998.

Medeiros et al. "Coded Structred Light for 3D-Photography: An Overview", IEEE—RITA, (Latin-American Learning Technologies Journal), IV(2): 109-124, Jul. 1999.

OmniVision "OVM6946 400×400. Compact, Cost-Effective Wafer-Level Camera Module for Single-Use Endoscopes", Omni Vision, Product Brief, 2 P., Aug. 10, 2016.

Paperno et al. "A New Method for Magnetic Position and Orientation Tracking", IEEE Transactions on Magnetics, XP011033696, 37(4): 1938-1940, Jul. 2001.

Salvi et al. "Pattern Codification Strategies in Structured Light Systems", Pattern Recognition, 37(4): 827-849, 2004.

Savarese et al. "3D Reconstruction by Shadow Carving: Theory and Practical Evaluation", International Journal of Computer Vision, 71(3): 305-336, Published Online Jun. 1, 2006.

Toshiba "IK-CT2: 0.7×0.7 mm, 220×220, CMOS", Toshiba Information Systems, Product Sheet, 1 P., Dec. 2016.

Communication Pursuant to Article 94(3) EPC Dated Oct. 9, 2024 From the European Patent Office Re. Application No. 17812894.8. (7 Pages).

Interview Summary Dated Oct. 25, 2024 from the US Patent and Trademark Office Re. U.S. Appl. No. 17/670,562. (10 pages).

Official Action Dated May 23, 2024 from the US Patent and Trademark Office Re. U.S. Appl. No. 16/645,803. (5 pages).

Restriction Official Action Dated Oct. 31, 2024 from US Patent and Trademark Office Re. U.S. Appl. No. 16/645,803. (2 pages).

Official Action Dated Aug. 23, 2023 from the US Patent and Trademark Office Re. U.S. Appl. No. 16/645,803. (18 pages).

Official Action Dated Aug. 24, 2023 from the US Patent and Trademark Office Re. U.S. Appl. No. 17/670,562. (102 pages).

(56)            References Cited

OTHER PUBLICATIONS

Official Action Dated May 14, 2024 from the US Patent and Trademark Office Re. U.S. Appl. No. 17/670,562. (26 pages).
Notice of Reasons for Rejection Dated Jun. 17, 2025 From the Japan Patent Office Re Application No. 2023-536819 and its Translation into English. (18 Pages).
Notification of Office Action and Search Report Dated Jan. 16, 2026 From the State Intellectual Property Office of the People's Republic of China Re. Application No. 202180091512.1 and its Machine Translation Into English. (27 Pages).

* cited by examiner

102

Providing ribs —150

Shaping at least one sheet (optional) —152

Aligning ribs relative to at least one sheet 154

Fixing the sheets to interconnecting ribs 156

Removing aligner (optional) 158

Removing shaper (optional) 160

Bending wall to form cylinder (optional) 162

Connecting inflation tube (optional) 164

Connecting ring ends 166

Closing a first opening of the ring 168

Fig. 2A                      Fig. 2B
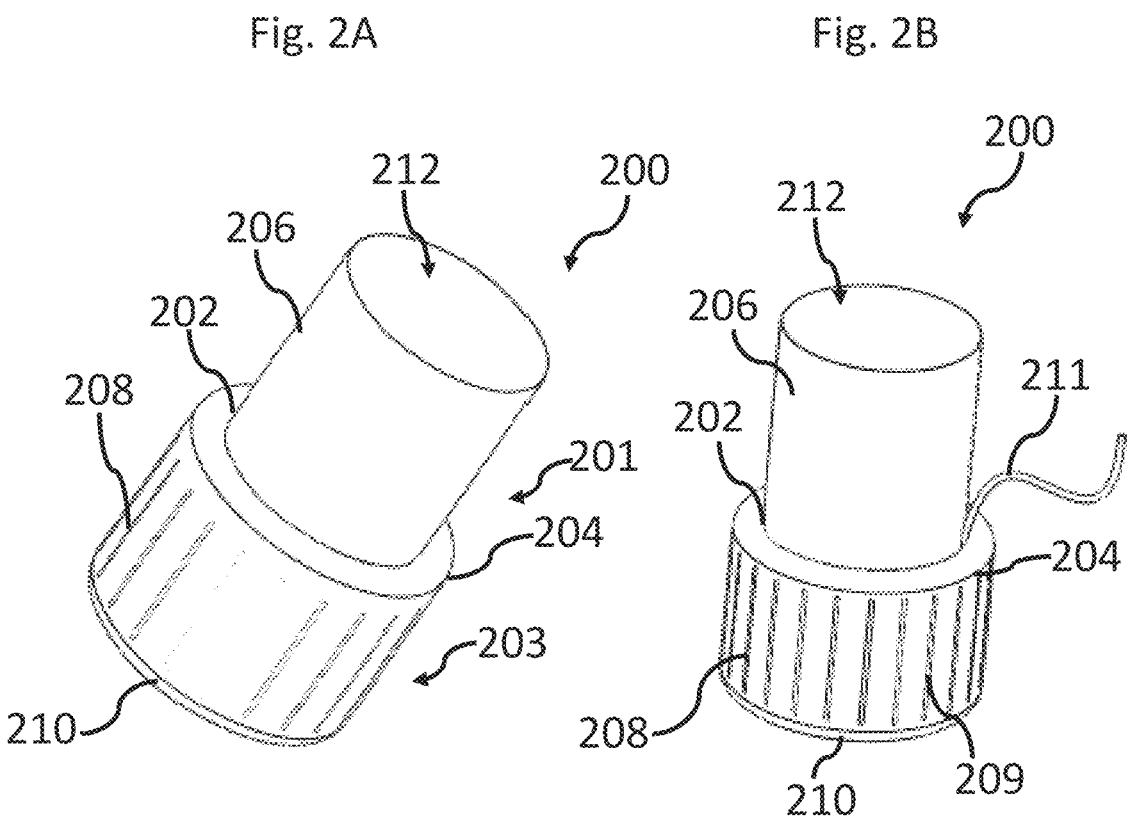
Fig. 2C
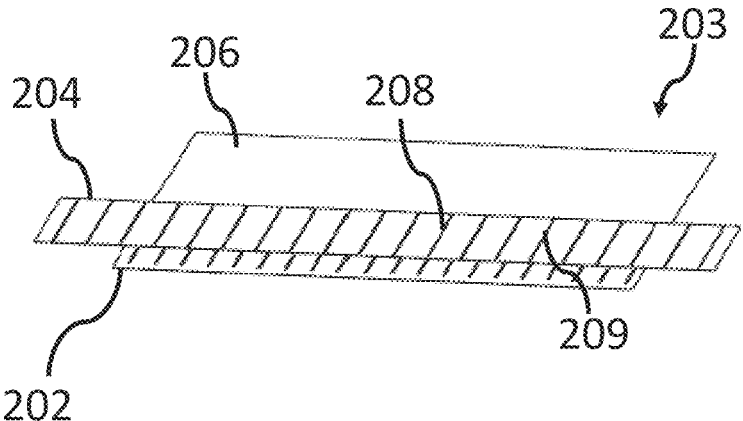

Fig. 5A
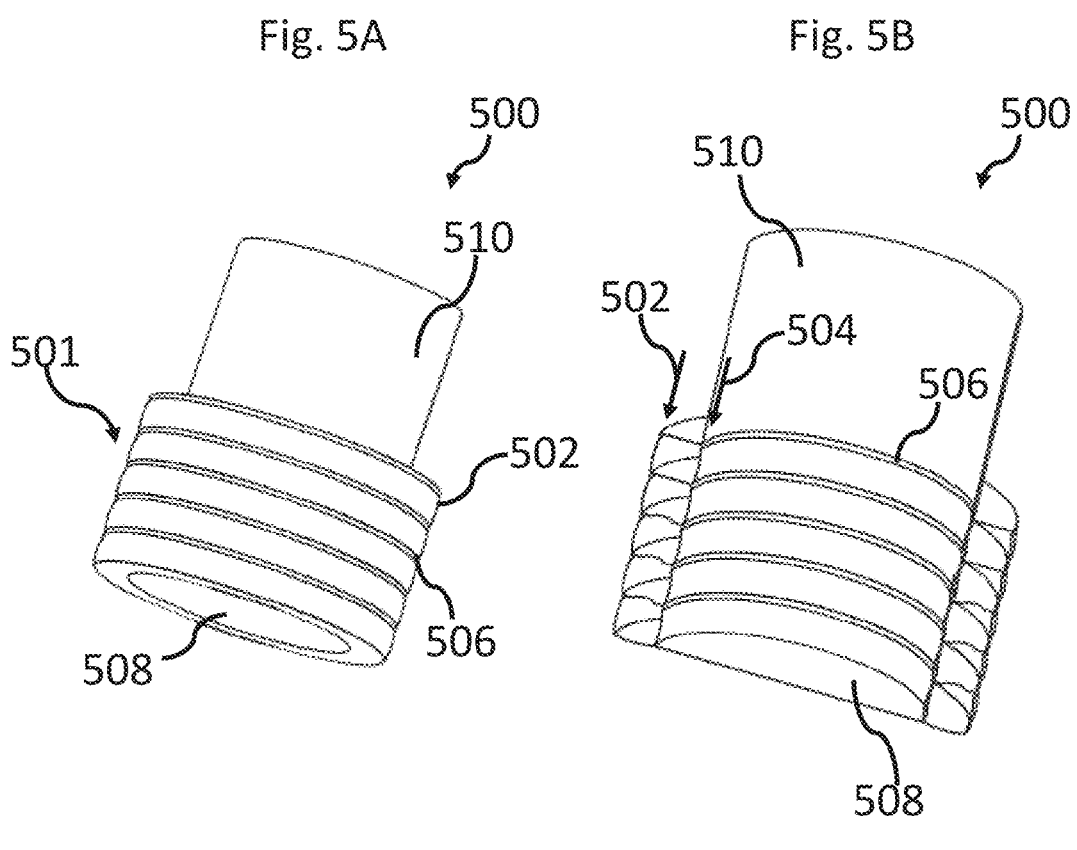
Fig. 5B
Fig. 5C
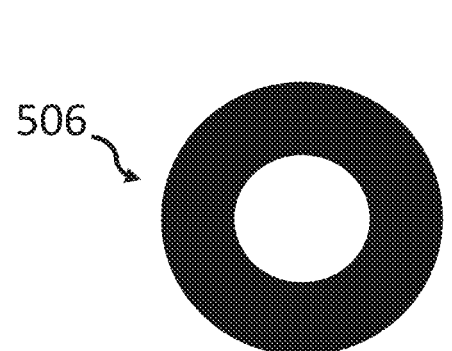
Fig. 5D
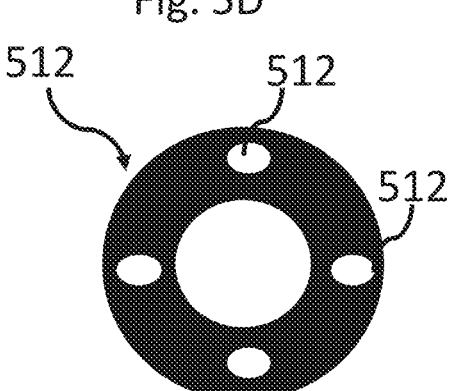

604   602

603

606

610

608   609

611   616

614   612

606

616

610

608

604

616

606   609   611

604

612

608

613

604   616

606

610   608

Fig. 7A
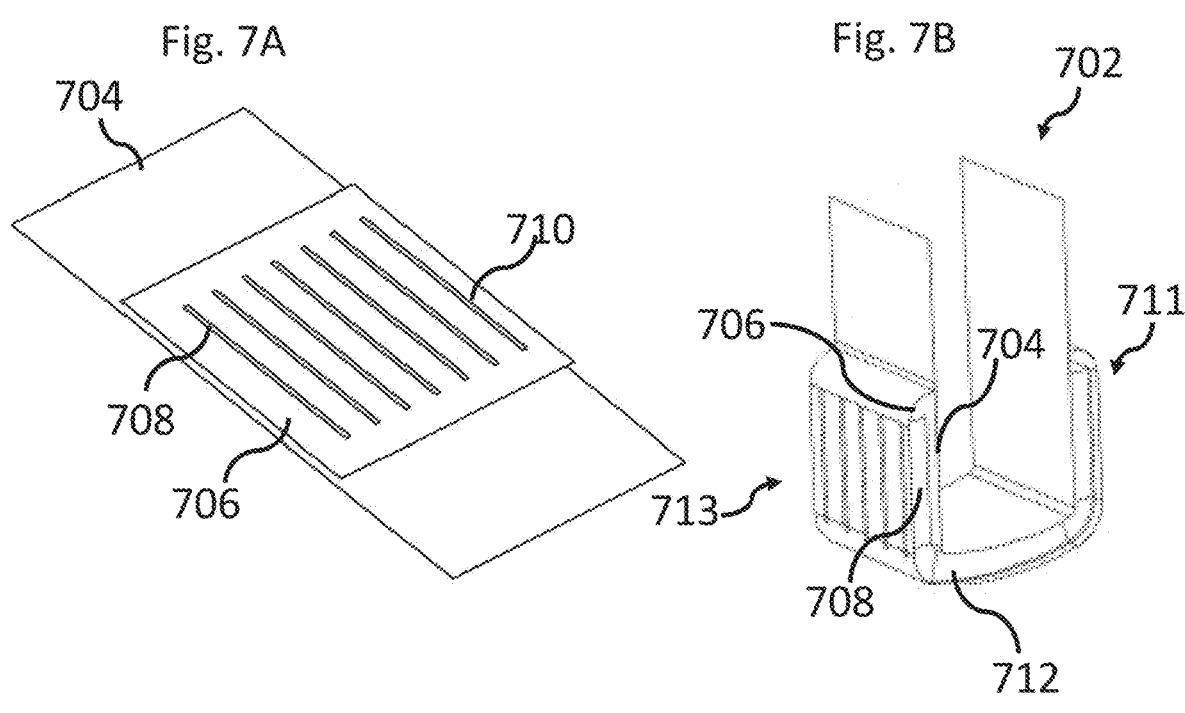
Fig. 7B
Fig. 7C
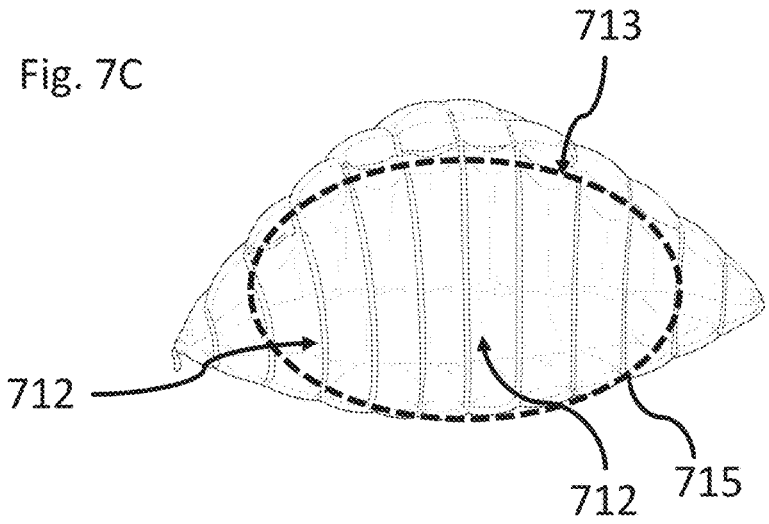
Fig. 7D
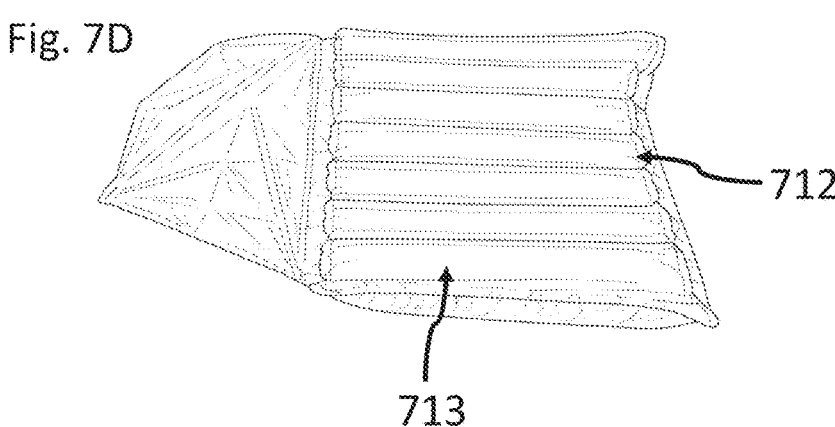

Fig. 8A
Fig. 8B
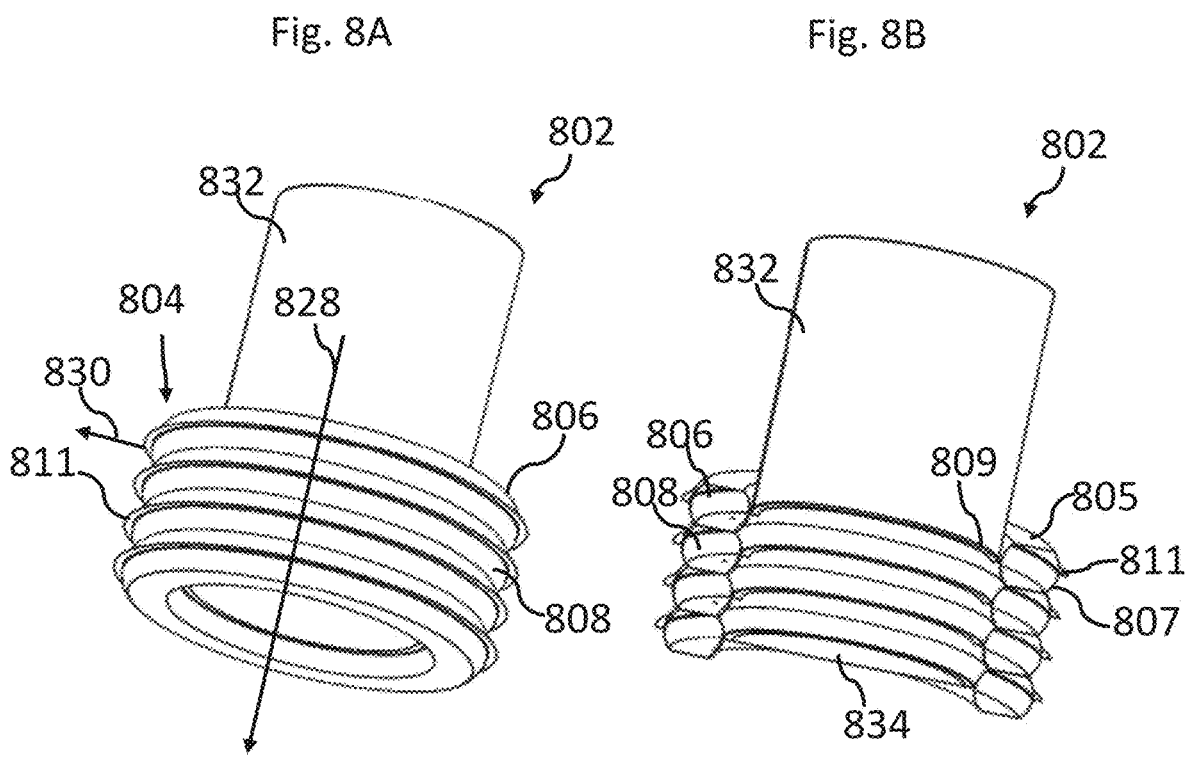
Fig. 8C
Fig. 8D
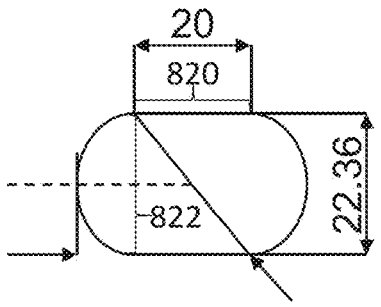
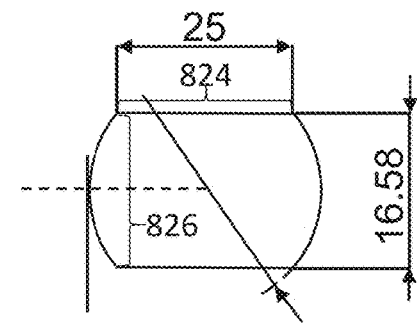

Fig. 9A
Fig. 9B
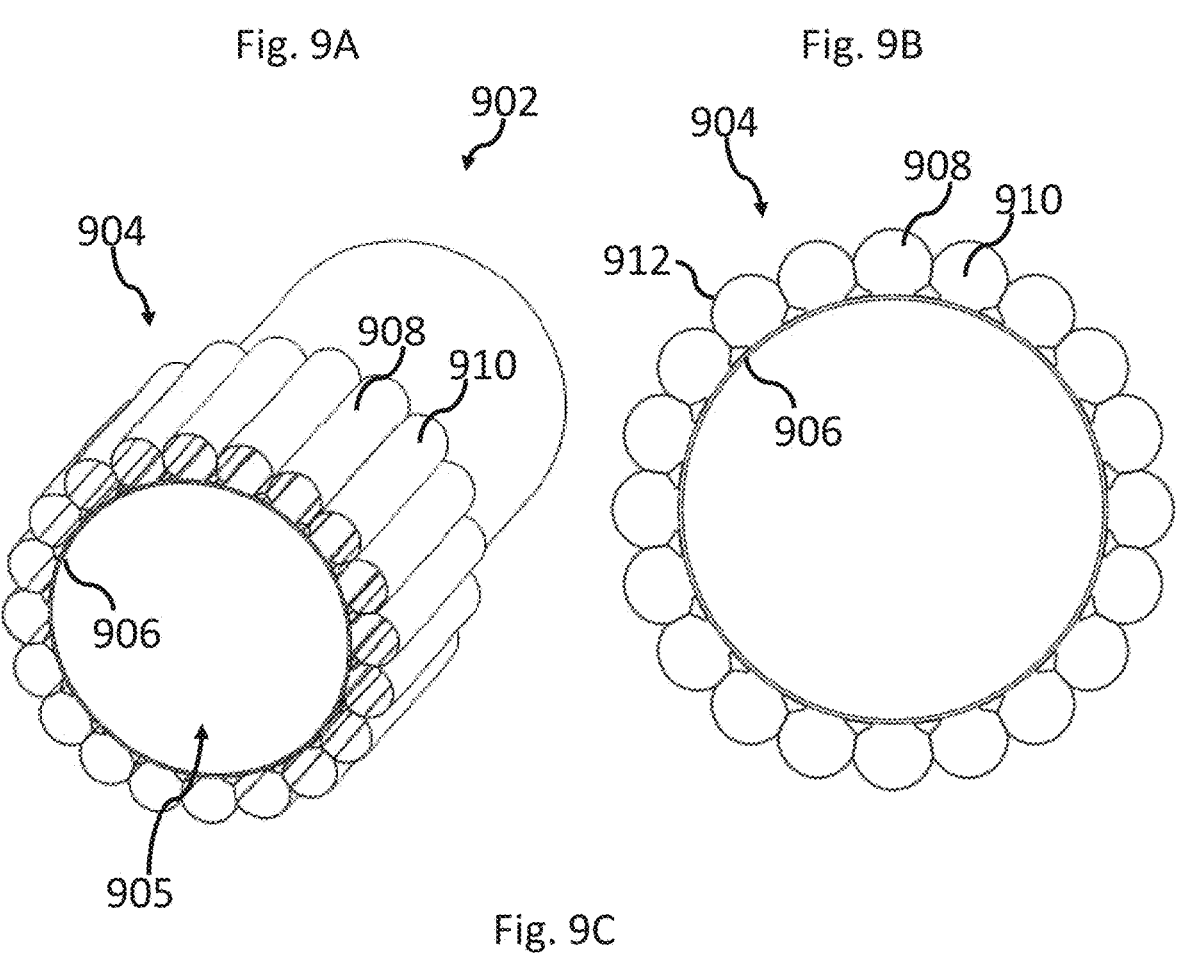
Fig. 9C
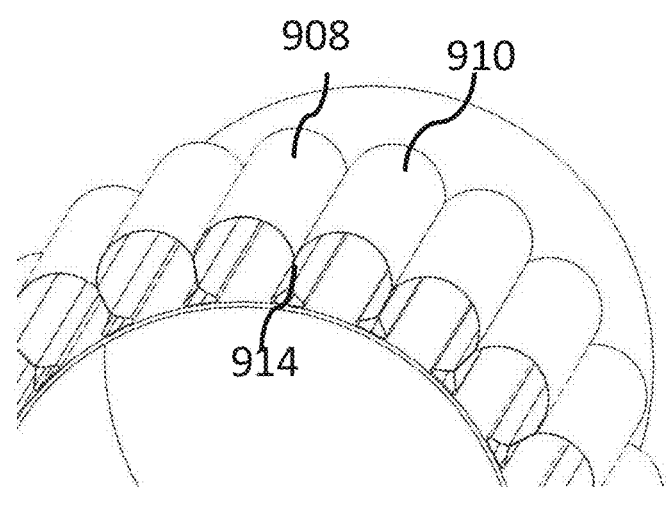

Fig. 13A
Fig. 13B
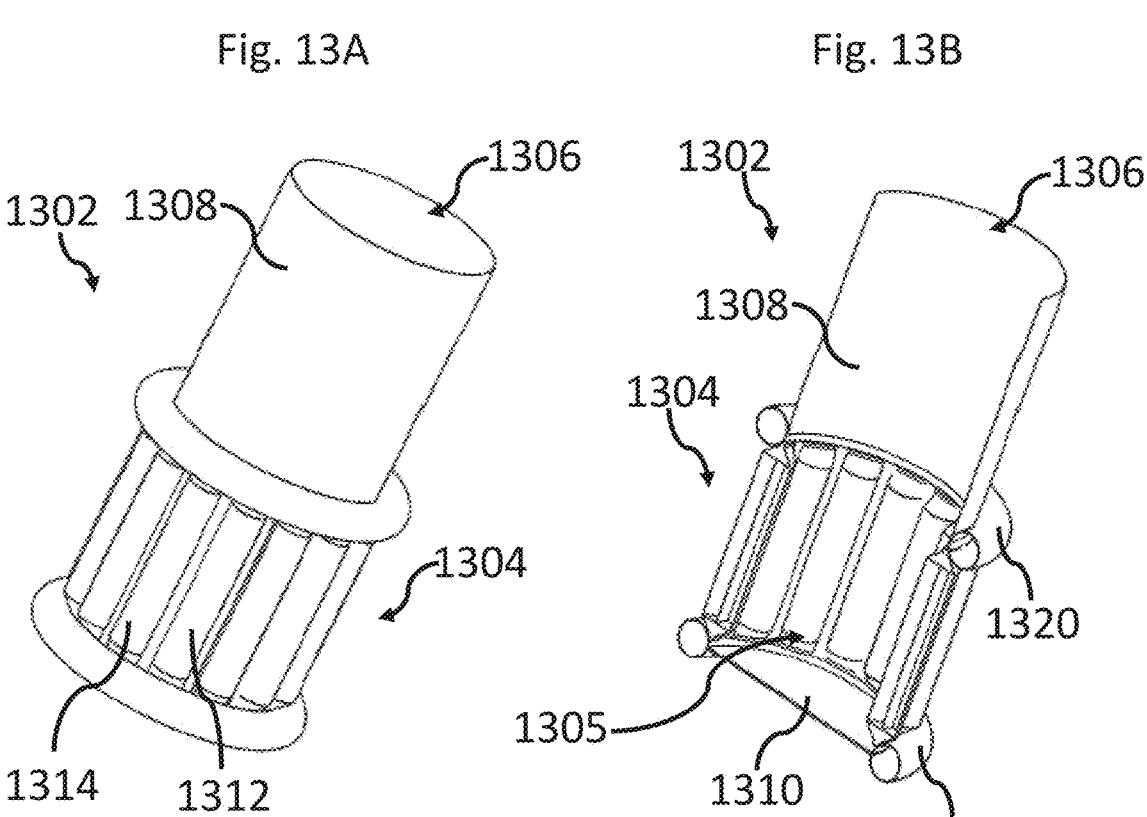
Fig. 13C
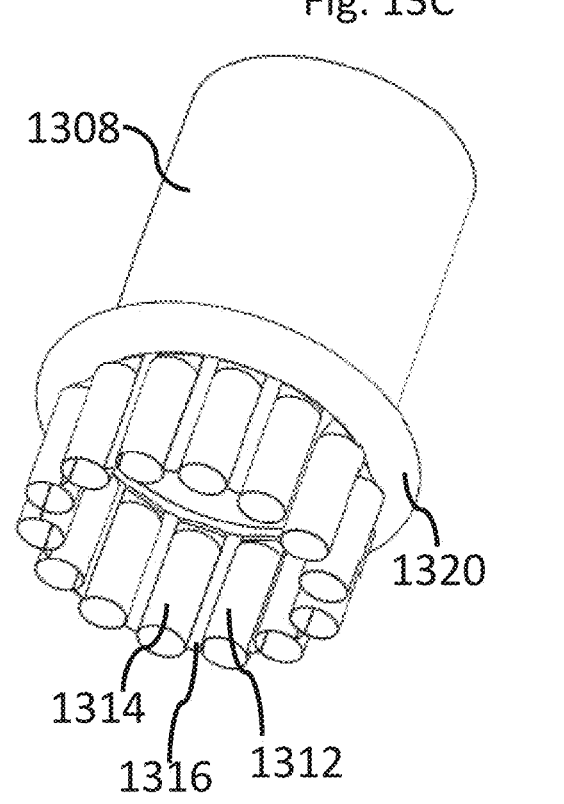

Fig. 16A                  Fig. 16B
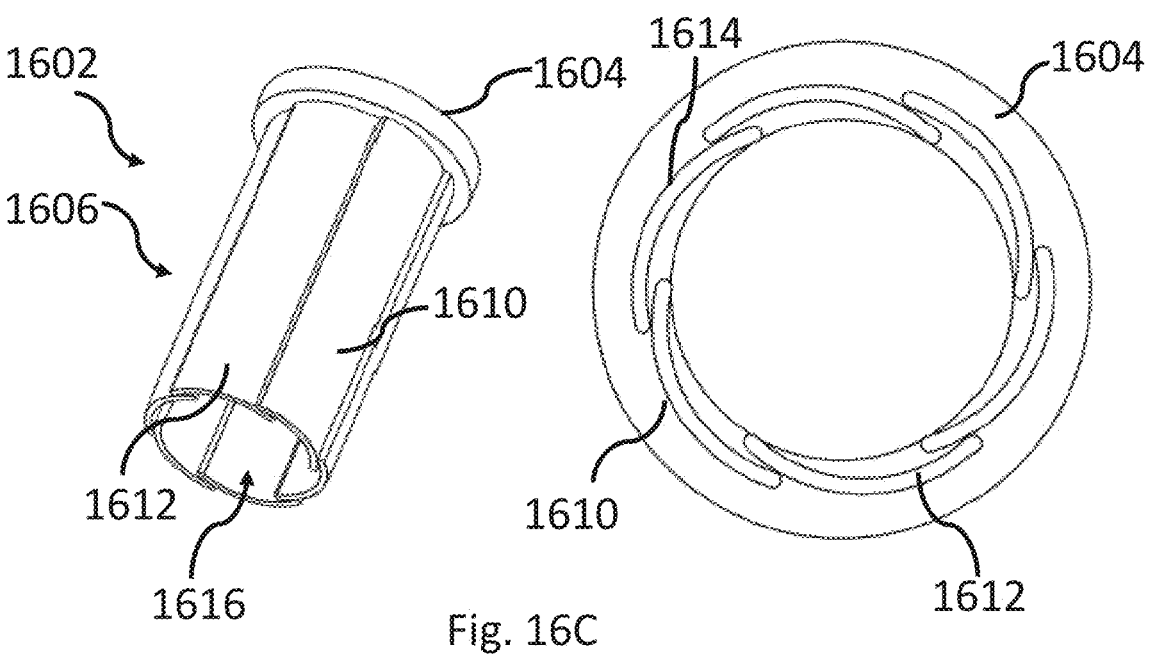
Fig. 16C
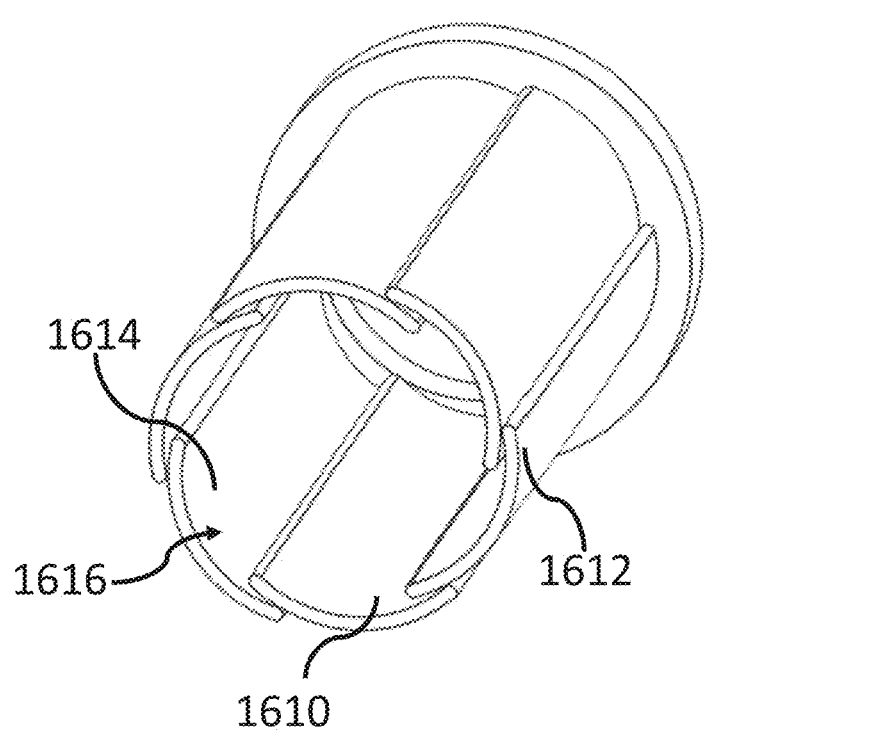

1702

1704

1708

1706

1712

1710

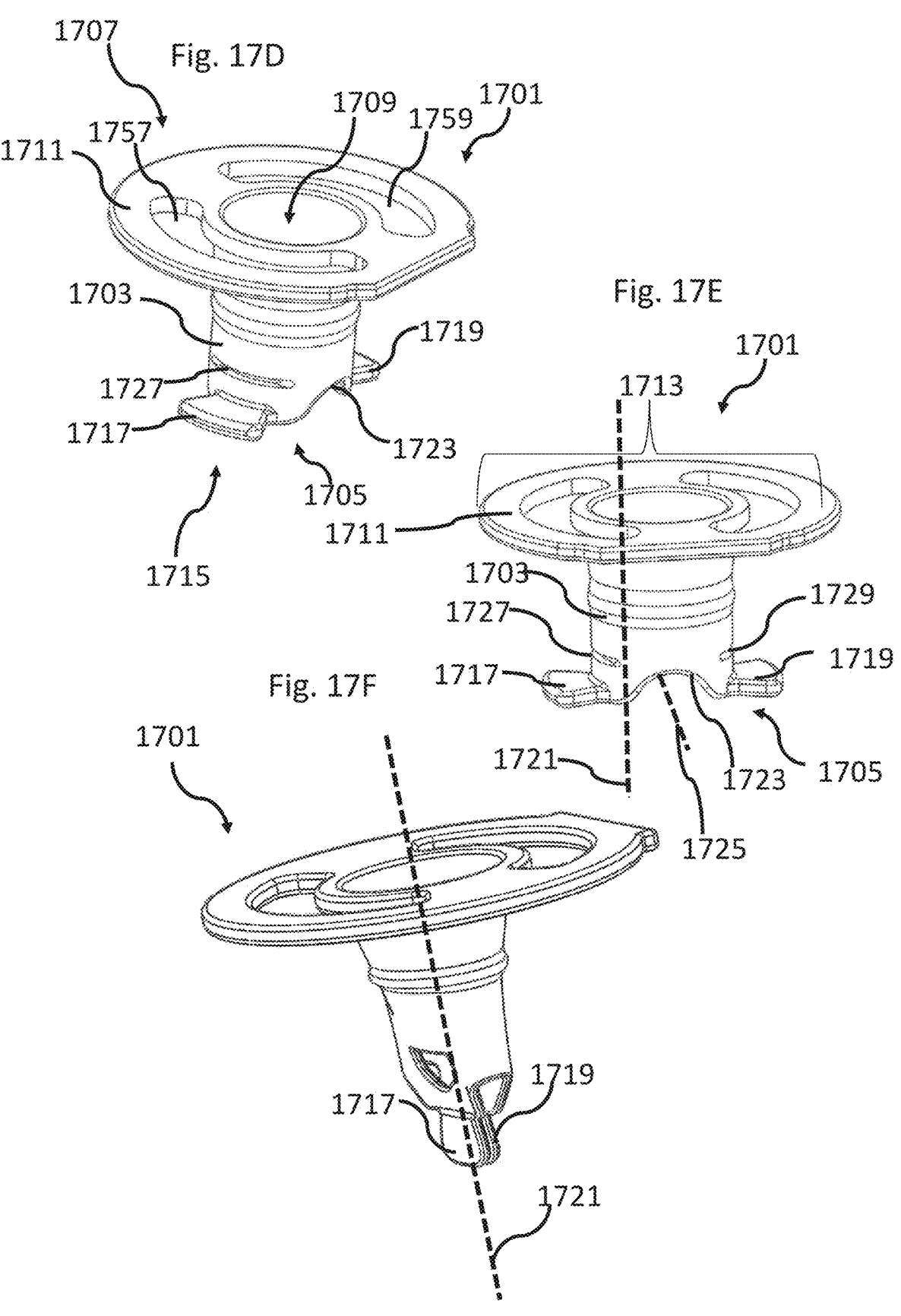

Fig. 17J
Fig. 17K
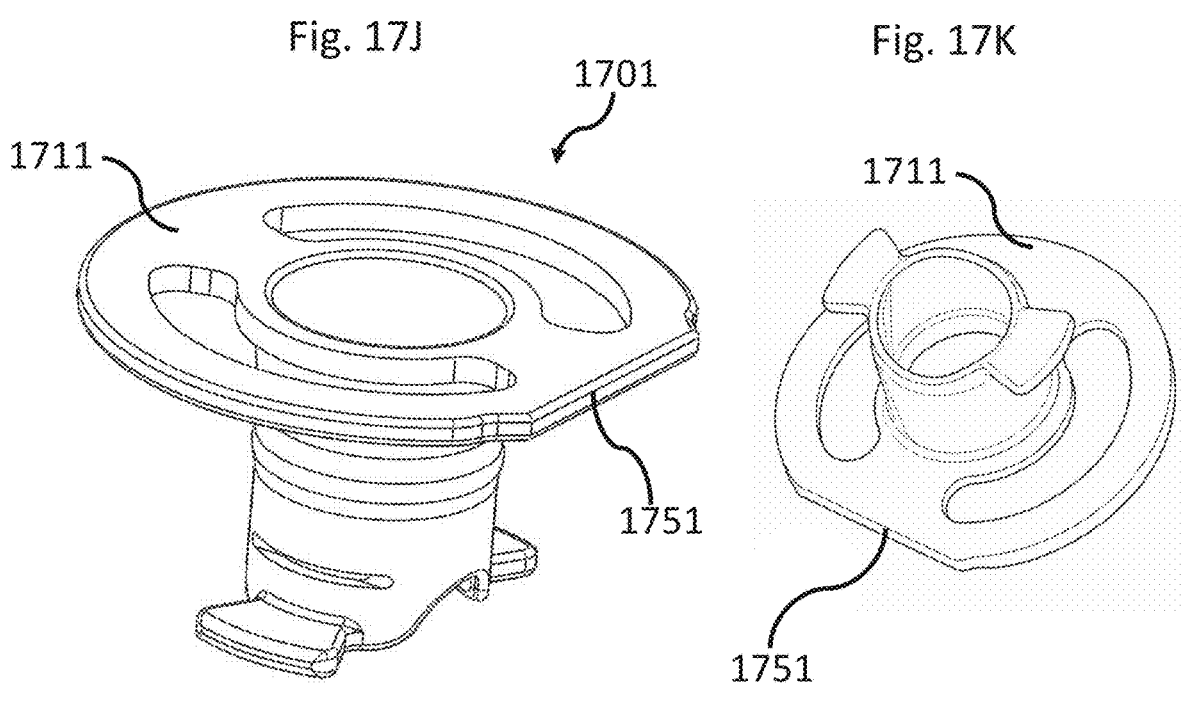
Fig. 17L
Fig. 17M
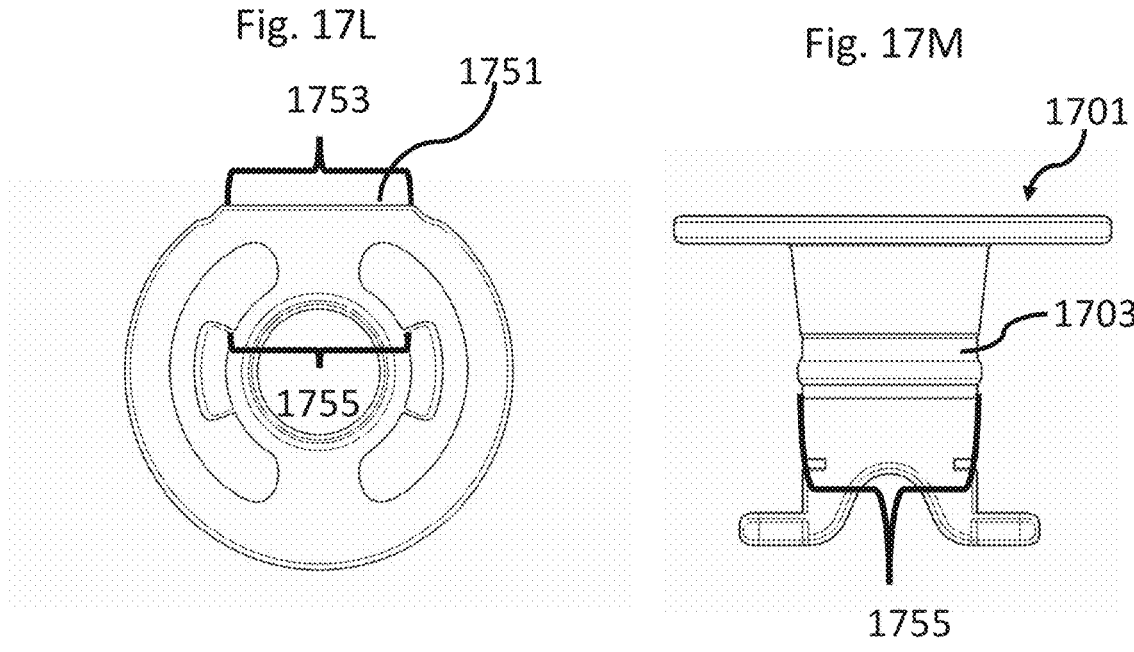

1902

1908

1904

1912   1910   1906

1902

1908

1904

1906

1910

1912

LAPAROSCOPIC TISSUE CONTAINMENT DEVICE

RELATED APPLICATIONS

This application is a National Phase of PCT Patent Application No. PCT/IL2021/051499 having International filing date of Dec. 16, 2021, which claims the benefit of priority under 35 USC § 119(e) of U.S. Provisional Patent Application No. 63/126,640 filed on 17 Dec. 17, 2020. The contents of the above applications are all incorporated by reference as if fully set forth herein in their entirety.

FIELD AND BACKGROUND OF THE INVENTION

The present invention, in some embodiments thereof, relates to a laparoscopic tissue containment device, for example a laparoscopic workspace device, and, more particularly, but not exclusively, to an inflatable laparoscopic tissue containment device.

A workspace device, for example a laparoscopic tissue containment device, is used, for example to isolate a tissue and/or an organ from other body tissues within a body cavity, for example an abdominal cavity.

SUMMARY OF THE INVENTION

Some examples of some embodiments of the invention are listed below. It should be understood that features from one example can be used with features from other examples:

Example 1. A workspace device having a body which is collapsible to a collapsed state to fit through a laparoscopic passageway in a body cavity wall, and expandable to an expanded state within a body cavity into which said passageway extends, comprising:

a workspace body having a workspace wall including a plurality of expandable segments defining an internal lumen, and a plurality of radial rigidizers positioned within said wall;

wherein in said expanded state:

said workspace device extends defining a workspace axis, and has an opening to said internal volume; and said plurality of expandable segments rigidize said workspace body to resist collapse by intra-abdominal forces and said plurality of radially extending rigidizers positioned within said wall resist radial forces.

Example 2. A device according to example 1, wherein said workspace wall comprises at least one inflatable chamber comprising said radial rigidizers, and wherein said radial rigidizers divide said inflatable chamber into said plurality of expandable segments which are fluidically connected to each other.

Example 3. A device according to any one of examples 1 or 2, wherein in said expanded state said radial rigidizers are smaller than a width of said workspace wall.

Example 4. A device according to example 1, wherein in an expanded state, adjacent expandable segments laterally press at least one radial rigidizer of said plurality of radially rigidizers.

Example 5. A device according to any one of the previous examples, wherein said workspace wall comprises at least one inner layer of sheet material forming said inner surface facing in an expanded state the internal lumen of the workspace device, and at least one outer layer of sheet material forming said outer surface of said workspace wall, and wherein said two or more radial rigidizers interconnect said at least one inner layer and said at least one outer layer.

Example 6. A device according to example 5, wherein said plurality of radial rigidizers are formed by said at least one inner layer of sheet material and/or by said at least one outer layer of sheet material.

Example 7. A device according to example 6, wherein said radial rigidizers comprise portions of the at least one inner layer and/or portions of the at least one outer layer.

Example 8. A device according to any one of examples 5 to 7, comprising at least one additional bendable layer of sheet material attached to said inner layer and said outer layer to form said plurality of radial rigidizers.

Example 9. A device according to any one of examples 5 to 8, wherein said expandable segments are separated by at least one radial rigidizer of said plurality of radial rigidizers, and wherein a length of a radial rigidizer positioned between two adjacent expandable segments is at least 2 cm.

Example 10. A device according to any one of examples 5 to 9, wherein each of said radial rigidizers define a sidewall of at least one expandable segment of said plurality of expandable segments.

Example 11. A device according to any one of examples 5 to 10, wherein in an expanded state, two adjacent expandable segments are pressed against each other along an interface region having a length larger than 0.3 cm.

Example 12. A device according to any one of examples 5 to 11, wherein in an expanded state, said at least one inner layer and said at least one outer layer are smooth.

Example 13. A device according to example 12, wherein in an expanded state, said at least one inner layer and said at least one outer layer comprise one or more bulges that have a radius of curvature which is smaller than 10 mm.

Example 14. A device according to any one of examples 5 to 11, wherein in an expanded state, one of said at least one inner layer and said at least one outer layer is smoother than the other layer.

Example 15. A device according to any one of examples 5 to 11, wherein, in an expanded state, said at least one inner layer is smoother than said at least one outer layer, and wherein said expandable segments extend radially outwardly to a distance larger than 2 cm from said internal lumen.

Example 16. A device according to any one of examples 5 to 11, wherein, in an expanded state, said at least one outer layer is smoother than said at least one inner layer, and wherein said expandable segments extend radially inwardly into said at least one internal lumen of said workspace device to a distance larger than 2 cm from said at least one outer layer.

Example 17. A device according to any one of examples 5 to 16, wherein in an expanded state, said radial rigidizers are perpendicular to a tangent of at least one or both of said at least one inner layer and said at least one outer layer.

Example 18. A device according to any one of examples 5 to 16, wherein in an expanded state, said radial rigidizers are positioned at an angle relative to a tangent of at least one or both of said at least one inner layer and said at least one outer layer.

Example 19. A device according to any one of examples 1 to 5, wherein said expandable segments are ring-shaped expandable segments surrounding said internal lumen and arranged along said workspace axis, wherein an interface region between two adjacent ring-shaped expandable segments comprise at least one radial rigidizer of said plurality of radial rigidizers.

Example 20. A device according to example 19, wherein in an expanded state, a height of each of said ring-shaped expandable segments is shorter than a length of said interface region between adjacent ring-shaped expandable segments.

Example 21. A device according to any one of the previous examples, comprising one or more inflation channels shaped to supply inflation fluid to said workspace device body and to said expandable segments to expand said workspace body to said expanded state.

Example 22. A device according to any one of the previous examples, comprising one or more visualization channels in said workspace body penetrating at least 1 cm into said internal lumen through an opening in an outer surface of said body; wherein said one or more visualization channels are sized to receive an end of a visualization tool.

Example 23. A device according to example 22, wherein a minimal diameter of said one or more visualization channels is at least 5 mm.

Example 24. A device according to example 22, wherein an end of said one or more visualization channels within said internal lumen is closed, and wherein said one or more visualization channels is at least partly transparent to allow visualization of said internal volume from a close distance by said visualization tool.

Example 25. A device according to any one of examples 22 to 24, wherein said one or more visualization channels penetrate into said internal lumen through an opening in said workspace wall located between expandable segments, or within an expandable segment.

Example 26. A device according to any one of examples 22 to 24, wherein said one or more visualization channels penetrate into said internal lumen through an opening within at least one radial rigidizer or between two adjacent radial rigidizers of said plurality of radial rigidizers.

Example 27. A device according to any one of examples 22 to 24, comprising a tool insertion channel connecting in an expanded state said opening of said workspace device with a body opening, and wherein said one or more visualization channels penetrate into said internal lumen through an opening in said tool insertion channel.

Example 28. A device according to any one of the previous examples, wherein said passageway is smaller than 15 mm, and wherein said workspace device fits in a collapsed state inside said passageway.

Example 29. A device according to any one of the previous examples, wherein in said expanded state said workspace device extends axially from a proximal to a distal direction defining said workspace axis.

Example 30. A device according to example 29, wherein said expandable segments are vertical expandable segments oriented along said workspace axis and arranged around a circumference of said internal lumen.

Example 31. A device according to any one of examples 1 to 29, wherein in said expanded state said workspace device extends laterally, and wherein said opening to said internal lumen is an opening in said workspace wall.

Example 32. A device according to example 31, wherein said opening is an opening within one or more expandable segments or between expandable segments.

Example 33. A device according to any one of the previous examples, wherein said body cavity comprises an abdominal cavity, and wherein said body cavity wall comprises an abdominal cavity wall.

Example 34. A workspace device having a body which is collapsible to a collapsed state to fit through a laparoscopic passageway in a body cavity wall, and expandable to an expanded state within a body cavity into which said passageway extends, comprising:

a workspace body having a workspace wall including a plurality of expandable segments defining an internal lumen;

wherein in said expanded state:

said workspace device extends defining a workspace axis, and has an opening to said internal volume;

said plurality of expandable segments contact each other along an interface region having a length of at least 2 cm, formed between two adjacent expandable segments, and wherein said plurality of expandable segments extend inwardly into said internal lumen or outwardly to a distance larger than 2 cm from an opposite smooth surface of said wall, and rigidize said workspace body to resist collapse by intra-abdominal forces.

Example 35. A device according to example 34, wherein said workspace wall comprises an inflatable chamber comprising said expandable segments, and wherein said expandable segments are fluidically connected to each other within said inflatable chamber.

Example 36. A device according to any one of examples 34 or 35, wherein in said expanded state said workspace device extends axially from a proximal to a distal direction defining said workspace axis, and wherein said expandable segments are vertical expandable segments oriented along said workspace axis and arranged around a circumference of said internal lumen.

Example 37. A device according to any one of examples 34 to 36, wherein in an expanded state, an outer surface of said workspace body is smoother than an inner surface of said body, and wherein said expandable segments extend inwardly into said internal volume.

Example 38. A device according to any one of examples 34 to 36, wherein in an expanded state, an inner surface of said workspace body is smoother than an outer surface of said body, and wherein said expandable segments extend outwardly from said internal volume.

Example 39. A device according to any one of examples 34 to 38, wherein said workspace wall comprises at least one inner layer of sheet material and at least one outer layer of sheet material, attached to each other to form said expandable segments therebetween.

Example 40. A device according to example 39, comprises a plurality of ribs, and wherein said at least one inner layer and said at least one outer layer are attached to said plurality of ribs, wherein at least one rib of said plurality of ribs forms said interface region adjacent expandable segments.

Example 41. A device according to any one of examples 34 to 40, wherein said passageway is smaller than 15 mm, and wherein said workspace device fits in a collapsed state inside said passageway.

Example 42. A device according to any one of examples 34 to 41, wherein said body cavity comprises an abdominal cavity, and wherein said body cavity wall comprises an abdominal cavity wall.

Example 43. A workspace device having a body which is collapsible to a collapsed state to fit through a laparoscopic passageway in a body cavity wall, and expandable to an expanded state within a body cavity into which said passageway extends, comprising:

a workspace body comprising an expandable workspace wall defining an internal lumen; wherein said workspace body is expandable to increase said internal volume to an expanded state within said body cavity by expansion of said expandable wall;

one or more visualization channels having an opening in said workspace body shaped to receive a visualization tool;

wherein in said expanded state said one or more visualization channels penetrates to a distance larger than 1 cm from an internal surface of said workspace body facing said internal lumen, into said internal lumen.

Example 44. A device according to example 43, wherein an end of said one or more visualization channels located within said internal lumen is closed, and wherein said one or more visualization channels is at least partly transparent.

Example 45. A device according to any one of examples 43 or 44, wherein said workspace device body comprises a tool insertion channel connecting in an expanded state an opening of said workspace device with a body opening in said body cavity wall, and wherein said one or more visualization channels penetrate into said internal lumen through an opening in said tool insertion channel.

Example 46. A device according to any one of examples 43 or 44, wherein said one or more visualization channels penetrate into said internal lumen through an opening in said expandable wall.

Example 47. A device according to example 46, wherein said expandable wall comprises a plurality of expandable segments, and wherein said one or more visualization channels penetrate into said internal lumen through an opening in said expandable wall located between adjacent expandable segments.

Example 48. A device according to example 47, wherein said expandable wall comprises a plurality of radial rigidizers contacting and/or define said expandable segments, wherein two adjacent expandable segments are separated between at least one radial rigidizer; and wherein said one or more visualization channels penetrate into said internal lumen through an opening in said at least one radial rigidizer.

Example 49. A device according to any one of examples 43 to 48, wherein a minimal diameter of said one or more visualization channels is at least 5 mm.

Example 50. A workspace device having a body which is collapsible to a collapsed state to fit through a laparoscopic passageway in a body cavity wall, and expandable to an expanded state within a body cavity into which said passageway extends, comprising:

a workspace body having a workspace wall including a plurality of vertical expandable segments defining an internal volume;

wherein in said expanded state:

said workspace device extends axially from a proximal to a distal direction defining said workspace axis; and said plurality of vertical expandable segments are oriented along said workspace axis and rigidize said workspace body to resist collapse by intra-abdominal forces.

Example 51. A device according to example 50, wherein said workspace wall comprises at least one inflatable chamber comprising said plurality of vertical expandable segments, and wherein said plurality of vertical expandable segments are fluidically connected to each other.

Example 52. A body opening port, comprising:

a rim shaped and sized to contact an external surface of a skin surrounding a body opening; a flexible cylindrical body defining a channel, connected to said rim and configured to pass through said body opening into a body cavity;

a cylindrical tube slidable within said channel, wherein sliding of said cylindrical tube within said channel, anchors said port within said body opening.

Example 53. A port according to example 52, comprising:

an expandable anchor connected to said flexible cylindrical body configured to move between a collapsed and an expanded state, wherein in an expanded state said anchor expands and anchors said port within said body opening;

wherein sliding of said cylindrical tube within said flexible cylindrical body expands said anchor to an expanded state.

Example 54. A port according to example 52, wherein said flexible cylindrical body is at least partly folded when inserted through said body opening, and wherein sliding of said cylindrical tube within said flexible cylindrical body unfolds said flexible cylindrical body.

Example 55. A body opening port, comprising:

a rim shaped and sized to contact an external surface of a skin surrounding a body opening;

a cylindrical body insertable through said body opening into a body lumen, wherein said cylindrical body has a proximal end connected to said rim and a distal end positioned within said body;

an expandable anchor connected to said cylindrical body near said distal end, wherein said expandable anchor is configured to expand and anchor said port within said body opening, wherein said expandable anchor comprises an opening or a channel shaped to receive a visualization tool.

Example 56. A method for producing expandable segments of a workspace device expandable wall, comprising:

positioning a plurality of ribs between at least one first layer of sheet material and at least one second layer of sheet material;

welding said at least one first layer of sheet material and said at least one second layer of sheet material to two opposite ends of each rib of said plurality of ribs, to form expandable segments, wherein each expandable segment is formed between two adjacent ribs.

Example 57. A method according to example 56, wherein said positioning comprises aligning each rib of said plurality of ribs to be perpendicular to said at least one first layer and said at least one second layer or to be perpendicular to a tangent of said at least one first layer and a tangent of said at least one second layer, prior to said welding.

Example 58. A method according to example 56, wherein said positioning comprises aligning at least some of the plurality of ribs at an angle relative to a tangent of said at least one first layer and a tangent of said at least one second layer, prior to said welding.

Example 59. A method according to example 56, comprising:

shaping at least one or both of said at least one first layer and said at least one second layer, and wherein said positioning comprises positioning said plurality of ribs between one or both of said shaped at least one first layer and said at least one second layer.

Example 60. A body opening port, comprising:

a rim shaped and sized to contact an external surface of a tissue surrounding a body opening; a tubular body insertable through said body opening into a body lumen, wherein said tubular body defines an inner lumen, has a proximal end connected to said rim and a distal end positioned within said body;

an inner expandable anchor connected to said tubular body at said distal end, wherein said expandable anchor is configured to expand and anchor said port within said body opening.

Example 61. A port according to example 60, wherein said inner expandable anchor comprising at least two wings configured to move between a collapsed state in which the at least two wings face each other and an expanded state in which the at least two wings laterally extend from the tubular body, wherein said two wings are configured to laterally extend when the inner expandable anchor is in a relaxed state.

Example 62. A port according to example 61 wherein said at least two wings are positioned at opposite sides of the tubular body, and wherein in a collapsed state said inner expandable anchor bends inwardly towards said inner lumen to position said at least two wings at a distance of less than 2 cm from each other.

Example 63. A port according to example 62, wherein said tubular body comprises at least two slot cuts at said distal end defining a bending axis therebetween along which said inner expandable anchor bends in said collapsed state, and wherein each of said slot cuts is positioned on a circumference and at opposite sides of said tubular body distal end between said at least two wings.

Example 64. A port according to any one of examples 61 to 63, wherein said tubular body comprises at least two openings, and wherein each opening of said at least two openings is positioned between each of said at least two wings and said tubular body proximal end.

Example 65. A port according to any one of examples 60 to 64, wherein said rim is part of an external bolster shaped and sized to contact an external surface of the skin, wherein said external bolster comprises a cutting guide having a length that matches a target incision length that needs to be performed in a skin in order to introduce said tubular body distal end into said body lumen.

Example 66. A port according to any one of examples 60 to 65, wherein said rim and said inner expandable anchor are integrated with said tubular body.

Example 67. A port according to any one of examples 60 to 66, wherein said body opening port is elastic.

Example 68. A port according to any one of examples 60 to 67, wherein said inner expandable anchor comprises an opening or a channel shaped to receive a visualization tool.

Example 69. An introducer of a laparoscopic workspace device, comprising:

an elongated external tubular body having an inner lumen with a distal opening and a proximal opening;

an internal member shaped and sized to slide within said inner lumen and to extend out through said distal opening, comprising:

an elongated body having a distal end and a proximal end;

an expandable workspace device holder coupled to said elongated body distal end, and configured to move between an expanded state when said holder extends out from said inner lumen, and a collapsed state when said holder is positioned within said inner lumen;

wherein said expandable workspace device holder comprises at least two elastic members coupled to each other by at least one rigid spacer configured to keep said at least two elastic members at a desired distance between each other when said holder is in a collapsed state within said inner lumen.

Example 70. An introducer according to example 69, wherein said at least two elastic members are coupled to said elongated body distal end via at least two spaced-apart hinge connectors configured to allow rotational movement of each of said at least two elastic members relative to said elongated body distal end when said expandable workspace device holder expands.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL
VIEWS OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the Drawings:

FIGS. 2A and 2B are schematic illustrations of a laparoscopic workspace device having a wall formed from two layers of sheet material where a length of an outer layer is larger from a length of an inner layer, according to some exemplary embodiments of the invention;

FIG. 2C is a schematic illustration showing the layers of FIGS. 2A and 2B interconnected by a plurality of ribs, in an unfolded state, according to some exemplary embodiments of the invention;

FIGS. 5A and 5B are schematic illustrations of a laparoscopic workspace device in an expanded state where a wall of the device is formed from circumferential expandable segments separated by rigidizing discs, according to some exemplary embodiments of the invention;

FIGS. 5C and 5D are schematic illustrations of rigidizing discs, according to some exemplary embodiments of the invention;

FIG. 7A is a schematic illustration showing a wall of a laparoscopic workspace device formed from two layers of sheet material in an unfolded state interconnected by axial elongated ribs, according to some exemplary embodiments of the invention;

FIGS. 7B-7D are schematic illustrations showing the formation of a laparoscopic workspace device from the wall of FIG. 7A, according to some exemplary embodiments of the invention;

FIGS. 8A and 8B are schematic illustrations showing a laparoscopic workspace device having a wall formed from circumferential rings separated by a radial rigidizer, according to some exemplary embodiments of the invention;

FIGS. 8C and 8D are schematic illustrations showing ratio between a height of an expandable segment and a length of a radial rigidizer located between adjacent expandable segments, according to some exemplary embodiments of the invention;

FIGS. 9A-9C are schematic illustrations of a laparoscopic workspace device having a wall that includes outwardly extending vertical expendable segments, according to some exemplary embodiments of the invention;

FIGS. 13A-13C are schematic illustrations of a laparoscopic workspace device formed from vertical and horizontal expandable segments, according to some exemplary embodiments of the invention;

FIGS. 16A-16C are schematic illustrations of a port formed from overlapping portions, according to some exemplary embodiments of the invention;

FIGS. 17D-17F are schematic illustrations of a port having an expandable distal end, according to some exemplary embodiments of the invention;

FIGS. 17J-17M are schematic illustrations of a port having a cutting guide, according to some exemplary embodiments of the invention;

DESCRIPTION OF SPECIFIC EMBODIMENTS OF THE INVENTION

Figure 1A:
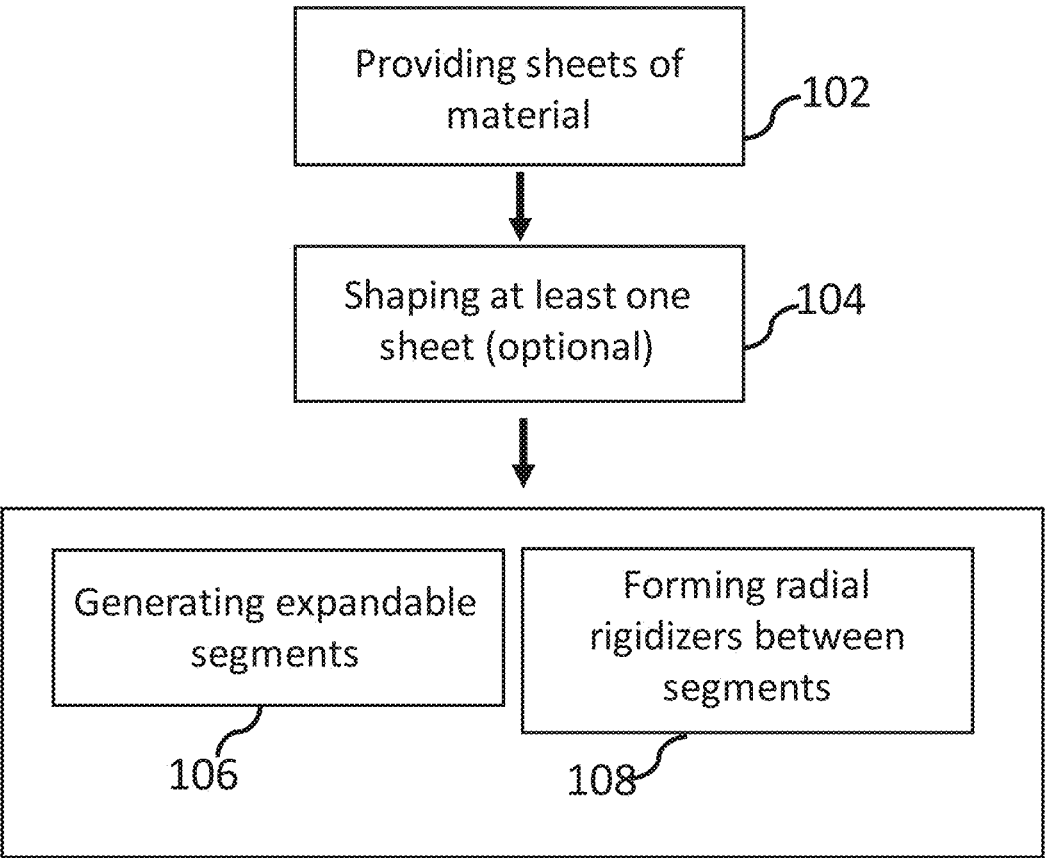
FIG. 1A is a general process for forming expandable segments of a workspace device having a radial rigidizer, according to some exemplary embodiments of the invention.

The present invention, in some embodiments thereof, relates to a laparoscopic tissue containment device and, more particularly, but not exclusively, to an inflatable laparoscopic tissue containment device.

Overview

A broad aspect of some embodiments of the invention relates to a workspace device, which may be inserted into the body (e.g., a body lumen such as the abdominal cavity) and used for processing body tissue therein, while inside the body, for example as described in WO2019/049152 incorporated herein as a reference in its entirety. In some embodiments, a body of the workspace device is formed from an expandable wall defining an internal lumen of the device, and includes a plurality of expandable segments, and one or more rigidizers, for example radially extending rigidizers, for example radial rigidizers. In some embodiments, the expandable wall comprises at least one inflatable chamber comprising the plurality of expandable segments and the radial rigidizers. Optionally, the radial rigidizers divide the at least one inflatable chamber into said plurality of expandable segments. Additionally or optionally, the plurality of expandable segments are fluidically connected to each other, for example to allow fluid flow between fluidically connected expandable segments of the inflatable chamber when the inflatable chamber is inflated. In some embodiments, the plurality of expandable segments allows, for example, to resist collapse of the device body by intra-abdominal forces caused for example by intra-abdominal gas used for insufflation. Additionally, the radial rigidizers allow, for example, to resist radial forces applied, for example on the outer surface of the expandable wall.

According to some embodiments, the body of the workspace device comprising the expandable wall is configured to collapse to a collapsed state, for example to fit through a laparoscopic passageway within a body cavity wall, for example an abdominal cavity wall. In some embodiments, the workspace device body is configured to collapse to fit within a laparoscopic passageway having an inner width smaller than 20 mm, for example smaller than 15 mm, smaller than 10 mm or any intermediate, smaller or larger width. As used herein, a laparoscopic passageway means any opening crossing through the body wall, including natural orifices, optionally used or formed in a laparoscopic surgical procedure.

According to some embodiments, the body of the workspace device comprising the expandable wall is configured to expand to an expanded state within a body cavity, for example an abdominal cavity, into which the laparoscopic passageway extends from a body opening of the body cavity wall.

According to some embodiments, one or both of an inner surface and an outer surface of the expandable wall are smooth, when the workspace device body is in an expanded state. In some embodiments, the term "smooth" refers to a surface, which is optionally curved, having a surface texture that contain bulges that have a radius of curvature smaller than 0.1 mm, for example smaller than 0.05 mm, smaller than 0.01 mm or any intermediate, smaller or larger value.

Alternatively or additionally, the term "smooth" in some embodiments, refers to a surface, which is optionally curved, having elements that have a radius of curvature smaller than 2 cm, for example smaller than 1 cm, smaller than 0.5 cm, or any intermediate, smaller or larger value. Alternatively or additionally, the term "smooth", in some embodiments, relates to a surface, which is optionally curved, that optionally contain bulges or other elements extending from the surface that have a radius of curvature which is smaller than 20%, for example smaller than 10%, smaller than 5%, smaller than 1% or any intermediate, smaller or larger percentage value, from a thickness of the expandable wall in an expanded state.

According to some exemplary embodiments, a wall, for example an expandable wall of the workspace device is fluidically connected to one or more inflation channels or tubes, configured to inflate at least one inflatable chamber within the wall. Alternatively or additionally, the one or more inflation channels or tube are configured to inflate at least one, for example two or more expandable segments of the wall.

An aspect of some embodiments relates to a wall of a workspace device, for example a laparoscopic workspace device comprising at least one expandable segment, for example 2, 3, 4 or any larger number of expandable segments. In some embodiments, the wall of the workspace device comprises two or more radial rigidizers. It should be appreciated that "rigid" does not mean hard. Rather, it means stiff enough to resist radial forces applied on the body of the workspace device, optionally expected during an operation, for example, the radial rigidizers may be stiff enough to maintain a shape of the device body with less than 10% change in volume in an ambient environment with a pressure above the device pressure, for example the pressure within an internal lumen of the device used for processing tissue, such as 5 mmHg, 10 mmHg, 20 mmHg, 30 mmHg or intermediate or higher pressure. In some embodiments, the two or more radial rigidizers are configured to increase the stiffness of the wall to resist radial pressure within an insufflated body cavity.

According to some embodiments, at least some of the radial rigidizers are optionally located adjacent or between expandable segments forming the wall. In some embodiments, at least some of the radial rigidizers are optionally positioned within expandable segments. In some embodiments, at least some of the radial rigidizers comprise spaced apart elements not connected to each other. Alternatively, at least some of the radial rigidizers comprise spaced apart elements connected to each other, for example by at least one connecting portion. In some embodiments, at least some of the radial rigidizers and connecting portions are integrated in a layer of sheet material. In some embodiments, at least some of the radial rigidizers are part of one or more layers forming expandable segments of a wall. In some embodiments, at least some or all radial rigidizers are perforated, for example to allow fluid flow between adjacent expandable segments separated by the radial rigidizer. Alternatively, at least some of the radial rigidizers are sealed, for example to maintain structural integrity of the wall in case one or more of the expandable segments contacting the radial rigidizer is penetrated.

According to some embodiments, the radial rigidizers comprise ribs, for example thin rib. In some embodiments, the ribs have a thickness in a range of 20-150 micron ($\mu$m), for example 20-50 $\mu$m, 40-80 $\mu$m, 70-120 $\mu$m or any intermediate, smaller or larger range of values, are positioned between adjacent expandable segments of the wall. In some embodiments, one or more of the ribs define an expandable segment. Optionally, a single rib is shared by two adjacent expandable segments of the wall. In some embodiments, each rib is welded to at least one inner layer of sheet material and to at least one outer layer of sheet material, for example to form at least one expandable segment. Optionally, at least some or all of the expandable segments are defined by at least two ribs welded to the at least one inner layer and to the at least one outer layer.

According to some exemplary embodiments, at least some or all of the ribs of a workspace device wall are fluidically sealed, for example to generate expandable segments that are sealed to fluid flow between each other. Alternatively, at least some or all of the ribs of a workspace device wall are perforated, for example to allow fluid flow between adjacent expandable segments. In some embodiments, the ribs are rigid, for example in a radial direction.

According to some exemplary embodiments, at least some or all of the ribs of a workspace device wall are spaced apart. Alternatively, the ribs are connected to each other. In some embodiments, the ribs of workspace device wall are formed from a preshaped single layer of sheet material. In some embodiments, in an expanded state of the wall, at least some or all of the ribs are perpendicular to a tangent of the inner layer and/or to a tangent of said outer layer. Alternatively, in an expanded state of the wall, the ribs are positioned at an angle relative to the inner layer and the outer layer of the wall.

According to some exemplary embodiments, the ribs comprise rings positioned between circumferential expandable segments surrounding an internal volume of a workspace device. Alternatively, the rings divide a lumen between an inner layer and an outer layer of a workspace device wall into circumferential expandable segments. Optionally, the ring-shaped rings are perforated, to allow for example fluid flow between adjacent expandable segments.

According to some exemplary embodiments, expandable segments of the wall are formed from at least one bended layer of sheet material, preshaped to form walls of expandable segments. In some embodiments, bended portions of the at least one bended layer which form the walls are radial rigidizers. Alternatively, radial rigidizers between adjacent expandable segments are formed by attaching walls of adjacent expandable segments, for example by welding or gluing of the walls.

According to some exemplary embodiments, ribs connected to at least one inner layer and at least one outer layer, define vertical expandable segments of a workspace device wall. In some embodiments, when expanded, the vertical expandable segments are positioned around an internal lumen of the workspace device. Alternatively, ribs connected to at least one inner layer and at least one outer layer, define circumferential expandable segments. In some embodiments, when expanded, the circumferential expandable segments surround an internal volume of the workspace device.

An aspect of some embodiments relates to a workspace device having a wall with extendable expandable segments, for example inwardly or outwardly extending expandable segments. In some embodiments, in an expanded state, for example when the extendable expandable segments are inflated, the extendable expandable segments are pressed against each other. In some embodiments, the extendable expandable segments are pressed against each other to define and expand an internal lumen of the workspace device.

According to some embodiments, walls of adjacent extendable expandable segments are optionally attached to each other, for example by welding, to form radial rigidizers when expanded. In some embodiments, a length of each radial rigidizer is larger than 50%, for example larger than 60%, larger than 80%, larger than 90% or any intermediate, smaller or larger percentage value from a thickness of the wall.

According to some exemplary embodiments, a workspace device wall comprises at least one smooth curved surface, and at least one wavy surface formed by the extendable expandable segments.

According to some embodiments, a workspace device comprises a wall having inwardly extending expandable segments. In some embodiments, a wall of the workspace device has an outer smooth surface, and an inner wavy surface formed by the inwardly extending expandable segments. In some embodiments, when expanded, the inwardly extending expandable segments extend into an internal lumen of the workspace device. Optionally, in an expanded state, each of the inwardly extending segments is pressed against adjacent inwardly extending segments.

According to some embodiments, a workspace device comprises a wall having outwardly extending expandable segments. In some embodiments, a wall of the workspace device has an inner smooth surface, and an outer wavy surface formed by the outwardly extending expandable segments. In some embodiments, when expanded, the outwardly extending expandable segments extend into a body cavity, for example an insufflated body cavity. Optionally, in an expanded state, each of the outwardly extending segments is pressed against adjacent outwardly extending segments.

According to some embodiments, expandable segments, for example the inwardly extending or the outwardly extending expandable segments are elongated vertical segments, that are optionally positioned around a circumference of the wall.

An aspect of some embodiments relates to anchoring a port configured to be positioned within a body opening, for example a surgical-formed body opening or an anatomical body opening, by moving at least one element through a channel defined by the port. In some embodiments, the at least one element comprises a surgical tool, for example a morcellator. Alternatively, the port comprises an outer portion and an inner portion slidable within the outer portion. In some embodiments, the port is anchored within the body opening by sliding the inner portion, for example a rigid portion within the outer portion, for example a flexible portion of the port. In some embodiments, the inner portion and the outer portions of the port are cylindrical.

According to some embodiments, sliding of the inner portion within an outer portion of the port already positioned within the body opening, expands an anchor. In some embodiments, the anchor is part of the outer portion of the port. Alternatively, the anchor is part of the inner portion of the port. In some embodiments, the anchor is reversibly expands, and is collapsed when the inner portion is removed from the outer portion of the port.

According to some embodiments, the outer portion of the port is introduced into the body opening in a folded state. In some embodiments, sliding of the inner portion within the outer portion unfolds the outer portion. In some embodiments, unfolding of the outer portion anchors the port within the body opening.

An aspect of some embodiments relates to visualizing an internal lumen of the workspace device from outside the body. In some embodiments, an expandable wall of the workspace device comprises one or more openings or channels which are shaped and sized to receive a visualizing tool, for example an end of an endoscope. In some embodiments, an end of the channels within the internal lumen is closed, for example to prevent penetration of the visualization tool through the expandable wall into the internal lumen. Additionally, at least part of the channel positioned within the internal lumen of the workspace device is transparent, for example to allow visualization of the internal lumen from within the channel.

According to some embodiments, a workspace device comprises one or more channels penetrating through an expandable wall or through a sleeve connecting the workspace device internal lumen and the body opening, into an internal lumen of the workspace device. In some embodiments, the one or more channels are open channels, for example to allow penetration of a visualizing tool, for example an endoscope into the internal lumen of the workspace device. Alternatively, an opening or an end of the one or more channels facing the internal lumen is closed, for example to maintain separation between the content in the internal lumen of the content of the body cavity.

According to some exemplary embodiments, the one or more openings or channels in the expandable wall is formed between adjacent radial rigidizers. Alternatively, the one or more opening or channel is formed within a radial rigidizer.

Alternatively or additionally, the internal lumen of the workspace device is visualized through an opening within a port positioned at a body opening and within an opening of the workspace device comprises at least one opening which is shaped and sized to receive the visualizing tool. In some embodiments, the openings is shaped and sized to allow penetration of a visualization tool into the internal lumen. Alternatively, the opening is an opening of a channel penetrating into that has at least one end.

An aspect of some embodiments relates to a workspace device having an expandable wall and a sleeve connecting a body opening and an internal lumen of the workspace device through the expandable wall. In some embodiments, the sleeve is connected to an opening in the expandable wall located between or through expandable segments of the wall. In some embodiments the sleeve is connected to one or more, for example two radial rigidizers of the expandable wall.

An aspect of some embodiments relates to a ribs aligner, configured to align a plurality of ribs with two or more layers of sheet material during the formation of a workspace device wall. In some embodiments, the ribs aligner fixes a position of the ribs when attaching the ribs to the at least two layers, for example when attaching each side of the rib to a different layer. In some embodiments the ribs aligner fixes a position of the ribs during the welding, for example radiofrequency (RF) welding, heat welding, or ultrasonic welding of the layers to the ribs.

According to some embodiments, the ribs aligner comprises a plurality of spaced apart spacers configured to hold, for example reversibly hold the ribs during the attachment, for example welding process. In some embodiments, a length of the spacers is determined according to a desired or preplanned distance between two layers forming a wall, for example a desired thickness of the wall. In some embodiments, a distance between adjacent spacers is determined according to a desired or preplanned distance between adjacent ribs of the wall. Optionally, a distance between adjacent ribs defines a size and/or volume of an expandable segment. In some embodiments, the spacers of the ribs aligner are electrically conductive.

According to some embodiments, a ribs aligner is planar, for example to allow attachment of at least one planar sheet, to the ribs. Alternatively, the ribs aligner is round, for example to allow attachment cylindrical sheets to the ribs.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

General Process for Forming a Wall of a Laparoscopic Workspace Device

Reference is now made to FIG. 1A depicting a process for forming a wall of a laparoscopic workspace device comprising one or a plurality of radial rigidizers, according to some exemplary embodiments of the invention.

According to some exemplary embodiments, two or more sheets of material are provided at block 102. In some embodiments, at least one of the sheets is flexible, for example formed from a flexible material. Optionally, at least one of the sheets is elastic, for example formed from an elastic material. In some embodiments, the sheets have a maximal thickness of 200 micron (μm), for example a maximal thickness of 100 μm, 50 μm, 10 μm or any intermediate, smaller or larger value.

According to some exemplary embodiments, at least one of the sheets is shaped, at block 104. In some embodiments, shaping of a sheet comprises bending or flexing of the sheet to a desired shape or pattern, for example a curved pattern or a wavy pattern. In some embodiments, the shaped sheet is fixed at the desired shape.

According to some exemplary embodiments, expandable segments are generated at block 106. In some embodiments, expandable segments, for example inflatable segments, are generated by connecting two or more of the provided sheets. In some embodiments, the two or more sheets are connected, for example welded, to each other at specific locations to form the expandable segments. In some embodiments, at least one of the sheets that was shaped at block 104 is connected to a smooth or flat sheet at specific location to form the expandable segments. Alternatively or additionally two shaped sheets are connected, for example welded, to each other to form the expandable segments.

According to some exemplary embodiments, radial rigidizers are formed between expandable segments, at block 108. In some embodiments, the radial rigidizers are formed between adjacent segments. In some embodiments, the radial rigidizers are formed during the generation of the expandable segments. Alternatively, the radial rigidizers are formed following the generation of the expandable segments.

According to some exemplary embodiments, the radial rigidizers are formed between adjacent expandable segments by attaching, for example welding, two opposite walls of adjacent expandable segments to each other, along a large surface area, to form a radial rigid interface. In some embodiments, the radial rigid interface has a length which is larger than a length of a wall of an expandable segment contacting the interface. In some embodiments, forming the interface between adjacent expandable segments from two or more sheet layers attached to each other rigidizes the interface, for example in a radial direction.

According to some exemplary embodiments, in an expanded state, two adjacent expandable segments are pressed against each other. In some embodiments, the two adjacent expandable segments are pressed against each other along an interface region having a length which is larger than 0.2 cm, for example larger than 0.2 cm, larger than 0.3 cm, larger than 0.5 cm, or any intermediate, smaller or larger value.

According to some exemplary embodiments, the radial rigidizers are formed by placing rigid ribs between two or more sheets, during the generation of the expandable segments. In some embodiments, connecting the two or more layers of sheets to the ribs, for example each layer to an opposite side of the ribs, forms the expandable segments. In some embodiments, when connecting the layers to the ribs, each expandable segment is defined by the two layers, and two ribs, where each rib separates between adjacent segments. In some embodiments, the expandable segments are generated at block 106 by welding two sheets to opposite sides of the ribs. In some embodiments, the two sheets are welded simultaneously or sequentially to the ribs.

Exemplary Wall with an Intermediate Layer

Figure 1B:
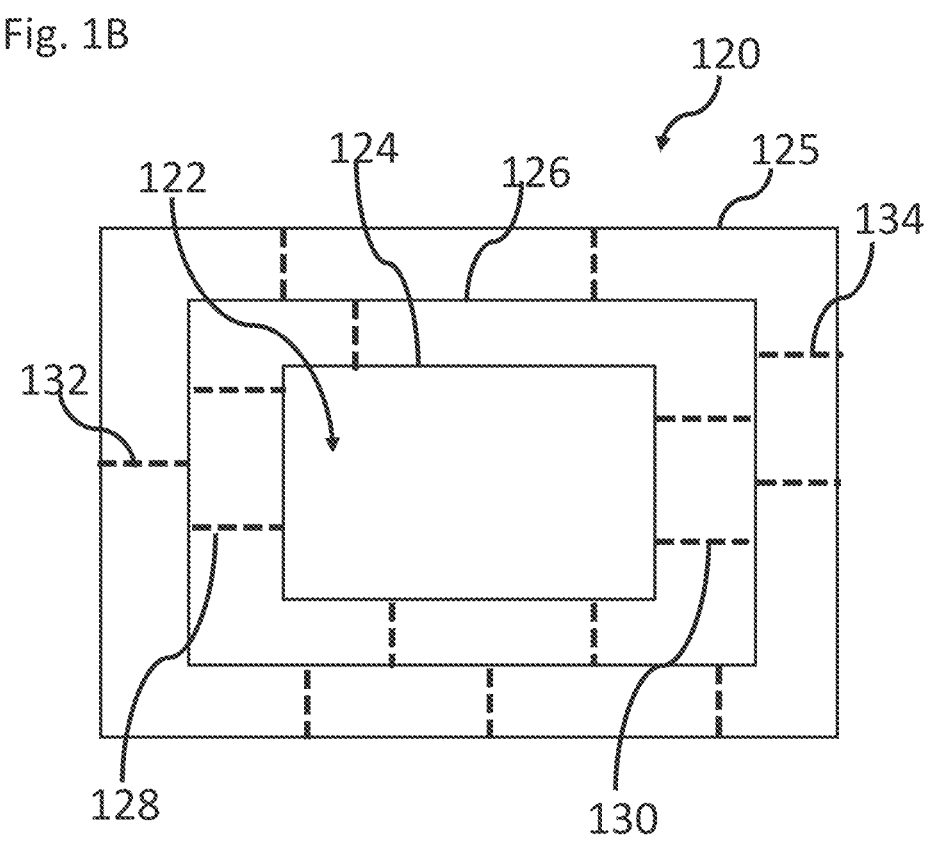
FIGS. 1B and 1C are schematic illustrations of workspace devices with radial rigidizers, according to some exemplary embodiments of the invention

According to some exemplary embodiments, a wall of a workspace device comprises one or more radial rigidizers, for example to resist inward collapse of the workspace device. In some embodiments, the one or more radial rigidizers are positioned between or adjacent to expandable segments of the wall. Optionally, the one or more radial rigidizers at least partly define one or more of the expandable segments. Reference is now made to FIG. 1B depicting radial rigidizers formed from a layer of sheet material within the wall, according to some exemplary embodiments of the invention.

According to some exemplary embodiments, a workspace device body comprises a wall, for example wall 120 which defines an internal lumen 122 of the device. In some embodiments, a wall of the workspace device comprises one or more expandable segments, that allow for example the workspace device body to move between a collapsed state when delivered into a body cavity, and to an expanded state when the device body is deployed within the body cavity. In some embodiments, during deployment of the workspace device, the one or more expandable segments are expanded, for example by inflation.

According to some exemplary embodiments, the wall 120 is formed from at least one inner layer 124, facing the internal lumen 122, and at least one outer layer 125, facing the body cavity. In some embodiments, at least one or both of the inner layer 124 and the outer layer are preshaped to acquire a selected shape or pattern, for example a curved or a wavy pattern. In some embodiments, at least one or both of the inner layer 124 and the outer layer 125 are formed from a flexible material that allows, for example, bending of the layers and/or wall in an expanded state.

Additionally, the wall comprises at least one intermediate layer of sheet material, for example intermediate layer 126, disposed between the inner layer 124 and the outer layer 125. In some embodiments, the intermediate layer 126 is connected, for example welded, to the inner layer 124 and to the outer layer 125 at specific locations, for example locations 128, 130, 132 and 134, to define a plurality of expandable segments.

According to some exemplary embodiments, when the expandable segments are expanded, a portion of the intermediate layer 126 connecting the inner layer 124 and the outer layer 125 forms a radial rigidizer portion. In some embodiments, the radial rigidizer portion is disposed between and contact two adjacent expandable segments. Optionally, a single radial rigidizer portion is shared and/or defines two adjacent expandable segments.

According to some exemplary embodiments, a connecting portion of the intermediate layer 126 to at least one of the inner layer 124 and the outer layer 125, has a length which is similar to a length of the radial rigidizer portion between the inner and outer layers. Alternatively, a length of the connecting portion of the intermediate layer 126 has a length which is larger than a length of the radial rigidizer portion extending between the inner and outer layers.

According to some exemplary embodiments, the intermediate layer 126 is preshaped, for example bended to a desired shape forming radial rigidizer portions and connecting portions, prior to connecting the intermediate layer 126 to the inner layer 124 and/or to the outer layer 125. In some embodiments, a thickness of the intermediate layer 124 is larger than the thickness of each or at least one of the inner layer 124 and the outer layer 125. Alternatively, radial rigidizer portions of the intermediate layer 126 are thicker than connecting portions of the intermediate layer. In some embodiments, a thickness of each layer is in a range of 0.2 µm-200 µm, for example 0.2 µm-10 µm, 8 µm-30 µm, 20 µm-70 µm, 100 µm-200 µm or any intermediate, smaller or larger range of values.

Exemplary Wall with Radial Rigidizers

Figure 1C:
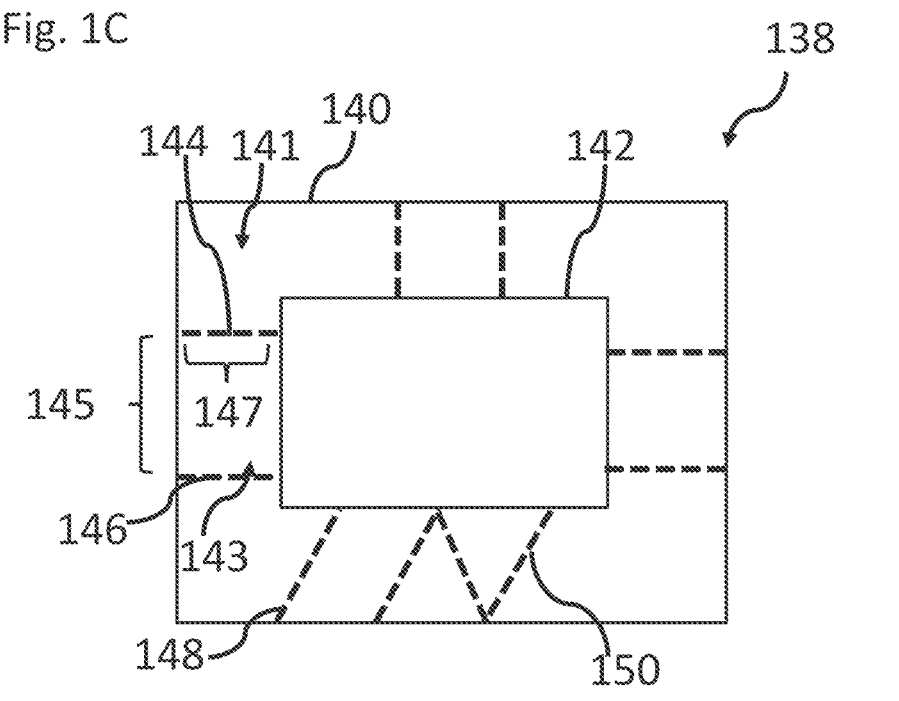

According to some exemplary embodiments, a wall of a workspace device is formed by an inner layer and an outer layer connected to each other. In some embodiments, the wall comprises a plurality of expandable segments defined by the inner and outer layers. In some embodiments, when the expandable segments expand, the connection portions between the expandable segments include radial rigidizers, that allow, for example, to resist collapse of the wall due to outside pressure in the body cavity in which the device is deployed. Reference is now made to FIG. 1C, depicting a wall of a workspace device which includes a plurality of radial rigidizers, according to some exemplary embodiments of the invention.

According to some exemplary embodiments, a wall of a workspace device, for example wall 138 comprises an inner layer 142 of sheet material, and an outer layer 140 of sheet material. In some embodiments, the inner layer 142 is connected to the outer layer 140 at specific locations, for example to define a plurality of expandable segments. In some embodiments, the plurality of expandable segments expand, for example upon inflation of the wall, when the device is deployed within a body cavity. In some embodiments, when the expandable segments are expanded the connection points between the two layers form radial rigidizers.

According to some exemplary embodiment, a radial rigidizer is formed between two adjacent expandable segments. In some embodiments, the radial rigidizer is formed by connecting walls of two adjacent expandable segments. In some embodiments, the two interconnected walls are two portions of the same layer, for example when at least one layer is bend or shaped to a curved or wavy pattern, that defines with a least one different layer, the expandable segments. In some embodiments, the expandable segments are formed from two preshaped layers, for example curved layers, connected to each other. Alternatively, at least one of the layers is curved and at least one different layer is smooth.

According to some exemplary embodiments, for example as shown in FIG. 1C, the at least one inner layer 142, and the at least one outer layer 140 are connected to each other with radial rigidizers, for example ribs 144, 146, 148, and 150. In some embodiments, each layer is connected to a different end of a rib. In some embodiments, a layer is connected to a rib by welding, gluing or using a solvent that dissolves one or both of the layer and the rib.

According to some exemplary embodiments, the ribs, or at least one rib, are more rigid in a radial direction when the expandable segments are expanded and/or when the workspace device is in an expanded state. In some embodiments, a thickness of each rib is larger than a thickness of each layer. In some embodiments, a maximal thickness of a rib is in a range of 0.2 μm-80 μm, for example 0.2 μm, 20 μm, 10 μm-30 μm, 15 μm-50 μm or any intermediate, smaller or larger range of values. In some embodiments, a rib, for example ribs 144, 146, 148 and 150 and/or one of the layers of sheet material are optionally formed from at least one of Polyurethane, Polyurethane with plastic coating, Fiber reinforced Nylon with Polyurethane coating, and Metallic film with Polyurethane layer adhered to it.

According to some exemplary embodiments, a distance 145 between two adjacent ribs, for example ribs 144 and 146, is determined, for example according to a distance 147 between an inner layer 142 and an outer layer 140. Alternatively, the distance 145 is determined according to a length of a rib, for example one or both of the ribs 144 and 146. In some embodiments, the distance 145 between two adjacent ribs is larger than a length of one or both of the ribs, for example ribs 144 and 146. In some embodiments, a distance between two adjacent ribs defines a length of an expandable segments. In some embodiments, a length of a rib defines a width or thickness of an expandable segment. A potential advantage of having distance 145 larger than a length of the rib may be to have an increased radial rigidity of the workspace wall.

According to some exemplary embodiments, a length of one or more of radial rigidizers, for example ribs 144 and 146 is optionally shorter from a thickness or an axial length, for example a length from a proximal end and a distal end of the wall 138, for example an expandable wall. In some embodiments, having radial rigidizers allows that are shorter than an axial length of the wall or the workspace device in an expanded state, allows, for example, fluid flow between two or more expandable segments of the wall. In some embodiments, a length of each radial rigidizer is at least 2 cm, for example at least 3 cm, at least 4 cm or any intermediate, smaller or larger length.

According to some exemplary embodiments, in an expanded state of a workspace device at least some of the ribs, or all of the ribs of a workspace device wall, for example ribs 144 and 146, are perpendicular to at least one of the inner layer 142 and the outer layer 140. Alternatively or additionally, at least some of the ribs, for example ribs 148 and 150, are positioned at an angle relative to the inner layer 142 and the outer layer 140.

According to some exemplary embodiments, in an expanded state of a workspace device, adjacent expandable segments, for example expandable segments 141 and 143, press against each other. In some embodiments, in an expanded state of a workspace device, the adjacent expandable segments press against a radial rigidizer, for example a rib positioned therebetween.

According to some exemplary embodiments, in an expanded state of a workspace device, at least one or both the inner layer and the outer layer of a workspace device are smooth. In some embodiments, at least one of the layers is curved, for example radially extends. In some embodiments, in an expanded state, at least one of the layers extends inwardly or outwardly.

According to some exemplary embodiments, in an expanded state, at least some expandable segments extend radially outwardly to a distance larger than 1 cm, for example larger than 2 cm, larger than 4 cm, larger than 5 cm, larger than 6 cm or any intermediate, smaller or larger value, from an internal lumen of the workspace device. Alternatively or additionally, in an expanded state, at least some expandable segments extend radially inwardly to a distance larger than 1 cm, for example larger than 2 cm, larger than 4 cm, larger than 5 cm, larger than 6 cm or any intermediate, smaller or larger value, into the internal lumen of the device. According to some exemplary embodiments, at least some or all of the radial rigidizers, for example ribs, are connected to each other. Alternatively, at least some or all of the ribs are disconnected from each other.

Exemplary Process for Generating a Ribs-Containing Wall of a Workspace Device

Figure 1D:
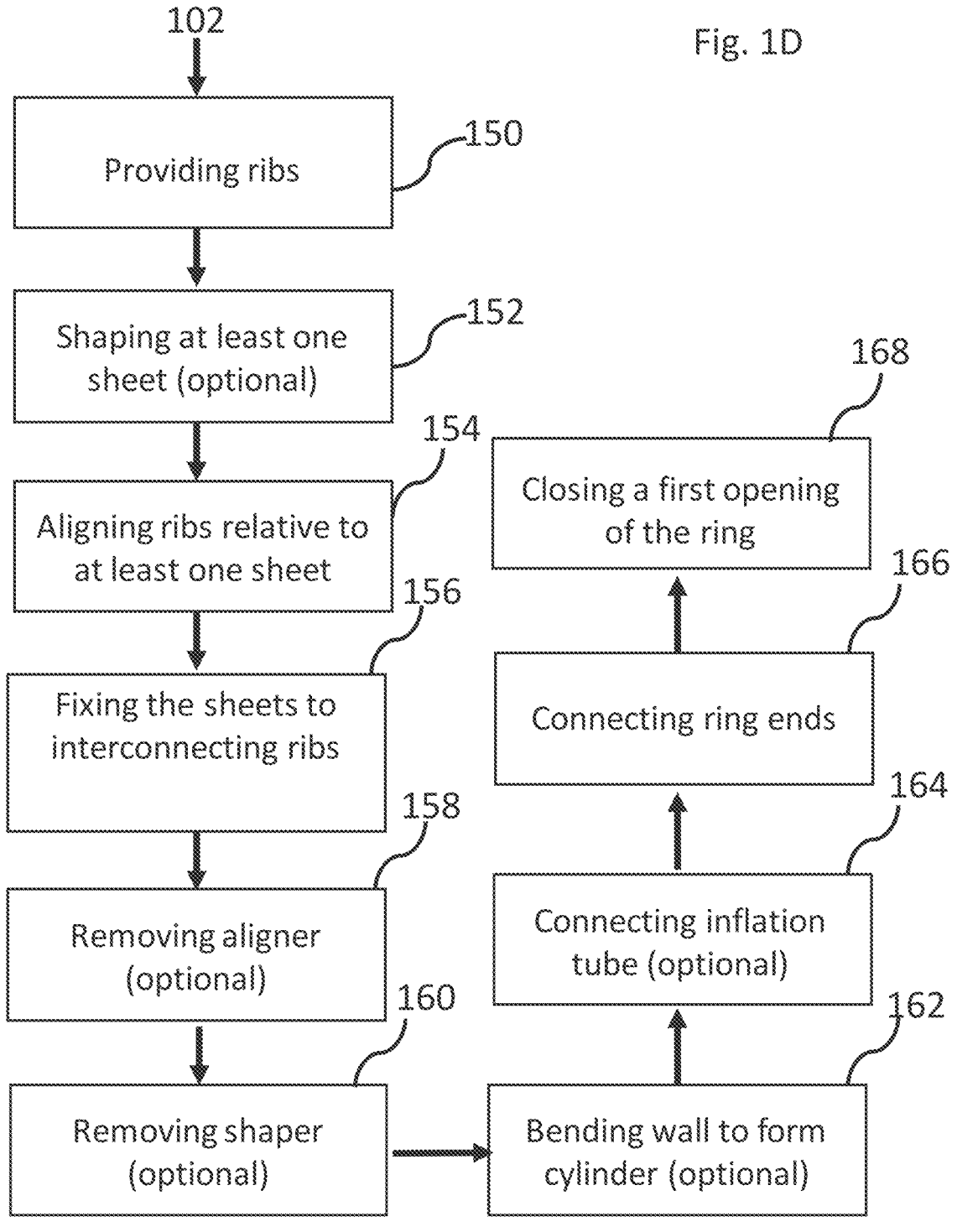
FIG. 1D is a detailed flow chart of a process for generating expandable segments with ribs therebetween, according to some exemplary embodiments of the invention.

According to some exemplary embodiments, a wall of a workspace device comprises a plurality of radial rigidizers, for example ribs. In some embodiments, the ribs are positioned between an inner layer and an outer layer of the wall. Optionally, the ribs are connected to both layers, for example to increase the rigidity of the wall against radial forces when the wall is expanded, and when the device is in an expanded state. Alternatively or additionally, the ribs allow, for example to distribute radial forces applied on the outer surface of the device, towards an inner surface and/or laterally towards other ribs. Reference is now made to FIG. 1D, depicting a process for generation of a wall of a workspace device which contains a plurality of ribs, according to some exemplary embodiments of the invention.

According to some exemplary embodiments, a plurality of radial rigidizer, for example ribs are provided at block 150. In some embodiments, the ribs are provided before, during, and/or after the providing of two or more sheets of material that will be used to form at least one inner layer, and at least one outer layer of the wall.

According to some exemplary embodiments, at least one of the sheets is preshaped to a desired shape or pattern, at block 152. In some embodiments, at least one of the sheets of material is bended or curved into the desired shape or pattern, for example into a wavy shape. Optionally, two sheets of material forming the inner and outer layer of a wall are preshaped to a desired shape or pattern. In some embodiments, the at least one of the sheets is preshaped using a shaper. In some embodiments, the shaper is configured to keep the at least one sheet in the desired shape before and during the fixation of the shaped sheet to a rib or to another sheet.

According to some exemplary embodiments, the ribs are aligned relative to one or more of the sheets, at block 154. In some embodiments, at least one or both of the sheets is aligned relative to the ribs. Optionally, at least one or both of the sheets is placed in contact with at least one or all of the ribs. In some embodiments, at least one or all of the ribs are aligned relative to one or more of the sheets using an aligner. In some embodiments, the aligner positions at least some of the ribs in a determined distance relative to each other. Alternatively or additionally, the aligner holds at least one of the ribs in a determined position relative to at least one sheet of material.

According to some exemplary embodiments, at least one of the sheets is fixed to at least one of the ribs, at block 156. In some embodiments, a rib is fixed simultaneously to two or more sheets, simultaneously or sequentially. In some embodiments, the at least one sheet is fixed to the at least one rib by welding, gluing or by solvent. In some embodiments, attaching the sheets of material to the ribs generated expandable segments of the wall. In some embodiments, adjacent expandable segments are separated by at least one rib.

According to some exemplary embodiments, the aligner is optionally removed at block 158.

According to some exemplary embodiments, the shaper is optionally removed at block 160.

According to some exemplary embodiments, the ribs and the at least two sheets of material, forming together a wall, are optionally bended at block 162. In some embodiments, the wall comprising the ribs and the sheets of material is bended to form a cylinder. Alternatively, the at least two sheets are provided as two closed cylinders, and the ribs are aligned relative to one or both of the cylinders at block 154.

According to some exemplary embodiments, at least one inflation tube is connected to the wall, at block 164. In some embodiments, the expandable segments of the formed wall are fluidically connected, and the at least one inflation tube is used to inflate all of the expandable segments of a wall. Alternatively, at least some of the expandable segments of the wall are fluidically connected, and two or more inflation tubes are connected to the wall.

According to some exemplary embodiments, two ends of the wall forming the cylinder, are connected to each other at block 166. In some embodiments, the two ends of the wall are connected, for example by welding or gluing, to each other to form an enclosed cylinder.

According to some exemplary embodiments, at least one opening of the enclosed cylinder is closed at block 168. In some embodiments, the at least one opening is closed to form a closed bottom of the workspace device. In some embodiments, the opening is closed with at least one additional layer.

Exemplary Workspace Device Having Smooth Inner and Outer Surfaces

Reference is now made to FIGS. 2A and 2B, depicting a workspace device having smooth inner and outer layers of sheet material connected at least partly by radial rigidizers, according to some exemplary embodiments of the invention.

According to some exemplary embodiments, a workspace device, for example device 200 comprises an expandable workspace device body 201 formed from a wall 203 having at least one expandable segment. In some embodiments, the wall 203 of the body defines an internal lumen, in which a body organ or a tissue is placed and optionally processed.

According to some exemplary embodiments, the body 201 comprises a distal base 210, formed from at least one layer. In some embodiments, the base 210 is formed from two or more layers. Optionally, the base 210 is expandable, for example by inflation of at least one expandable segments in the base.

According to some exemplary embodiments, the wall is formed from two or more layers of sheet material, for example at least one inner layer 202 and at least one outer layer 204. In some embodiments, the at least one inner layer 202 and the at least one outer layer 204 are interconnected by a plurality of radial rigidizers, for example ribs 208 and 209. In some embodiments, the ribs 208 and 209 divide a lumen between the two layers into two or more expandable segments. Optionally, at least some or all of the expandable segments are fluidically interconnected, for example to allow inflation of the expandable segments using a single inflation channel.

According to some exemplary embodiments, the body 201 comprises a channel 206, for example a cylindrical channel, comprising an opening 212, connected to the wall 203. In some embodiments, the channel is shaped and sized to be positioned within a body opening, and to define a sealed passageway between the internal lumen of the wall and body 203, and the outside of the body. In some embodiments, the passageway is sized an shape to allow, for example, insertion of tissue processing devices, for example a manual or an electric morcellator into the internal lumen of the body 203 from outside the body. In some embodiments, the channel 206 is flexible, and is optionally formed from one or more additional layers of sheet material. Alternatively, the channel is formed from an extension portion of one or more layers of sheet material used to form the wall 203, for example an extension portion of the inner layer 202 and/or an extension portion of the outer layer 204.

According to some exemplary embodiments, for example as shown in FIG. 2B, the body 201 comprises at least one inflation tube, for example inflation tube 211. In some embodiments, the inflation tube 211 is fluidically connected to the wall 203, for example to one or more expandable segments of the wall 203. Alternatively, the inflation tube 211 or at least one additional inflation tube is fluidically connected to the outer layer 204.

Reference is now made to FIG. 2C, depicting wall 203 in a pre-formed state, according to some exemplary embodiments of the invention.

According to some exemplary embodiments, wall 203 is formed from the inner layer 202 and outer layer 204. In some embodiments, for example as shown in FIG. 2C, a length of the outer layer 204 is larger than a length of the inner layer 202, when the layers are in an unfolded, preform state. In some embodiments, in an expanded state, for example as shown in FIGS. 2A and 2B, wall 203 has an outer circumference which is larger than an inner circumference, optionally due to the difference in length between the inner and outer layer. Additionally, for example as shown in FIG. 2C, the preformed inner and outer layers of sheet material are connected to each other by a plurality of spaced apart ribs, for example ribs connected to welding lines 208 and 209.

According to some exemplary embodiments, for example as shown in FIG. 2C, the channel 206, for example a tool insertion channel, is an integral part, for example an extending portion of the sheet material of the inner layer 202. In some embodiments, the extension portion is a portion of the inner layer 202 that extends beyond a portion of the inner layer 202 that is connected to the outer layer 204. Alternatively, the channel, for example the tool insertion channel, is an integral part of the outer layer sheet material. In some embodiments, the channel is a portion of the outer layer that extends beyond a portion of the outer layer connected to the inner layer.

Exemplary Radially Extending Rigidizers

According to some exemplary embodiments, radial rigidizers are connected, at least partly to at least one inner layer and at least one outer layer of an expandable wall of a workspace device. In some embodiments, radial rigidizers are configured to provide radial stiffness to a wall of a workspace device in an expanded state. Reference is now made to FIGS. 3A-3F, depicting different types of radial rigidizers, according to some exemplary embodiments of the invention.

Figure 3A:
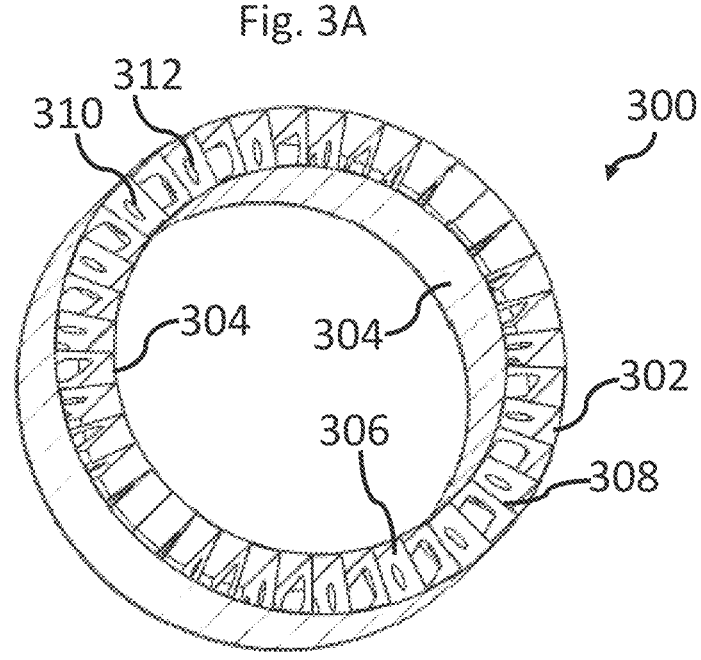
FIG. 3A is a schematic illustration showing a wall of a laparoscopic workspace device in an expanded state having perforated interconnecting radial ribs, according to some exemplary embodiments of the invention.

According to some exemplary embodiments, for example as shown in FIG. 3A, a wall 300 comprises at least one inner layer 304 of sheet material, and an outer layer 302 of a sheet material interconnected by a plurality of spaced apart ribs, for example ribs 306 and 308. In some embodiments, in an expanded state, for example as shown in FIG. 3A, the inner layer 304 and the outer layer 302 are smooth, for example do not comprise a protrusion, or an extension across and/or extending from a surface which is larger than 8 mm, for example larger than 7 mm, larger than 6 mm, larger than 4 mm or any intermediate, smaller or larger distance from a portion of the surface having a minimal diameter.

According to some exemplary embodiments, for example as shown in FIG. 3A, the radial rigidizers, for example the ribs, are perforated and include openings, for example openings 310 and 312. In some embodiments, the openings are large enough to allow, for example fluid pathways between different expandable segments of the wall. Additionally, the openings are small enough not to reduce the radial rigidity generated by the ribs. In some embodiments, a total area of openings in a single radial rigidizer, for example a rib, is up to 50%, for example up to 40%, up to 30%, up to 20% from the total surface area of the rib.

Figure 3B:
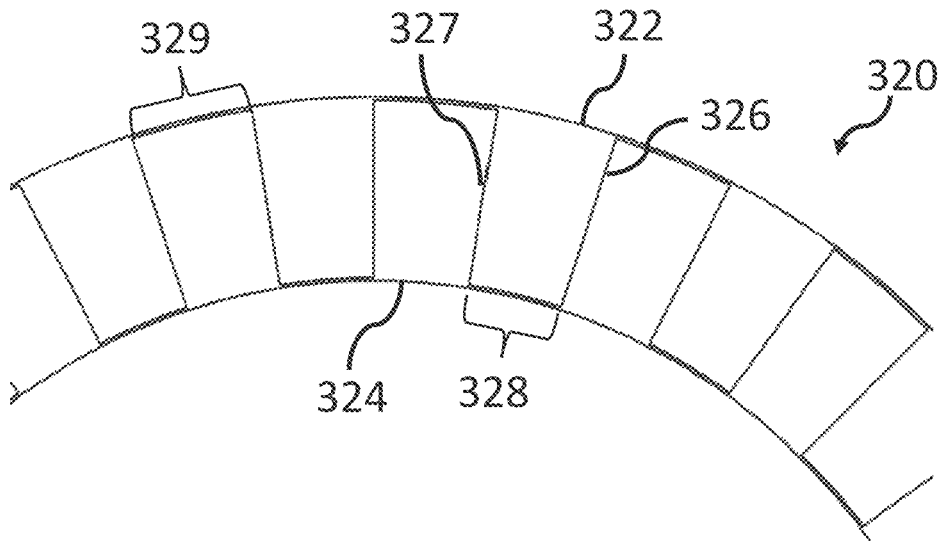
FIG. 3B is a schematic illustration showing a wall of a laparoscopic workspace device in an expanded state having interconnecting radial ribs formed from a single layer, according to some exemplary embodiments of the invention.

According to some exemplary embodiments, for example as shown in FIG. 3B, a wall, for example wall 320 comprises radial rigidizers, for example radial rigidizers 326 and 327 formed from at least one additional layer disposed between an inner layer 324 and an outer layer 322 of the wall 320. In some embodiments, the at least one additional layer is bended to form radially extending rigidizing portions 326 and 327 positioned at a radial direction, and connecting portions, for example connecting portions 328 and 329. In some embodiments, the connecting portions are portions where the at least one additional layer is attached, for example interchangeably, to the inner and outer layers. Optionally the connecting portions comprises openings, for example to reduce the amount of material needed to generate the connecting portions or a layer used to form the connecting portions.

According to some exemplary embodiments, radial rigidizer portions of the at least one additional layer are thicker and/or stiffer than the connecting portions of the at least one additional layer. In some embodiments, a length of a connecting portion attached to an inner layer or an outer layer, for example connecting portion 328 is similar or larger than a length of a radial rigidizer portion.

According to some exemplary embodiments, at least some or all of the radial rigidizer portions are solid. Optionally, the solid radial rigidizer portions define sealed expandable segments between adjacent radial rigidizer portions. Alternatively, at least some or all of the radial rigidizer portions are perforated, for example to generate expandable segments that are fluidically connected.

Figures 3C, 3D, 3E, 3F:
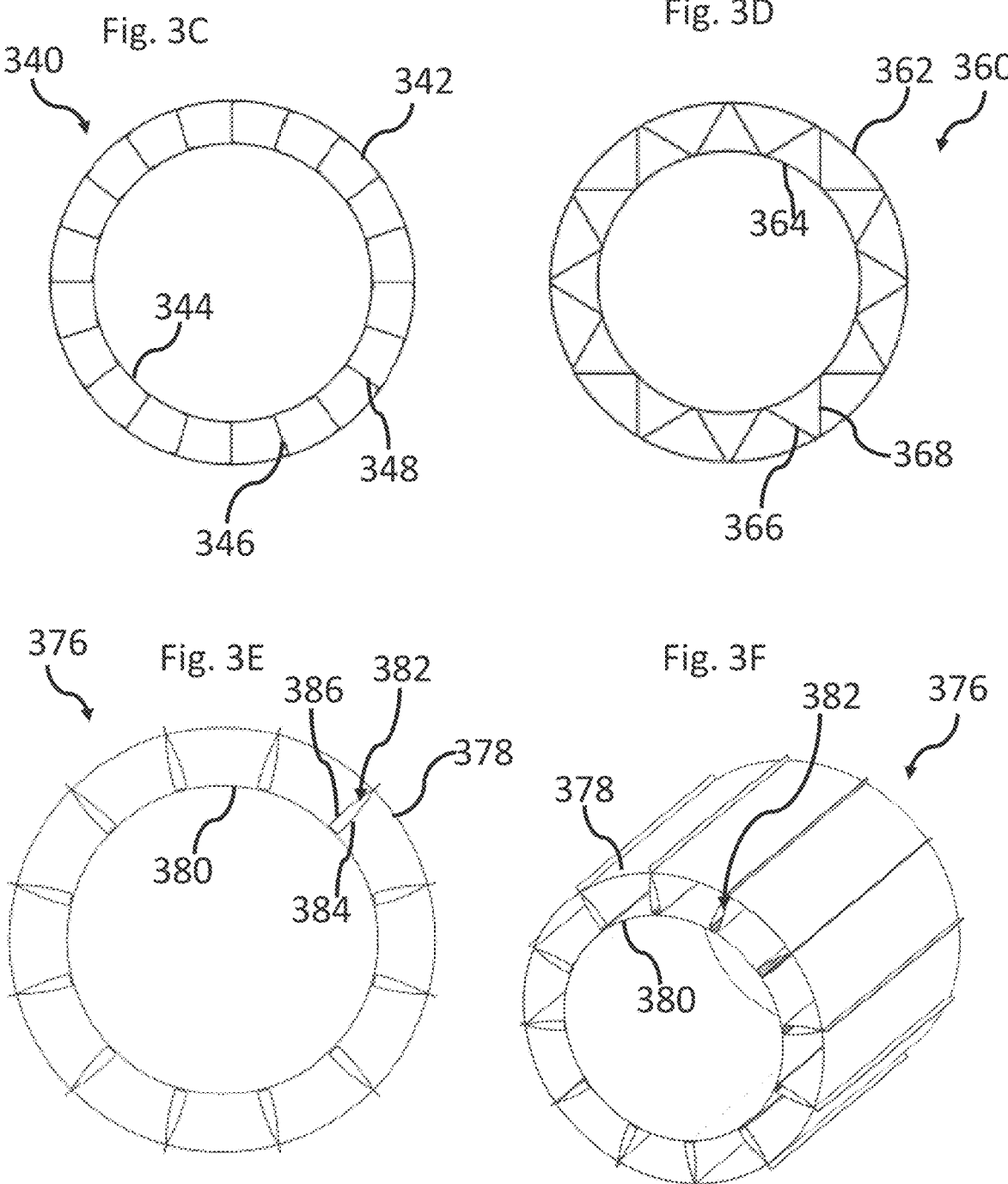
FIG. 3C is a schematic illustration showing a wall of a laparoscopic workspace device in an expanded state having interconnecting radial ribs perpendicular to layers forming the wall, according to some exemplary embodiments of the invention.
FIG. 3D is a schematic illustration showing a wall of a laparoscopic workspace device in an expanded state having interconnecting ribs positioned at an angle relative to layers forming the wall, according to some exemplary embodiments of the invention.
FIGS. 3E and 3F are schematic illustrations showing a wall of a laparoscopic workspace device in an expanded state having interconnecting radially extending ribs with spaced apart walls, according to some exemplary embodiments of the invention.

According to some exemplary embodiments, for example as shown in FIG. 3C, a wall 340 of a workspace device comprises an outer layer 342 and an inner layer 344 of sheet material interconnected by a plurality of radial rigidizers, for example radial rigidizer portions of at least one additional layer of sheet material or spaced apart ribs 346 and 348. In some embodiments, for example as shown in FIG. 3C, the plurality of radial rigidizers are perpendicular to the inner layer 344 and/or to the outer layer 342, when the wall 340 is in an expanded state, for example inflated. Optionally the radial rigidizers are radial to a longitudinal axis of the laparoscopic workspace device.

According to some exemplary embodiments, for example as shown in FIG. 3D, in wall 360 the plurality of radially extending rigidizers, for example rigidizers 366 and 368 are positioned at an angle relative to a tangent of the outer layer 362 and/or a tangent of the inner layer 364. In some embodiments, the plurality of rigidizers 366 and 368 are positioned at an angle, for example when the wall 360 is in an expanded state.

Reference is now made to FIGS. 3E and 3F, depicting a wall of a workspace device which includes a plurality of rigidizers formed from two or more walls, according to some exemplary embodiments of the invention.

According to some exemplary embodiments, a wall 376 of a workspace device, comprises an inner layer 380 of sheet material, and an outer layer 378 of sheet material, and a plurality of radial rigidizers, for example rib 382 positioned therebetween. In some embodiments, rib 382 is formed by bending at least one of the inner layer 380 or the outer layer 378. In some embodiments, a radial rigidizer formed by bending at least one of the layers is a double wall radial rigidizer. In some embodiments, the double wall radial rigidizer comprises an inner lumen. In some embodiments, a double wall radial rigidizer extends out from an outer layer 378 of the wall. In some embodiments, a double wall radial rigidizer extends out to a distance of up to 5 mm, for example up to 3 mm, up to 1 mm or any intermediate, smaller or larger distance from an external surface of the outer layer 378.

According to some exemplary embodiments, each radial rigidizer is formed from a tubular member. In some embodiments, two walls of the tubular member interconnect the inner layer and the outer layer, and are used as ribs between the inner layer and the outer layer. In some embodiments, each of the two additional walls of the tubular member interconnecting the two ribs are attached to a different layer of the inner layer and the outer layer, for example by welding. Optionally, at least some or each of the walls of the tubular member comprise openings. In some embodiments, during manufacturing, for example assembly of the expandable wall, the tubular member is positioned between the inner layer and the outer layer, and an electrode, for example a welding electrode is introduced into the lumen of the tubular member for welding each wall of the two additional walls to a different layer of the inner and outer layer. In some embodiments, two radial rigidizers are formed from a single tubular member, introduced between the inner layer and the outer layer. In some embodiments, each radial rigidizer is a wall of the tubular member.

Exemplary Workspace Device with a Wall Formed from Bending of Layers

Figures 4A, 4B:
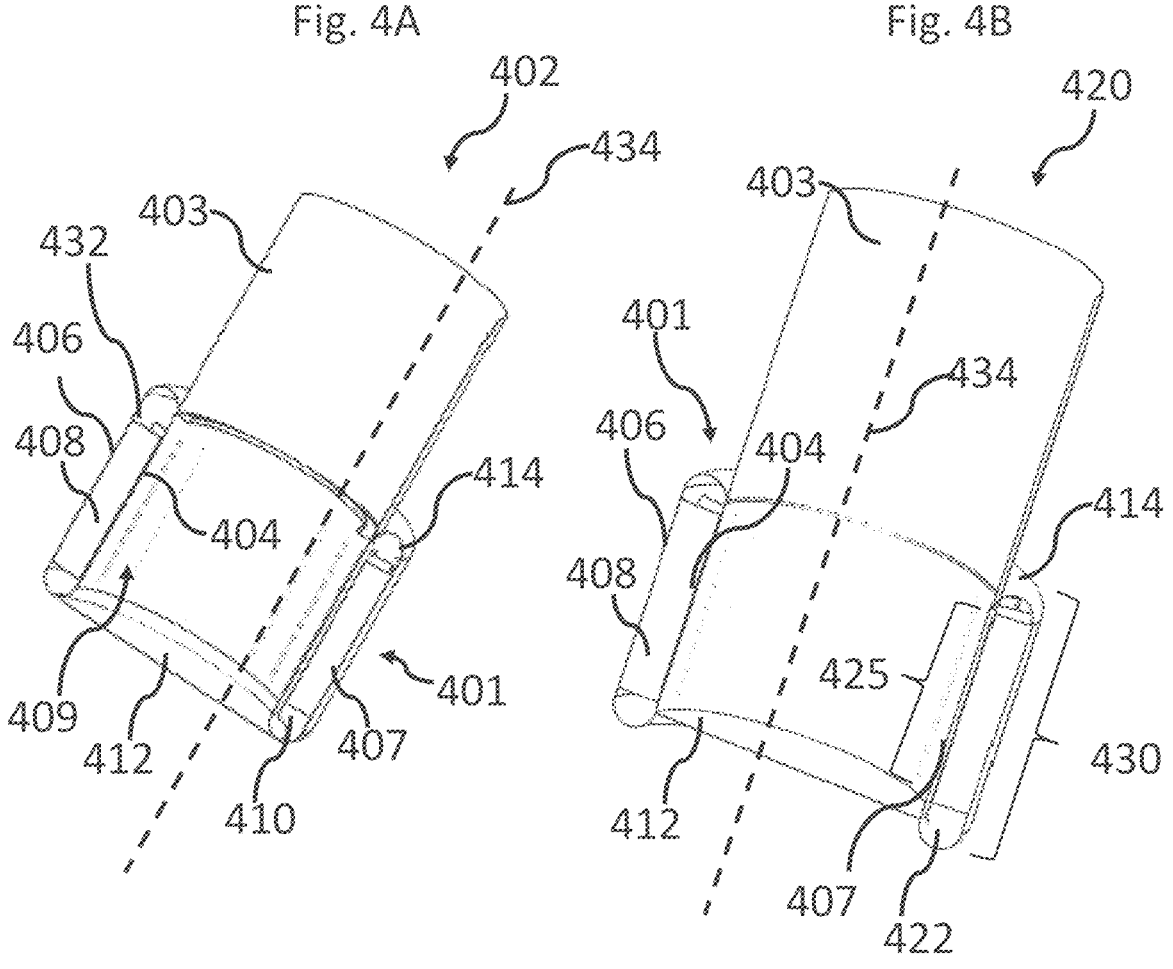
FIGS. 4A and 4B are schematic illustrations of a laparoscopic workspace device in an expanded state where a wall of the device comprises a plurality of ribs within an inflatable chamber, according to some exemplary embodiments of the invention.

Reference is now made to FIGS. 4A and 4B depicting cross-sections of a workspace device in an expanded state having a wall formed from bending of layers, according to some exemplary embodiments of the invention.

According to some exemplary embodiments, a workspace device 402 has a body configured to collapse and expand. Additionally, the workspace device body comprises a wall, for example an expandable wall 401. In some embodiments, the body of the workspace device is optionally collapsible to pass through a passageway, for example a laparoscopic passageway, through a body cavity wall into a body lumen. In some embodiments, the passageway comprises a channel connecting the outer surface of the skin, for example a body opening in the outer surface of the skin, with the body cavity. Optionally a port, for example ports 1402, 1412, 1502, 1602 shown in FIGS. 14A-14B, 15A-15D, and 16A-16C is positioned within the passageway, for example to prevent damage to the body wall or to channel 403 when tools are inserted through the body opening into an internal lumen of the workspace device. In some embodiments, the passageway has a length smaller than 40 mm, for example smaller than 30 mm, smaller than 15 mm, smaller than 10 mm. In some embodiments, in a collapsed state, the workspace body and the wall, for example the expandable wall fits within the passageway.

Figure 18A:
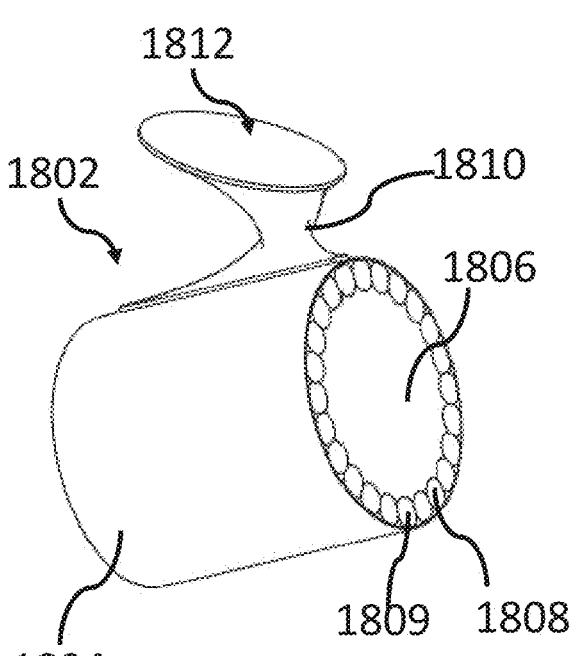
FIGS. 18A-18D are schematic illustrations of a laparoscopic workspace device having one or more side openings, for example tool insertion side openings, according to some exemplary embodiments of the invention.
Figure 18B:
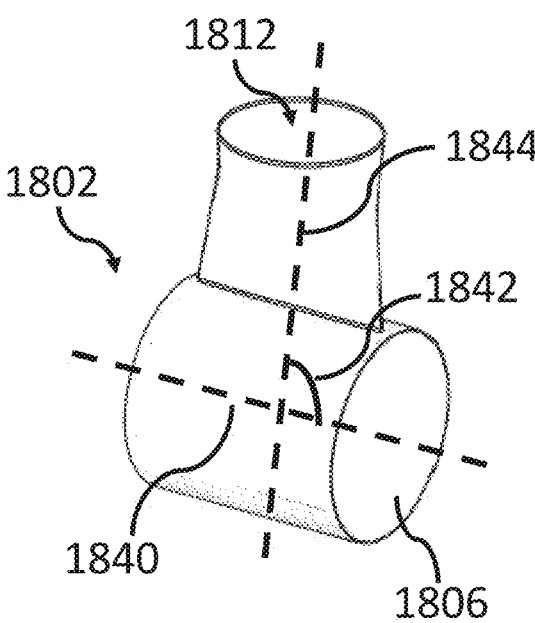
Figure 18C:
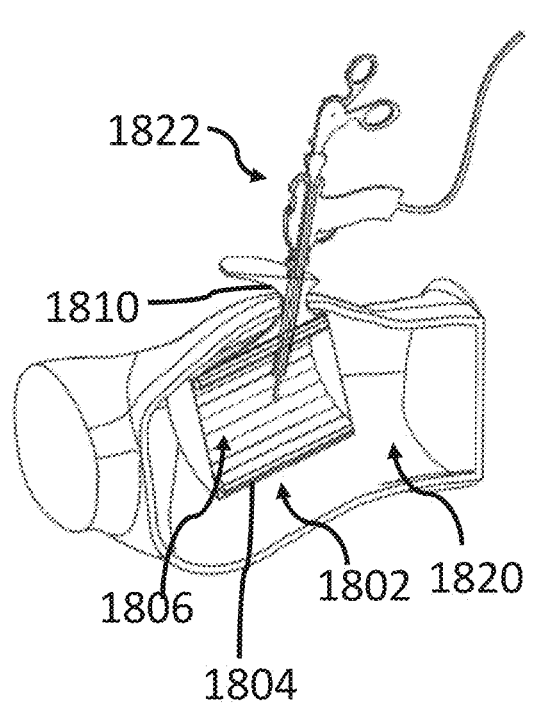
Figure 18D:
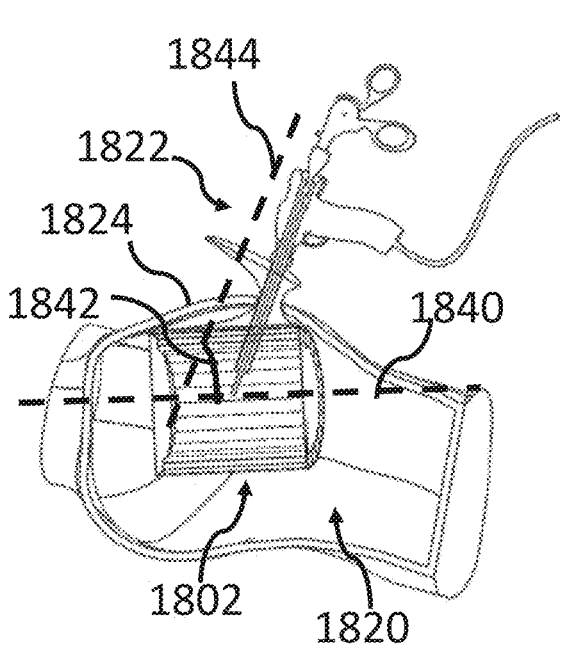

According to some exemplary embodiments, the workspace body is expandable within a body cavity, for example an abdominal, into which the passageway extends. In some embodiments, the workspace body is configured to expand into an expanded state within the body cavity. In some embodiments, when expanded, the workspace device extends axially from a proximal to a distal direction, for example to define a workspace axis, for example workspace axis 434. As used herein, in some embodiments, the term "proximal" refers to close to a body opening, and the term "distal" refers to close to a body cavity. Alternatively, for example as shown in FIGS. 18C and 18D, the workspace device, on an expanded state extends laterally, for example sideways. In some embodiments, laterally extending of the workspace device optionally defines a workspace axis which is at an angle larger than 35 degrees, for example larger than 45 degrees, larger than 50 degrees, larger than 80 degrees, or any intermediate, smaller or larger angle, relative to a proximal-distal axis between the body opening and the body cavity.

According to some exemplary embodiments, in an expanded state, the wall, for example expandable wall 401, comprises at least one inflatable chamber. In some embodiments, the at least one inflatable chamber is connected to at least one inflation tube configured to inflate the at least one inflatable chamber to reach a desired pressure. In some embodiments, the wall and/or at least one inflatable chamber of the wall optionally surrounds an internal lumen of the workspace device, for example internal lumen 409. In some embodiments, the wall 401 comprises a plurality of radial rigidizers, for example ribs 407 and 408. In some embodiments, radial rigidizers at least partly interconnect an inner surface of the wall 401 facing the internal lumen 409, and an outer surface of the wall. In some embodiments, the plurality of radial rigidizers are positioned within the at least one inflatable chamber. In some embodiments, the plurality of radial rigidizers divide the at least one inflatable chamber into two or more, for example a plurality of expandable segments. In some embodiments, the plurality of expandable segments are fluidically connected to each other within the at least one inflatable chamber.

According to some exemplary embodiments, for example as shown in FIG. 4B, an axial length 425 of at least some or all of the radial rigidizers, for example rib 407 is shorter than an axial length of the at least one inflatable chamber 422 and/or an axial length of the wall. In some embodiments, having ribs that are smaller than a length of the at least one inflatable chamber, or smaller in size than a size of a cross-section of the at least one inflatable chamber allows, for example fluid flow between expandable segments, for example adjacent expandable segments, for example proximal and/or distal to the ribs.

According to some exemplary embodiments, a wall 401 of workspace device 402 comprises an inner layer 404 and an outer layer 406. In some embodiments, the inner layer 404 and the outer layer are connected to form at least one inflatable chamber 432. In some embodiments, the at least one inflatable chamber is configured to be inflated by at least one inflation tube fluidically connected to the at least one inflatable chamber 432. In some embodiments, the at least one inflatable chamber is a chamber that is configured to maintain a predetermined pressure or range of pressure values, which are sufficient to resist collapse due to pressure within the body cavity, for example an insufflated body cavity.

According to some exemplary embodiments, the inner layer 404 and outer layer 406 are interconnected by a plurality of radial rigidizers, for example ribs 407 and 408. In some embodiments, the ribs 407 and 408 are positioned within the at least one inflatable chamber 432. In some embodiments, for example as shown in FIGS. 4A and 4B, a length 425 of a rib, for example an axial length, is smaller than a length, for example an axial length of the wall 401, when the wall is in an expanded state for example to allow fluid connection between expandable segments formed between adjacent ribs. In some embodiments, the radial rigidizers, for example ribs 407 and 408 divide the at least one inflatable chamber into the expandable segments. In some embodiments, the expandable segments, are vertical expandable segments, oriented along axis 434. Optionally, the vertical expandable segments, are arranged around the internal lumen 409, for example around a circumference of the internal lumen 409. In some embodiments, the wall 401 comprises at least one inflatable chamber in which the ribs and/or the expandable segments are positioned.

According to some exemplary embodiments, the wall 401 comprises at least one expandable distal ring near a base 412 of the workspace device. Alternatively, the base 412 is formed from at least one additional layer connected to the wall 401. In some embodiments, the base 412 is formed from a single layer of sheet material. In some embodiments, the at least one layer of sheet material forming the base 412 is connected to one or both of the at least one inner layer 404 and/or to the at least one outer layer 406. In some embodiments, the wall 401 comprises at least one expandable proximal ring near a channel 403. In some embodiments, the channel 403, which is optionally a sleeve, connects an opening of the internal lumen 409 with the body opening through which the device, for example 402 is introduced into the body cavity. In some embodiments, the channel is optionally formed from at least one additional layer of sheet material connected to the wall 401. Alternatively, the channel 403 is formed from one or both of the at least one inner layer 404 and the at least one outer layer 406. In some embodiments, the channel, for example channel 403 is optionally formed from a single layer of sheet material. In some embodiments, the channel, for example channel 403 is used to introduce tools, for example surgical tools into the internal lumen of the device, through the body opening.

According to some exemplary embodiments, the at least one inner layer 404 and the at least one outer layer 406, are optionally welded or glued to each other, for example at a proximal region near channel 403, and/or at a distal region near base 412, for example to form that at least one inflatable chamber and/or the expandable wall.

In some embodiments, the at least one expandable distal ring and/or the at least one expandable proximal ring, is formed by bending and connecting at least one of the layers to the same layer or to a different layer, for example the inner layer 404 and/or the outer layer 406 are connected to a disc shape layer 414. In some embodiments, the at least one expandable distal ring and/or the at least one expandable proximal ring are circumferential ring surrounding an internal lumen of the workspace device.

According to some exemplary embodiments, for example as shown in FIG. 4A, a base 412 of the workspace device 402 is distal to the at least one distal ring. In some embodiments, for example as shown in FIG. 4A, the base 412 is positioned distally to the wall 401. Alternatively, for example as shown in FIG. 4B, in workspace device 420 the distal ring is located distally to the base 412, for example to push the base 412 away from internal organs within the body cavity. Alternatively, for example as shown in FIG. 4B, the base 412 is proximal to the wall 401. Potential advantage of having a base proximal to the wall, may be reduce contact of the base 412 with a surface, that will first contact the distal portion of the wall.

Figures 4C, 4D:
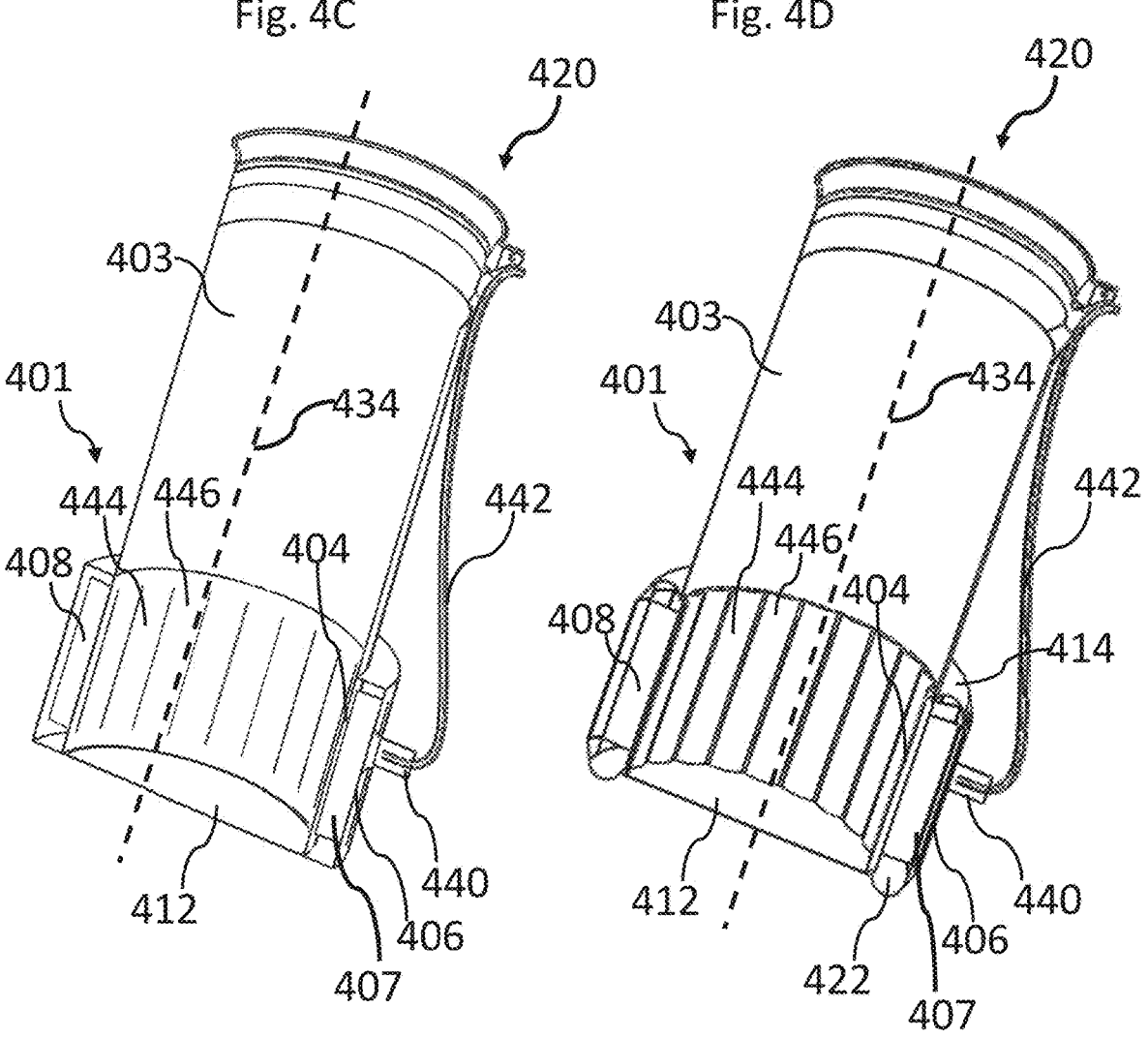
FIGS. 4C and 4D are schematic illustrations of a laparoscopic workspace device in a non-inflated state (FIG. 4C) and in an expanded state (FIG. 4D), according to some exemplary embodiments of the invention.

Reference is now made to FIG. 4C depicting a workspace device in a non-expanded, for example non-inflated state, according to some exemplary embodiments of the invention.

According to some exemplary embodiments, workspace device 420 comprises an expandable wall 401 formed from an inner layer 404 and an outer layer 406, and a plurality of vertical rigidizers, for example ribs 408 and 407. In some embodiments, at least some of the ribs or all of the ribs are elongated ribs having a long axis and a short axis. In some embodiments, a long axis of at least some of the ribs, or all of the ribs, as aligned along a long axis, for example a longitudinal axis 434 of the device 420. In some embodiments, the ribs interconnect the inner layer 404 and the outer layer 406. In some embodiments, the ribs are welded to each layer along welding lines formed in each layer.

According to some exemplary embodiments, a length of the outer layer 406 is larger than a length of the inner layer 404, and they are welded to each other with the ribs, to form the expandable wall, such that in a non-expanded state shown in FIG. 4A, both the outer layer 406 an the inner layer 404 have a smooth unfolded shape.

According to some exemplary embodiments, the ribs are distributed within the expandable wall 401 in an equal or in a varying distance from each other, separating the expandable wall 401 to a plurality of expandable segments. In some embodiments, the plurality of expandable segments are fluidically connected to each other, for example to allow inflation of the expandable wall 401 via a single inlet. In some embodiments, in a non-expandable state of the device 420, for example as shown in FIG. 4C, the inner layer 404 forming the inner surface of the device 420 and the outer layer 406 forming the outer surface of the device 420 are smooth, optionally having a non-wavy form.

According to some exemplary embodiments, the expandable wall 401 comprises at least one fluid flow connector, for example connector 440. In some embodiments, the connector 440 is a side connector, optionally comprising at least one valve. In some embodiments, the connector 440 is connectable to an inflation tube having a proximal end connected to a fluid source and a distal end connected to the connector 440.

According to some exemplary embodiments, for example as shown in FIG. 4D, inflation of the expandable wall 401 via the connector 440 expands the expandable wall 401 and each of the expandable segments 446 and 444 to form inner and outer curved surfaces or bulges, between two adjacent ribs. In some embodiments, inflation of the expandable wall 401 form the upper ring 414 and the lower ring 422 of the wall 401, that in the non-expanded state shown in FIG. 4A are flattened. In some embodiments, in an inflated state, for example shown in FIG. 4B, the expansion of the expandable segments forms a wavy inner surface of the device 420 by the inner layer 404 and an outer wavy surface of the device 420 by the outer layer 406.

Exemplary Workspace Device Wall with Rings

Reference is now made to FIGS. 5A and 5B depicting a workspace device having a wall with ring-shaped radial rigidizers, according to some exemplary embodiments of the invention.

According to some exemplary embodiments, a workspace device 502 comprises a wall 501 formed from at least one outer layer 502 of sheet material, and at least one inner layer 504 of sheet material. In some embodiments, the outer layer 502 and the inner layer define at least one expandable segment in the wall 501. In some embodiments, the wall 501 comprises a plurality of radial rigidizers 506 shaped as a ring, interconnecting the outer layer 502 and the inner layer 504. In some embodiments, the workspace device 500 further comprises a distal base 508 connected to the wall 501, and a channel, for example a cylindrical channel 510 connected to the wall 501 or to at least one of the outer layer 502 and the inner layer 504. In some embodiments, the cylindrical channel is an extension of the outer layer 502 or the inner layer 504.

According to some exemplary embodiments, the ring-shaped radial rigidizers divide a lumen between the inner and outer layer into expandable segments, for example circumferential expandable segments. In some embodiments, in an expanded state, for example when the wall 501 is inflated and expands, the inner layer 504 and the outer layer are smooth. In some embodiments, in an expanded state, adjacent circumferential expandable segments press against each other, for example axially press against each other along a vertical axis of the workspace device. In some embodiments, in an expanded state, adjacent circumferential expandable segments press against ring-shaped radial rigidizers positioned therebetween.

According to some exemplary embodiments, the ring-shaped radial rigidizer is made from Polyurethane. In some embodiments, for example as shown in FIG. 5C, the ring-shaped radial rigidizer is solid, and divides a wall of the workspace device into fluid-sealed circumferential expandable segments. Alternatively, for example as shown in FIG. 5D, the ring-shaped radial rigidizer is perforated and includes at least one opening, for example openings 512, configured to allow fluid flow between adjacent expandable segments.

Exemplary Workspace Device with an Inner Folded Layer and Ribs

Figures 6A, 6B, 6C, 6D:
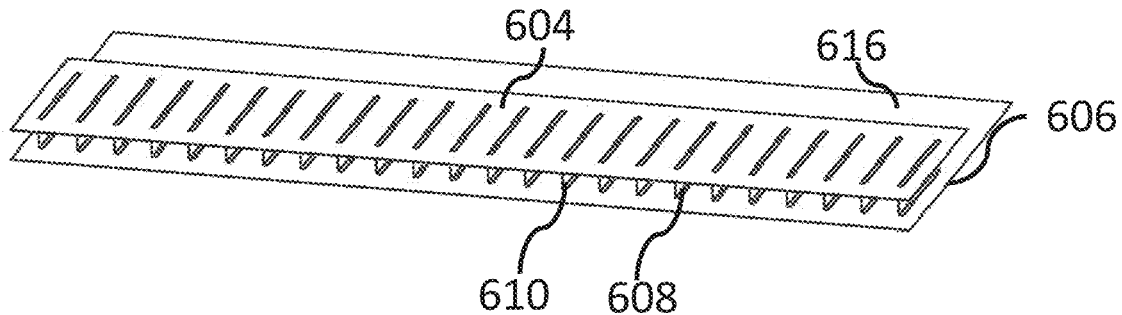
FIGS. 6A-6C are schematic illustration of a laparoscopic workspace device in an expanded state having a wall comprising inwardly extending expandable segments separated by ribs, according to some exemplary embodiments of the invention.
FIG. 6D is a schematic illustration of layers forming the wall of FIGS. 6A-6C in an unfolded state, according to some exemplary embodiments of the invention.

According to some exemplary embodiments, a workspace device comprises a wall, for example an expandable wall, formed from an inner layer and an outer layer having similar circumference lengths. In some embodiments, in an expanded state, the outer layer is smooth and the inner layer is folded, for example into a wavy pattern. Reference is now made to FIGS. 6A-6C, depicting a workspace device having a wall with an outer smooth surface and an inner folded surface connected by radial rigidizers, according to some exemplary embodiments of the invention.

According to some exemplary embodiments, a workspace device, for example workspace device 612 comprises an expandable wall 602 defining in an expanded state an internal lumen 603 of the workspace device 612. In some embodiments, the wall 602 comprises an outer layer 604 and an inner layer 606, and a plurality of radial rigidizers, for example ribs 608 and 610 disposed therebetween. In some embodiments, the ribs, for example ribs 608 and 610 interconnect the inner layer 606 of sheet material, and the outer layer 604 of sheet material.

According to some exemplary embodiments, the radial rigidizers, for example ribs 608 and 610 define a plurality of expandable segments, for example expandable segments 609 and 611. In some embodiments, in an expanded state, an inner surface of at least some of the expandable segments is curved, and an outer surface of the expandable segments is smooth. In some embodiments, in an expanded state, the formed expandable segments are vertical segments surrounding the internal lumen 603.

According to some exemplary embodiments, in an expanded state, the expandable segments are connected to a distal base, and to a proximal channel, for example cylindrical channel 614.

According to some exemplary embodiments, for example as shown in FIG. 6D, the wall is formed from two sheets of material having a similar length, for example when the sheets are unfolded. In some embodiments, the sheets are connected by the spaced apart ribs 608 and 610. Optionally, a sheet forming the inner layer of the wall is preshaped, for example shaped to acquire a curved or a wavy pattern, prior to connecting to the ribs.

According to some exemplary embodiments, for example as shown in FIG. 6C, the ribs are smaller than a maximal height of the wall, which allows, for example fluid flow between expandable segments.

Exemplary Flattened Workspace Device

According to some exemplary embodiments, a workspace device has a flattened, for example non-circular shape. Reference is now made to FIGS. 7A-7D, depicting a workspace device with a flattened shape, according to some exemplary embodiments of the invention.

According to some exemplary embodiments, for example as shown in FIG. 7A, at least two layers of sheet material, for example layer 704 and layer 706 are inter connected by a plurality of ribs, for example ribs 708 and 710. In some embodiments, in an unfolded state, for example as shown in FIG. 7A, a sheet forming the inner later of the wall, for example sheet 704 has a length which is larger than a length of a sheet forming the outer layer of the wall, for example sheet 706.

According to some exemplary embodiments, during manufacturing of the wall, sheet 704 is connected to sheet 706, for example along edges of sheet 706, for example to form an enclosed expandable wall. In some embodiments, for example as shown in FIG. 7B, the formed expandable wall is flexed, for example into a U-shape, to form an expandable base 712, and side walls 711 and 713 of the workspace device 702. In some embodiments, ends of side walls 711 and 713 are connected, for example, welded together, to form an enclosed flattened body of a workspace device optionally—by connecting the rim/edge of wall 704 to the adjacent rim of wall 704 and the rim of wall 706 to the adjacent rim of wall 706 to allow fluid passage circumferentially, to form a channel and an opening into the internal lumen of the workspace device.

According to some exemplary embodiments, the wall 713 comprises a plurality of expandable segments, which are inflatable, for example to expand. In some embodiments, the plurality of expandable segments are fluidically connected to each other, forming for example a single inflatable chamber. In some embodiments, for example as shown in FIG. 7D, the expandable segments are vertical expandable segments aligned along a vertical axis of the workspace device.

According to some exemplary embodiments, for example as shown in FIG. 7C, the formed wall 713 comprises one or more weakened regions generated along a desired bending line 715 surrounding the base 712, for example to allow easier flexing of the wall at the bending line 715. In some embodiments, the weakened regions are generated by welding the wall at specific locations along the bending line 715. In some embodiments, the bending line allows, for example, easier bending of the wall 713 at the base 712.

Exemplary Workspace Device Having a Wall with Inner and Outer Radial Rigidizers

Reference is now made to FIGS. 8A and 8B, depicting a workspace device having a wall comprising circumferential rings, according to some exemplary embodiments of the invention.

According to some exemplary embodiments, a body of a workspace device 802 comprises a wall 804 formed from a plurality of ring-shaped expandable segments, for example segments 806 and 808 connected to each other. In some embodiments, each of the ring-shaped expandable segments is preformed by two ring-shaped layers of sheet material, for example layers 805 and 807 are connected to each other along an inner circumference of the layers by at least one radial rigidizer, for example an internal radial rigidizer 809. Additionally, the layers 805 and 807 are connected to each other along an outer circumference of the layers by at least one additional radial rigidizer, for example an external radial rigidizer 811.

According to some exemplary embodiments, the wall 804 is preformed by connecting ring-shaped expandable segments to each other, for example by welding or gluing. In some embodiments, adjacent expandable segments are connected to each other along a large surface area of each layer. In some embodiments, for example as shown in FIG. 8C, a length 820 of a connecting portion, for example an interface between adjacent expandable segments is similar to a height 822 of an expandable segment. Alternatively, for example as shown in FIG. 8D, a length 824 of an interface between adjacent expandable segments is larger than a height 826 of an expandable segment. A potential advantage of having an interface length which is larger than a height of an expandable segments may be to increase rigidity in a radial direction of the expandable segments and/or the wall.

According to some exemplary embodiments, for example as shown in FIGS. 8A and 8B, in an expanded state of the workspace device 802, the expandable segments press against each other in an axial direction 828, for example to increase rigidity in a radial direction 830. In some embodiments, the workspace device 802 comprises a proximal channel 832, for example a cylindrical proximal channel defining a passageway into an internal lumen of the workspace device 802, and a distal base 834. In some embodiments, the proximal channel 832 and/or the distal base 834 are connected, for example welded or glued to the wall 804. Optionally, the proximal channel 832 and/or the distal base 834 are connected to the internal 809 and/or to the external 811 radial rigidizers.

According to some exemplary embodiments, the internal 809 and/or the external 811 radial rigidizers are formed from a, a plate, a disk or a ring of a material, for example polyurethane.

Exemplary Workspace Device with Extendable Expandable Segments

According to some exemplary embodiments, a workspace device comprises an expandable wall having outwardly or inwardly extending expandable segments that contact each other in an expanded state, for example to define radial rigidizers therebetween.

Reference is now made to FIGS. 9A-9C depicting a workspace device having an expandable wall with outwardly extending expandable segments, according to some exemplary embodiments of the invention.

According to some exemplary embodiments, a workspace device, for example workspace device 902 comprises an expandable wall 904 defining in an expanded state, an internal lumen 905 of the workspace device 902. In some embodiments, the workspace device is configured to be positioned in an expanded state within a body cavity, for example an abdominal cavity. In some embodiments, in an expanded state, the wall 904 comprises an inner layer 906 forming an inner smooth surface facing the internal lumen. Additionally, in an expanded state, the wall 904 comprises a plurality of outwardly extending expandable segments, for example segments 908 and 910. In some embodiments, for example as shown in FIG. 9B, the segments 908 and 910 outwardly extend from a center of the internal lumen 905.

According to some exemplary embodiments, the expandable segments, for example segments 908 and 910 are vertical expandable segments. In some embodiments, the segments 908 and 910, for example vertical expandable segments, surround the internal lumen 905. In some embodiments, in an expanded state, for example as shown in FIGS. 9B and 9C, the outwardly extending expandable segments are pressed, for example laterally pressed, against each other. In some embodiments, the outwardly extending expandable segments optionally have a similar width or a similar diameter. Alternatively, at least some of the outwardly extending expandable segments optionally have a different diameter or a different width.

According to some exemplary embodiments, for example as shown in FIG. 9B, the wall 904 is formed from at least one inner smooth layer 906 and at least one outer curved layer 912. In some embodiments, the at least one outer curved layer 912 is curved to form at least one expandable segment, for example by contacting the at least one inner smooth layer 906 at two or more locations along a circumference of the inner layer 906. Alternatively, the at least one outer curved layer 912 is preformed to include curved portions and smooth portions. In some embodiments, the at least one outer curved layer 912 is attached to the inner smooth layer 906, such that smooth portions are attached to the smooth inner layer 906 and curved portions of the outer curved layer, outwardly extend away from the inner smooth layer 906, for example to form the expandable segments 908 and 910.

According to some exemplary embodiments, for example as shown in FIG. 9C, in an expanded state, walls of two adjacent expandable segments, for example expandable segments 908 and 910 contact each other at an interface region 914. In some embodiments, the interface region 914 is spaced-apart from the inner layer 906 or from smooth regions of the outer layer 912. Alternatively, the interface region between two adjacent expandable segments contact the inner layer 906 or the smooth regions of the outer layer 912.

According to some exemplary embodiments, the interface region 914 is formed from at least two walls of adjacent expandable segments, each from a different expandable segment, pressed against each other that rigidize, for example radially rigidize the interface region 914. In some embodiments, the two walls are fixedly attached to each other, for example by welding or gluing them together. In some embodiments, the expandable segments extend, in an expanded state, to a maximal distance of up to 30 cm, for example up to 25 cm, up to 20 cm or any intermediate, smaller or larger value from the inner smooth layer 906 of the wall 904.

According to some exemplary embodiments, each of the expandable segments in an expanded state has a tubular shaped closed at both ends. In some embodiments, at least some or all of the expandable segments, for example expandable segments 908 and 910 are fluidically connected to each other, for example to form a single inflatable segment. Alternatively, one or more of the expandable segments are fluidically isolated from other expandable segments of the wall. In some embodiments, in an expanded state, the outwardly extending expandable segments are flexible for example, to prevent damage to organs and tissue in the body cavity that contact the wall 904.

Figures 10A, 10B, 10C:
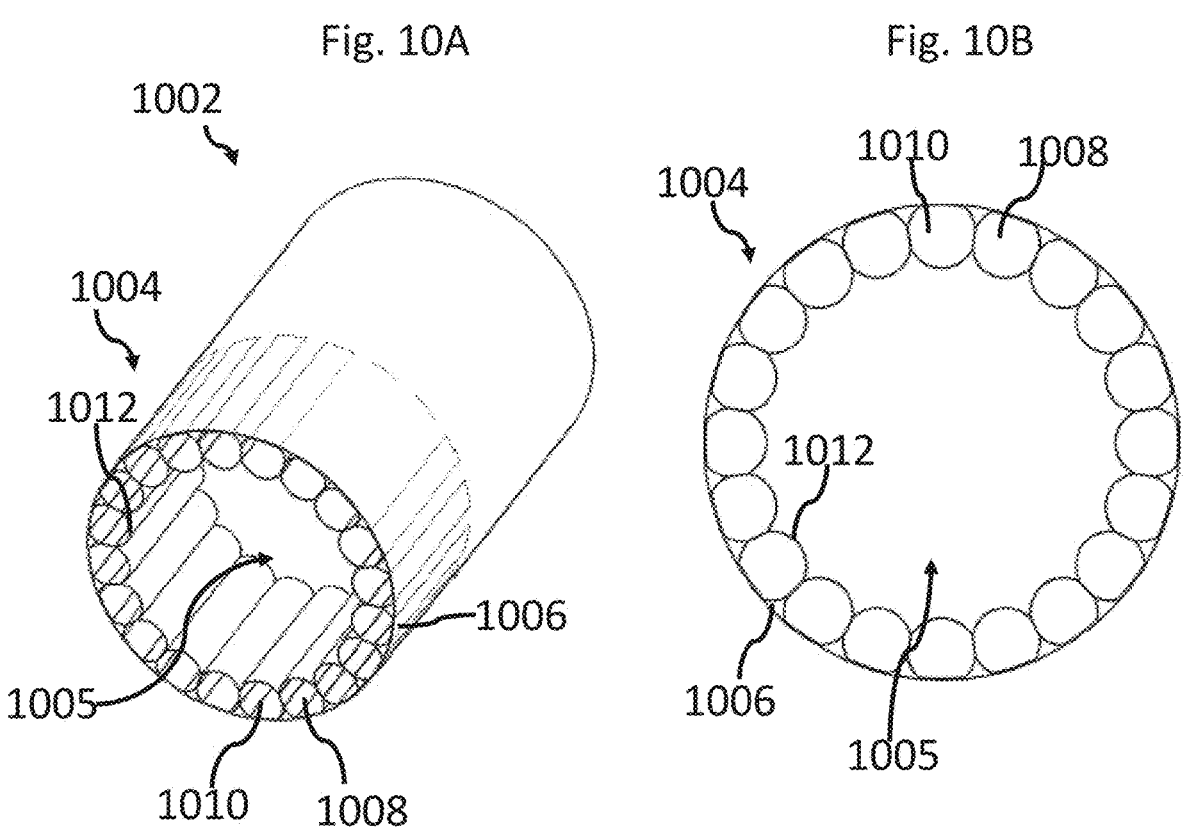
FIGS. 10A-10C are schematic illustrations of a laparoscopic workspace device having a wall that includes inwardly extending vertical expendable segments, according to some exemplary embodiments of the invention.

Reference is now made to FIGS. 10A-10C depicting a workspace device having an expandable wall with inwardly extending expandable segments, according to some exemplary embodiments of the invention.

According to some exemplary embodiments, a workspace device, for example workspace device 1002 comprises an expandable wall 1004 defining, in an expanded state, an internal lumen 1005 of the workspace device 1002. In some embodiments, the workspace device is configured to be positioned in an expanded state within a body cavity, for example an abdominal cavity. In some embodiments, in an expanded state, the wall 1004 comprises an outer layer 1006 forming an outer smooth surface facing the body cavity. Additionally, in an expanded state, the wall 1004 comprises a plurality of inwardly extending expandable segments, for example segments 1008 and 1010. In some embodiments, for example as shown in FIG. 10B, the segments 1008 and 1010 inwardly extend towards a center of the internal lumen 1005.

According to some exemplary embodiments, the expandable segments, for example segments 1008 and 1010 are vertical elongated expandable segments. In some embodiments, the segments 1008 and 1010, for example vertical expandable segments, surround the internal lumen 1005. In some embodiments, in an expanded state, for example as shown in FIGS. 10B and 10C, the inwardly extending expandable segments are pressed, for example laterally, against each other.

According to some exemplary embodiments, for example as shown in FIG. 10B, the wall 1004 is formed from at least one outer smooth layer 1006 and at least one inner curved layer 1012. In some embodiments, the at least one inner curved layer 1012 is curved to form at least one expandable segment, for example by contacting the at least one outer smooth layer 1006 at two or more locations along a circumference of the outer layer 1006. Alternatively, the at least one inner curved layer 1012 is preformed to include curved portions and smooth portions. In some embodiments, the at least one inner curved layer 1012 is attached to the outer smooth layer 1006, such that the smooth portions are attached to the smooth outer layer 1006 and the curved portions of the inner curved layer 1012, inwardly extend away from the outer smooth layer 1006, for example to form the expandable segments 1008 and 1010.

According to some exemplary embodiments, for example as shown in FIG. 10C, in an expanded state, walls of two adjacent expandable segments, for example expandable segments 1008 and 1010 contact each other at an interface region 1014. In some embodiments, the interface region 1014 is spaced-apart from the outer layer 1006, or from smooth regions of the inner layer 1012. Alternatively, the interface region between two adjacent expandable segments contact the outer layer 1006 or the smooth regions of the inner layer 1012.

According to some exemplary embodiments, the interface region 1014 is formed from at least two walls of adjacent expandable segments, each from a different expandable segment, pressed against each other that rigidize, for example radially rigidize the interface region 1014. In some embodiments, the at least two walls are fixedly attached to each other, for example by welding or gluing them together. In some embodiments, the expandable segments extend, in an expanded state, to a maximal distance of up to 30 cm, for example up to 25 cm, up to 20 cm or any intermediate, smaller or larger value from the outer smooth layer 1006 of the wall 1004.

According to some exemplary embodiments, each of the expandable segments in an expanded state has a tubular shaped closed at both ends. In some embodiments, at least some or all of the expandable segments, for example expandable segments 1008 and 1010 are fluidically connected to each other, for example to form a single inflatable segment. Alternatively, one or more of the expandable segments are fluidically isolated from other expandable segments of the wall. In some embodiments, in an expanded state, the inwardly extending expandable segments are flexible for example, to prevent damage to organs and tissue in the internal lumen that contact the wall 1004.

Figure 11:
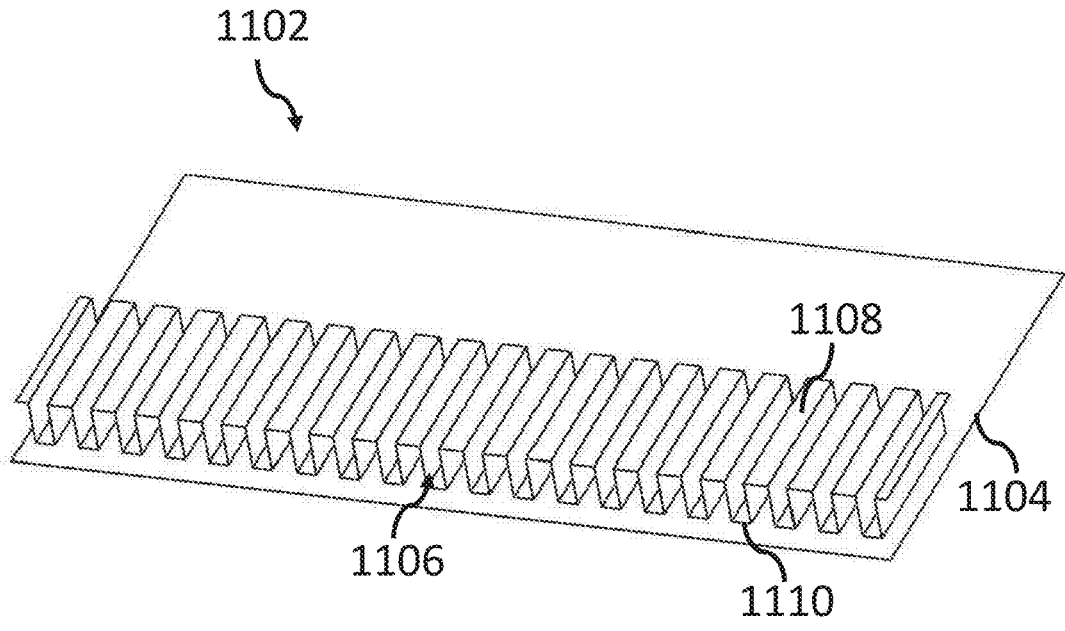
FIG. 11 is a schematic illustration of an unfolded assembly between a flat layer and a curved layer bended to form the expandable segments shown in FIGS. 9A-9C and in FIGS. 10A-10C, according to some exemplary embodiments of the invention.

Reference is now made to FIG. 11, depicting a wall of a workspace device having a smooth side and a curved opposite site in a preformed state, according to some exemplary embodiments of the invention.

According to some exemplary embodiments, a wall of a workspace device, for example wall 1102 is formed from at least one smooth layer of sheet material, for example layer 1104, and at least one bended layer of sheet material, for example bended layer 1106. In some embodiments, in an unfolded state, for example as shown in FIG. 11, the smooth layer 1104 is planar. In some embodiments, for example as shown in FIG. 11, the bended layer is shaped to have a non-planar shape, for example a wavy shape. In some embodiments, the bended layer 1106 is at least partly fixedly attached to the smooth layer 1104, for example by welding or gluing. In some embodiments, planar smooth portions, for example portion 1110 of the bended layer 1106, are fixedly attached to the smooth layer 1104, which is for example, a planar layer in an unfolded state.

According to some exemplary embodiments, for example as shown in FIG. 11, each expandable segment is formed at least partly from at least one smooth layer and from at least one different curved layer, for example a bended layer. In some embodiments, in each expandable segment, a length of the curved layer defining the expandable segment is at least 1.3 times, for example at least 1.5 times, at least 2 times or any intermediate, smaller or larger value, of a length of a smooth layer defining the expandable segment.

Exemplary Workspace Device Wall with Inner Expandable Segments

Figure 12A:
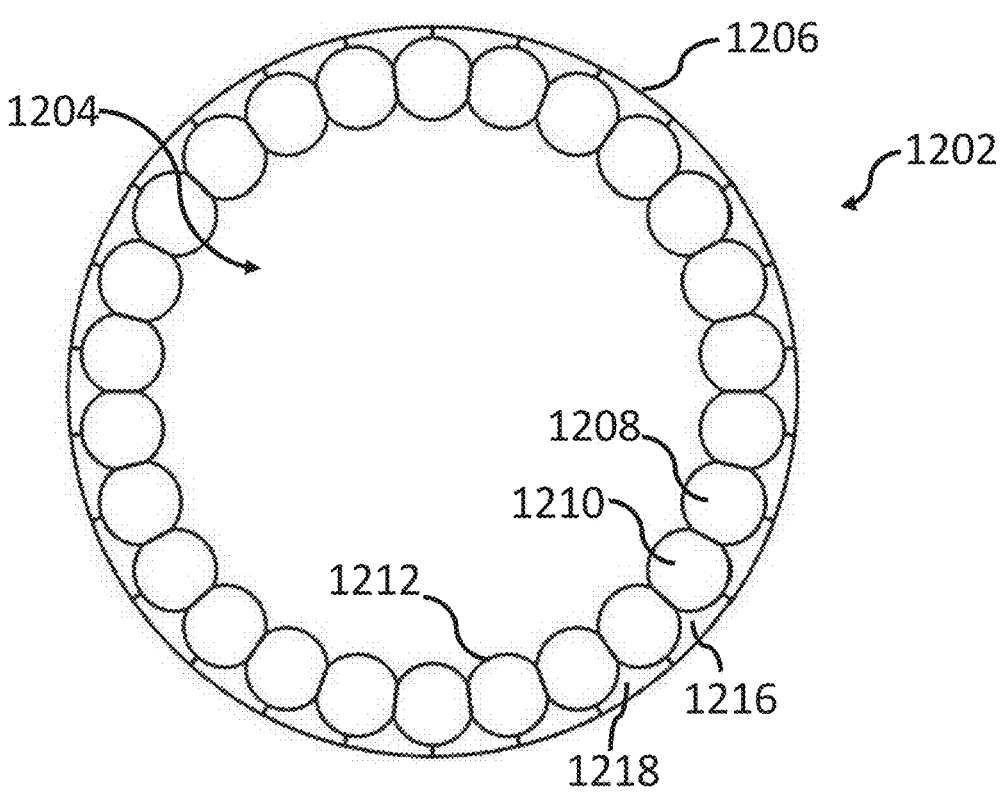
FIGS. 12A and 12B are a schematic cross-section illustrations of a laparoscopic workspace device wall having inner expandable segments connected to each other, according to some exemplary embodiments of the invention.
Figure 12B:
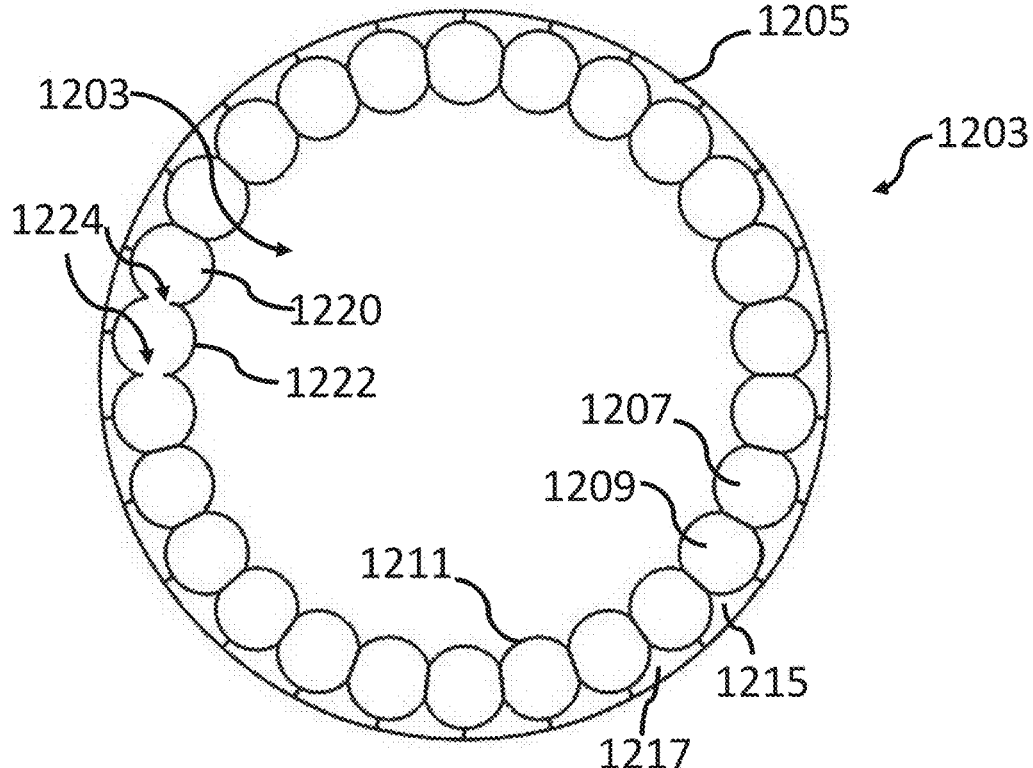

Reference is now made to FIGS. 12A and 12B, depicting a wall of a workspace device having inner expandable segments, according to some exemplary embodiments of the invention.

According to some exemplary embodiments, a workspace device comprises an expandable wall, for example wall 1202, defining an internal lumen 1204 of the workspace device. In some embodiments, the wall 1202 has an outer smooth surface, and a plurality of inner expandable segments, for example segments 1208 and 1210 within the internal lumen 1204. In some embodiments, the inner expandable segments surround the internal lumen, when the wall 1202 is expanded, for example inflated. Optionally, the inner expandable segments are vertical segments.

According to some exemplary embodiments, the wall 1202 is formed from at least one smooth layer of sheet material, having an outer smooth surface and an inner surface facing the internal lumen 1204. In some embodiments, the expandable segments are formed from at least one additional curved layer 1212 of sheet material that is curved and/or flexed to form the plurality of expandable segments. In some embodiments, the formed expandable segments are connected to the inner surface of the smooth layer in specific locations. In some embodiments, the expandable segments are connected to the smooth layer 1206, for example by welding or gluing. Alternatively, the expandable segments are connected to the smooth layer 1206 by extensions of the curved layer.

According to some exemplary embodiments, in an expanded state, the expandable segments, for example segments 1208 and 1210 are cylindrical. In some embodiments, in an expanded state adjacent expandable segments contact and optionally press each other. In some embodiments, the wall 1202 comprises additional expandable segments, for example segments 1216 and 1218 defined between the inner expandable segments and the outer smooth layer 1206. In some embodiments, segments 1216 and 1218 expand when the inner expandable segments, for example segments 1208 and 1210 are inflated.

According to some exemplary embodiments, at least some or all of the inner expandable segments, for examples segments 1208 and 1210 are fluidically connected to each other, for example to form a single inflatable chamber.

According to some exemplary embodiments, the wall 1203 defining an internal lumen 1203 is formed by bending a single flexible sheet of material. In some embodiments, the single flexible sheet is bent to form an outer layer 1205, the expandable segments 1207 and 1209, and the inner layer 1211 facing the internal lumen. In some embodiments, at least some or all of the expandable segments 1207 and 1209 are fluidically connected to each other, for example to form a shared inflatable chamber. In some embodiments, for example as shown in FIG. 12B, the expandable segments, for example expandable segments 1220 and 1220 are fluidically connected to each other optionally by openings, for example openings 1224 formed in walls of the expandable segments that contact each other. Alternatively or additionally, the openings, for example openings 1224 comprise channels interconnecting two or more of the expandable segments to form an inflatable chamber.

Exemplary Workspace Device Wall with Vertical and Horizontal Segments

Reference is now made to FIGS. 13A-13C depicting a workspace device having an expandable wall with vertical and horizontal segments, according to some exemplary embodiments of the invention.

According to some exemplary embodiments, a workspace device, for example workspace device 1302 comprises a body 1302 having an expandable wall 1304 defining, for example when the wall 1304 is expanded, an internal lumen 1305 having an opening 1306. In some embodiments, the body comprises a channel 1308, for example a cylindrical channel, connected to the wall 1304, and defines a flow path between the opening 1306 and the internal lumen. Alternatively, the channel 1308 is integrated with the wall 1304, for example with at least one layer of sheet material forming the wall 1304. In some embodiments, the body comprises a distal base 1310. In some embodiments, the distal base comprises at least one expandable segment, and is optionally formed from two or more layers of sheet material.

According to some exemplary embodiments, the wall 1304 comprises a plurality of vertical expandable segments, for example segments 1312 and 1314, surrounding the internal lumen 1305. In some embodiments, in an expanded state, adjacent vertical expandable segments contact each other. Optionally, walls of adjacent vertical expandable segments are fixedly attached to each other, for example by welding or gluing. Alternatively, in an expanded state, for example as shown in FIG. 13C, at least some or all of the vertical expandable segments are spaced apart from adjacent segments, for example segments 1312 and 1314. In some embodiments, the adjacent segments are connected by a smooth wall portion 1316, for example a flat wall portion. In some embodiments, the smooth wall portion is formed from at least two layers forming an expandable segment. Alternatively, the smooth wall portion is formed from a single layer. In some embodiments, in an expanded state, the smooth wall portion 1316 is stretched, for example stretched laterally between adjacent vertical expandable segments 1312 and 1314.

According to some exemplary embodiments, the vertical expandable segments are shaped as an elongated cylinder, optionally closed at both ends. In some embodiments, at least some of the vertical expandable segments are fluidically connected to each other, forming for example a single inflatable chamber. Alternatively, each or at least some of the vertical expandable segments are fluidically isolated from other vertical expandable segments.

According to some exemplary embodiments, the body of the workspace device comprises at least one distal horizontal expandable segment 1318. In some embodiments, the distal horizontal segment 1318 comprises base 1310. In some embodiments, in an expanded state, the at least one distal horizontal segment is shaped as a ring. In some embodiments, the base 1310 is fixedly connected to the distal horizontal segment 1318, for example by welding or gluing. In some embodiments, the at least one distal horizontal segment is connected, for example fixedly connected, to the wall 1304.

According to some exemplary embodiments, the body of the workspace device comprises at least one proximal horizontal expandable segment 1320. In some embodiments, in an expanded state, the at least one proximal horizontal segment is shaped as a ring. In some embodiments, the at least one proximal horizontal segment 1320 is connected, for example fixedly connected, to the wall 1304.

According to some exemplary embodiments, the at least one distal horizontal segment 1318, and/or the at least one proximal segment 1320, radially extend relative to the wall 1304. Optionally, the at least one distal horizontal segment 1318, and/or the at least one proximal segment 1320, are connected to the vertical expandable segments, for examples segments 1312 and 1314. In some embodiments, the at least one distal horizontal segment 1318, and/or the at least one proximal segment 1320 are perpendicular to the vertical segments.

According to some exemplary embodiments, the at least one distal horizontal segment 1318, and/or the at least one proximal segment 1320 are inflatable segments. In some embodiments, the at least one distal horizontal segment 1318, and/or the at least one proximal segment 1320 are fluidically connected to the wall 1304, for example to one or more of the vertical expandable segments of the wall. In some embodiments, the at least one distal horizontal segment 1318, and/or the at least one proximal segment 1320 are formed from at least two layers of sheet material welded together. In some embodiments, in a preformed unfolded state, each of the at least two layers is shaped as a ring. In some embodiments, in a preformed unfolded state, an inner diameter of one of the ring-shaped layer forming the horizontal segment has an inner diameter which is larger than an inner diameter of a second ring-shaped layer of the horizontal segment. Alternatively, in a preformed unfolded state each of the ring-shaped layers has the same inner diameter.

Figure 13D:
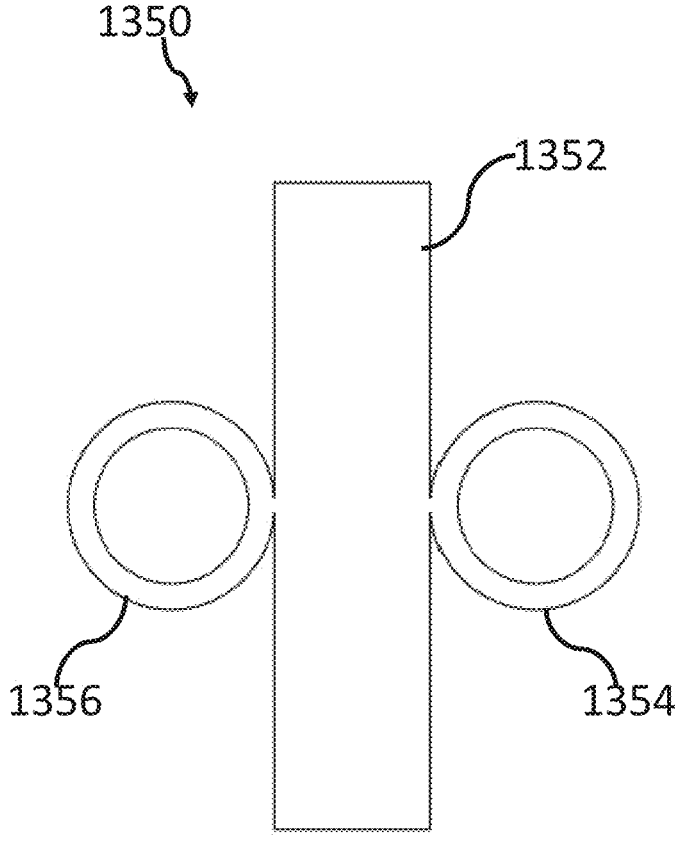
FIG. 13D is a schematic illustration of the laparoscopic workspace device on FIGS. 13A-13C in an unfolded state, according to some exemplary embodiments of the invention.

According to some exemplary embodiments, for example as shown in FIG. 13D, the body is formed from two layers of sheet material, each comprises a layer of the wall, a layer of the distal horizontal ring and a layer of the proximal horizontal ring. In some embodiments, in a preform unfolded state, a first body layer 1350 comprises a sheet material layer 1352 of the wall, connected to two ring-shaped layers 1354 and 1356, each on an opposite side of the layer 1352. In some embodiments, two body layers, for example identical body layers are attached to each other, for example fixedly attached to each other, to form the body of the workspace device. In some embodiments, the two body layers are fixedly attached to each other by welding or gluing.

Exemplary Port

Figure 14A:
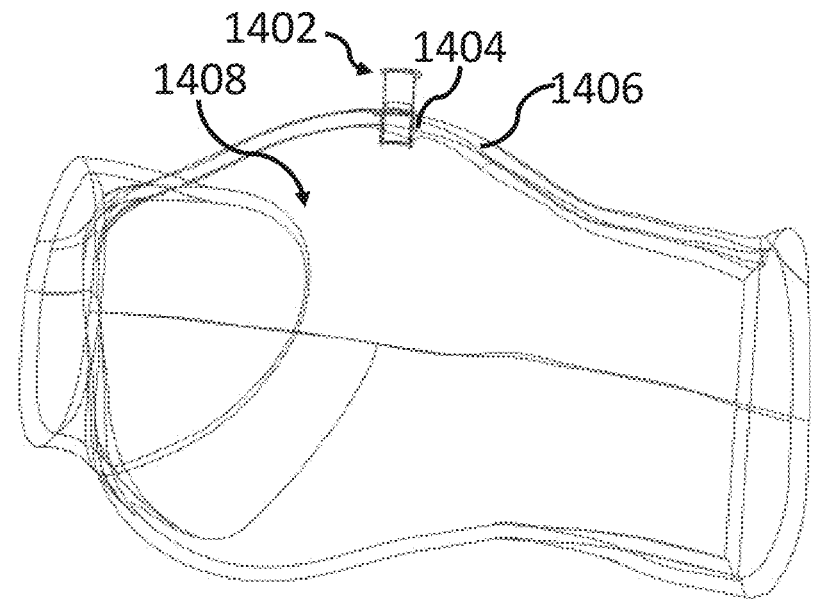
FIGS. 14A-14B are schematic illustrations of a port that includes a foldable portion, according to some exemplary embodiments of the invention.

Reference is now made to FIG. 14A depicting a port configured to define a flow path between an intra-body lumen and an outer skin surface, according to some exemplary embodiments of the invention.

According to some exemplary embodiments, a port, for example port 1402 comprises an inner channel having at least two openings, and is configured to be positioned within a body opening, for example an anatomical body opening or a surgical body opening formed by incision of a body wall. In some embodiments, the port 1402 is configured to bridge a channel through a body wall 1404 between an intra-body lumen 1408 and the outer surface of the skin.

Figure 14B:
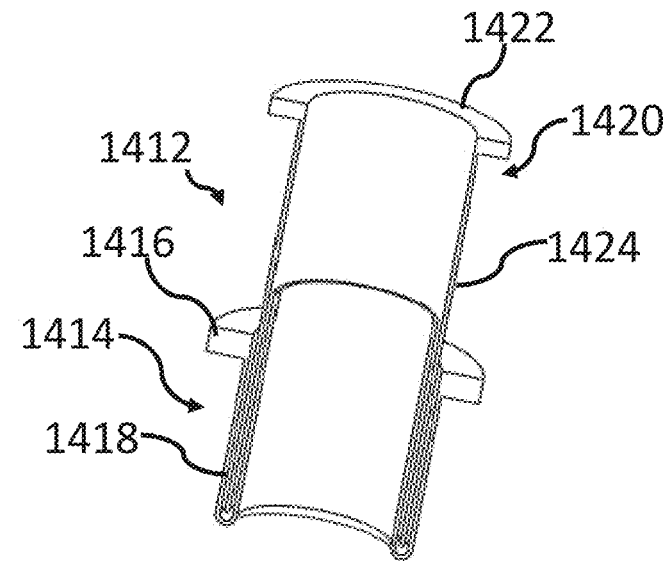

According to some exemplary embodiments, for example as shown in FIG. 14B, a port 1412 comprises an outer cylinder 1414, and an inner cylinder 1420 slidable within an inner lumen of the outer cylinder 1414. In some embodiments, the outer cylinder 1414 comprises a proximal rim 1416 configured to be placed in contact with an outer surface of the skin, and a folded body 1418. In some embodiments, the outer cylinder 1414, for example the folded body 1418 is flexible. In some embodiments, the folded body is formed from at least one flexible sheet. In some embodiments, the folded body 1418 comprises a groove having an opening facing the rim 1416.

According to some exemplary embodiments, the inner cylinder 1420 comprises a proximal rim 1422 and a cylindrical body 1424. In some embodiments, the inner cylinder 1420, for example the cylindrical body 1424 is rigid. In some embodiments, a wall of the cylindrical body is shaped and sized to be inserted into the groove in the folded body. In some embodiments, a width of a wall of the cylindrical body is thinner than a width of the groove.

According to some exemplary embodiments, the outer cylinder 1414, which is optionally flexible, is inserted through a body opening 1404, while the body 1418 is folded. In some embodiments, the inner cylinder 1420 is then slides within the groove in the folded body, through the body opening and into the body lumen 1408. In some embodiments, the sliding of the inner cylinder 1420, which is optionally rigid, into the body lumen 1408 unfolds the folded body of the outer cylinder 1414. In some embodiments, the inner cylinder 1420 slides within the outer cylinder 1414 until rim 1422 contacts rim 1416. In some embodiments, when inner cylinder 1420 is positioned within outer cylinder 1414, the wall of the cylindrical body 1424, which is optionally rigid keeps the body 1418 which is optionally flexible in an unfolded state.

According to some exemplary embodiments, for example as shown in FIG. 14B, a port assembly, for example an assembly of port 1402 comprises at least one outer foldable portion, and at least one inner portion slidable within said outer portion. In some embodiments, the at least one outer foldable portion is optionally cylindrical in a folded state. In some embodiments, the at least one outer foldable portion is at least partly folded when inserted through the body opening. Optionally, the at least one outer portion is optionally flexible. In some embodiments, the inner portion is optionally rigid. In some embodiments, sliding of the at last one inner portion unfolds the at least one outer foldable portion inside the body. Additionally, the at least one inner portion anchors the at least one foldable portion, for example within the body opening. In some embodiments, the at least one inner portion is optionally shaped as a cylinder.

Potential advantage of having a port with a flexible outer cylinder may be to prevent damage to the body opening, when the outer cylinder passes through the body opening 1404 and contacts the body wall 1406.

Potential advantage of having a port with a rigid inner cylinder may be to prevent the closure of a passageway into the body lumen 1408 formed by the outer cylinder. An additional potential advantage of a rigid inner cylinder may be to prevent damage to the body wall 1408 when one or more surgical instruments are inserted through the inner cylinder into the body lumen.

Reference is now made to FIGS. 15A-15D, depicting a port having an intra body cavity expandable anchor, according to some exemplary embodiments of the invention.

Figures 15A, 15B, 15C, 15D:
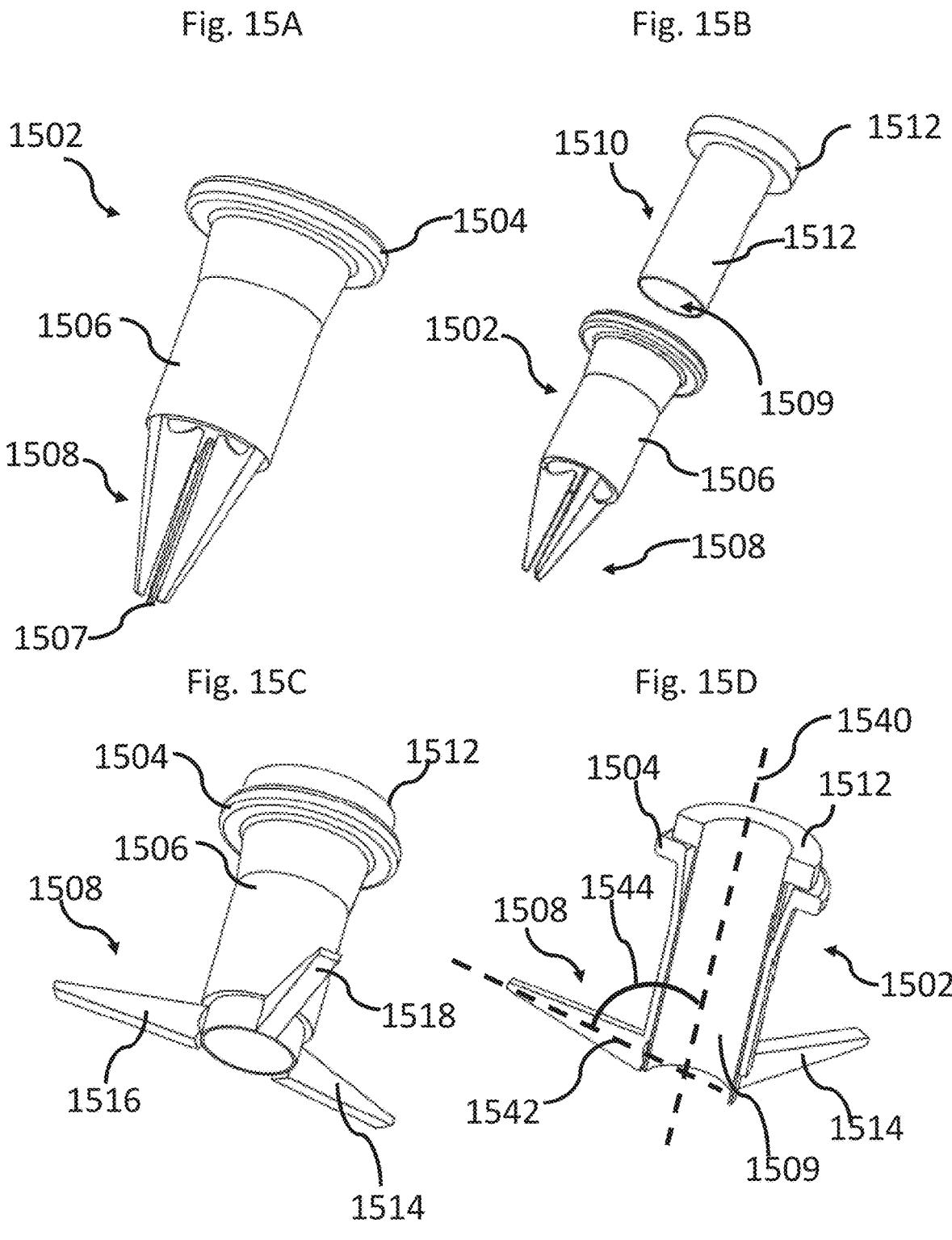
FIGS. 15A-15D are schematic illustrations of a port that includes a deployable anchor, according to some exemplary embodiments of the invention.

According to some exemplary embodiments, a port assembly comprises an outer portion 1502, and an inner portion 1510 shaped and sized to fit within the outer portion 1502. In some embodiments, the outer portion 1502 comprises a body 1506 defining a lumen, a proximal annulus 1504 shaped and sized to be positioned outside the body and distal expandable anchor 1508, for example an inner expandable bolster. In some embodiments, the body 1506 is optionally cylindrical. In some embodiments, the body 1508 comprises a proximal opening and a distal opening. In some embodiments, the distal expandable anchor is configured to move between a closed state, for example as shown in FIGS. 15A and 15B, for example when entering through a body opening into a body cavity. In some embodiments, in a closed state, the distal expandable anchor has a conical shaped with optionally a tapered end 1507. In some embodiments, in a closed state, the distal expandable anchor at least partly blocks the distal opening of the body 1506.

According to some exemplary embodiments, the inner portion 1510 comprises a body 1512 insertable within a lumen of the outer portion 1502. In some embodiments, the inner portion 1510 comprises a proximal annulus which is shaped and sized to be positioned outside the body, optionally in contact with the proximal annulus of the outer portion 1502. In some embodiments, the inner portion body 1512 has a cylindrical shape, and defines an inner lumen 1509.

According to some exemplary embodiments, for example as shown in FIGS. 15C and 15D, sliding or insertion of the inner portion body 1506 into the outer portion body 1506, expands the distal expandable anchor 1508. In some embodiments, when expanded, the anchor 1508 moves into an open state in which the anchor 1508 is placed in contact with an inner surface of the body cavity or an inner surface of the body wall, for example to prevent unwanted removal of the port. In some embodiments, expansion of the anchor 1508 opens a distal opening of the body 1506, for example to form a channel between the outer surface of the skin and the body cavity. In some embodiments, when the port is introduced at least partly into a workspace device, the port defines a channel between the external surface of the skin and a lumen of the workspace device.

According to some exemplary embodiments, expandable inner anchor comprises one or more movable protrusions, for example protrusions 1514, 1516 and 158, configured to move when the inner portion body 1510 is inserted or slides within the outer portion body 1506. In some embodiments, the one or more outer portion body and/or the inner portion body 1506 have a cylindrical shape. In some embodiments, the outer portion 1502 of the port, for example the body 1506 and/or the anchor is at least partly flexible or elastic, for example to prevent damage to at least one of the body cavity, a wall of the body and the body opening, when contacting a body tissue of a subject. In some embodiments, the inner portion 1510 of the port, for example body 1512 is rigid, for example to ensure deployment of the anchor 1508 and/or to prevent contact or pressure between tools, for example surgical tools passing through the inner lumen into a body cavity or into a workspace device and the body of the subject.

According to some exemplary embodiments, the anchor 1508 is configured to expand, for example reversibly expand when the port inner portion 1510 slides into the outer portion 1502. In some embodiments, the anchor is configured to collapse into a closed state, when removing the inner portion 1510 from the outer portion 1510 of the port. Optionally, in a resting state, the anchor 1508 is collapsed.

According to some exemplary embodiments, the movable protrusions move to an angle 1544 smaller than 100 degrees, for example smaller than 95 degrees, smaller than 90 degrees, smaller than 80 degrees or any intermediate, smaller or larger angle value relative to a longitudinal distal-proximal axis 1540 of the port 1502. In some embodiments, the movable protrusions move to contact an inner surface of the body cavity wall. In some embodiments, positioning of the inner portion 1510 within the outer portion 1502 locks the protrusions at angle 1544.

Reference is now made to FIGS. 16A-16C depicting a port of a body opening formed from two or more overlapping arc-shaped flexible sheets, according to some exemplary embodiments of the invention.

According to some exemplary embodiments, a port 1602 is configured to be positioned within a body opening, for example an anatomical or a surgical body opening. In some embodiments, the port 1602 comprises a body 1602 which is optionally elongated, defining an inner lumen 1616 having a distal opening and a proximal opening. In some embodiments, the port 1602 comprises an annulus 1604 surrounding the proximal opening, connected to the body 1606 and configured to be positioned outside a body. In some embodiments, a smooth, optionally planar surface of the annulus is configured to be placed in contact with an outer surface of the skin.

According to some exemplary embodiments, the body 1602 comprises two or more sheets optionally curved as an arc, for example in the form of plates 1610, 1612 and 1614, surrounding the inner lumen 1616. In some embodiments, the curved sheets at least partly overlapping each other, for example to form an enclosed channel. In some embodiments, a surface area of each curved sheet overlaps at least 5%, for example at least 10%, at least 20%, at least 30% or any intermediate, smaller or larger percentage value of a surface area of adjacent curved sheets.

Exemplary View Port

According to some exemplary embodiments, a workspace device, for example a laparoscopic workspace device, comprises at least one view port and/or at least one viewing channel, for example to allow visualization of the inner lumen of the workspace device by an optic sensor, for example a camera. In some embodiments, the optic sensor is connected to an endoscope that can penetrate through the viewing channel into the lumen of the workspace device and/or can be attached to a window in a wall of the workspace device or to a window of a port.

Figure 17A:
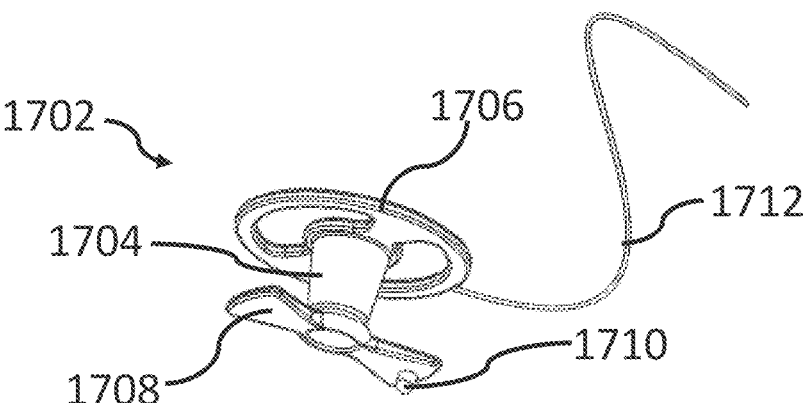
FIG. 17A is a schematic illustration of a port having a visualization opening, according to some exemplary embodiments of the invention.

Reference is now made to FIG. 17A, depicting a view port in a port configured to be positioned within a body opening, according to some exemplary embodiments of the invention.

According to some exemplary embodiments, for example as shown in FIG. 17A, a port 1702 comprises a body 1704, and external annulus, for example an external bolster 1706 configured to be placed in contact with an external surface of the skin, and an inner anchor, for example inner anchor 1708, configured to be placed in contact with an inner surface of a body cavity. In some embodiments, the port 1702 comprises a viewing channel from the external bolster 1706 to the inner anchor 1708. In some embodiments, the viewing channel comprises a view port 1710 in the inner anchor 1708. In some embodiments, the viewing channel and the view port 1710 is configured to receive an endoscope 1712 connected to an optic sensor. In some embodiments, the view port 1710 comprises an opening which is shaped and sized to allow passage of the endoscope 1712 through the viewing channel into a body cavity or into a lumen of a workspace device. Alternatively, the view port comprises a transparent window, in which a distal end of the endoscope 1712 is positioned. In some embodiments, the transparent view port is shaped and positioned to allow a field of view into the body cavity and/or into a lumen of the workspace device.

Figure 17B:
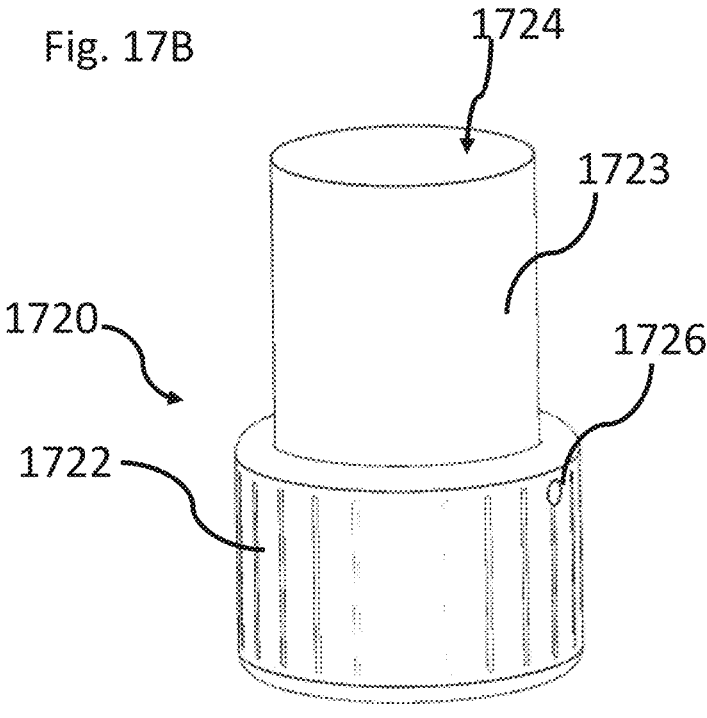
FIGS. 17B and 17C are schematic illustrations of a laparoscopic workspace device having visualization openings and channels, according to some exemplary embodiments of the invention.

Reference is now made to FIG. 17B, depicting a workspace device comprising a side view port in a wall of the workspace device, according to some exemplary embodiments of the invention.

According to some exemplary embodiments, a workspace device 1720 comprises a body, which includes a wall 1722, for example an expandable wall, defining an internal lumen, and a sleeve 1723 connected to the wall 1722 and defining a channel between the internal lumen and a proximal opening 1724. In some embodiments, the sleeve 1723 defines a channel between an external surface of the skin and the internal lumen of the workspace device 1720, when the wall is expanded within a body cavity.

According to some exemplary embodiments, the wall 1722 comprises an opening 1726, for example a side opening. In some embodiments, the opening 1726 is shaped and sized to receive a visualization device, for example a laparoscope. In some embodiments, the opening 1726 is an opening of a visualization channel crossing the wall 1722 into the internal lumen. Optionally, the opening 1726 allows penetration of the visualization device into the internal lumen of the workspace device. In some embodiments, the channel extends at least 1 cm, for example at least 2 cm, for example at least 3 cm, at least 6 cm into the internal lumen of the workspace device. In some embodiments, an end of the visualization channel within the internal lumen is closed, for example to prevent passage of material from the internal lumen through the visualization channel. In some embodiments, at least a portion of the visualization channel is optionally transparent. In some embodiments, a minimal diameter of the visualization channel is at least 3 mm, for example at least 4 mm, at least 5 mm, at least 7 mm, at least 9 mm or any intermediate, smaller or larger value.

In some embodiments, a workspace device comprises two or more openings, for example side openings in the wall. Optionally, at least part of the wall or an inner layer of the wall is transparent, for example to allow visualization into the internal lumen of the workspace device through the opening 1726.

According to some exemplary embodiments, an opening in the wall, for example opening 1726 is positioned between radial rigidizers.

Figure 17C:
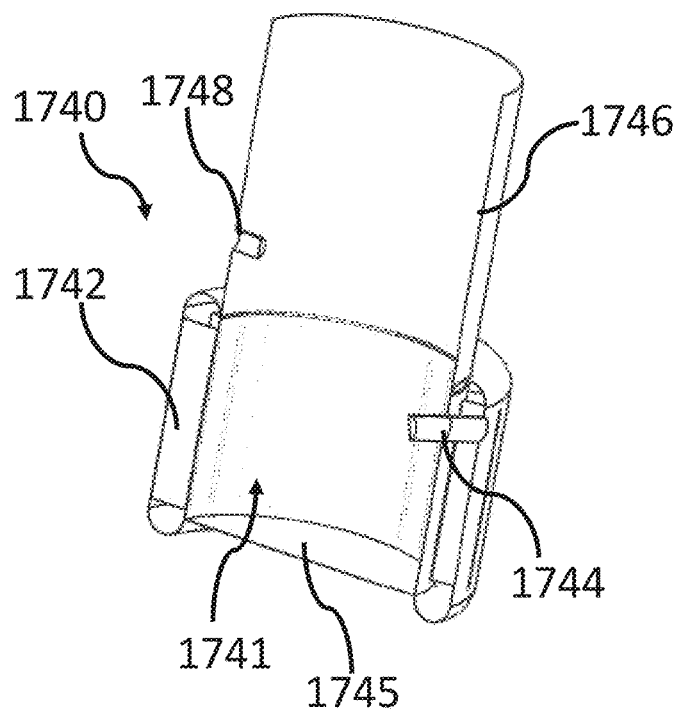

Reference is now made to FIG. 17C, depicting a workspace device with one or more visualization channels, according to some exemplary embodiments of the invention.

According to some exemplary embodiments, workspace device 1740 comprises a wall 1742, for example an expandable wall, and base 1745, defining an internal lumen 1741. Additionally, the workspace device 1740 comprises a sleeve 1746 defining a channel, for example a cylindrical channel connected to the internal lumen 1741. Optionally, the channel is used to place an organ or tissue within the internal lumen 1741. Alternatively or additionally, the channel is a tool channel, which is shaped and sized to receive at least one tool into the internal lumen 1741.

According to some exemplary embodiments, the workspace device 1740 comprises at least one visualization channel, for example visualization channel 1744 crossing at least partly through the wall 1742. In some embodiments, the visualization channel penetrates through the wall 1742 into the internal lumen 1741. Optionally, the visualization channel 1744 terminates within the internal lumen 1741. Alternatively or additionally, the workspace device 1740 comprises at least one visualization channel, for example visualization channel 1748, penetrating through the sleeve 1746. In some embodiments, at least one of the visualization channels 1748 and 1744 are shaped and sized to receive a visualization tool, for example an endoscope or an endoscope end. In some embodiments, the visualization channels 1748 and 1744 are configured to allow visualization of the internal lumen 1741 from the body cavity in which the workspace device, for example workspace device 1740 is deployed.

Exemplary Port with an Expandable End

According to some exemplary embodiments, a port is shaped and sized to penetrate through an incision in the body wall into a body cavity, for example to generate a flow path, between the external surface of the body wall and the body cavity. In some embodiments, during the insertion of the port through the body wall, at least a portion of the port, for example a distal end of the port is collapsed to form a narrow penetrating end of the port. In some embodiments, once the port distal end is within the body cavity, the distal end expands to anchor the port within the body cavity. Reference is now made to FIGS. 17D to 171, depicting a body port with an expandable distal end, according to some exemplary embodiments of the invention.

According to some exemplary embodiments, a port 1701 comprises a tubular body 1703 having a distal end 1705 configured to penetrate into a body cavity, and a proximal end 1707 shaped and sized to be positioned outside the body. In some embodiments, the tubular body 1703 defines an inner lumen 1709 having at least one distal opening at the distal end 1705 and at least one proximal opening at the proximal end 1707.

According to some exemplary embodiments, the port 1701 comprises an external bolster 1711 shaped and sized to anchor the proximal end 1707 of the port body 1703 outside a body of a subject. Optionally, the external bolster 1711 anchors the port to the outer surface of the body. In some embodiments, a minimal width of the external bolster is larger than a maximal with of an incision formed in the body wall of the subject and/or the maximal width of the port tubular body 1703. In some embodiments, a width 1713 of the external bolster 1711 is in a range between 5 cm and 20 cm, for example 5-15 cm, 10-20 cm or any intermediate, smaller or larger range of values. In some embodiments, a surface of the external bolster 1711 is configured to contact the skin at the outer surface of the body. In some embodiments, the skin contacting surface of the external bolster 1711 is flat, for example to prevent damage to the skin when the external bolster 1711 is in contact with the skin surface.

According to some exemplary embodiments, the external bolster 1711 is shaped as a rim. In some embodiments, the external bolster comprises a round or a semi-round plate, surrounding the proximal opening of the tubular body. In some embodiments, the external bolster 1711 is coupled or is integrated with the port body 1703 at the proximal end 1707 of the port body 1703.

According to some exemplary embodiments, the port 1701 comprises an internal bolster 1713 shaped and sized to anchor the distal end 1705 of the port body 1703 within a body cavity of a subject. In some embodiments, the internal bolster 1715 is coupled or is integrated with the port body 1703 at the distal end 1707 of the port body 1703, or at a portion of the body 1703 located within the body cavity of the subject.

Figures 17G, 17H, 17I:
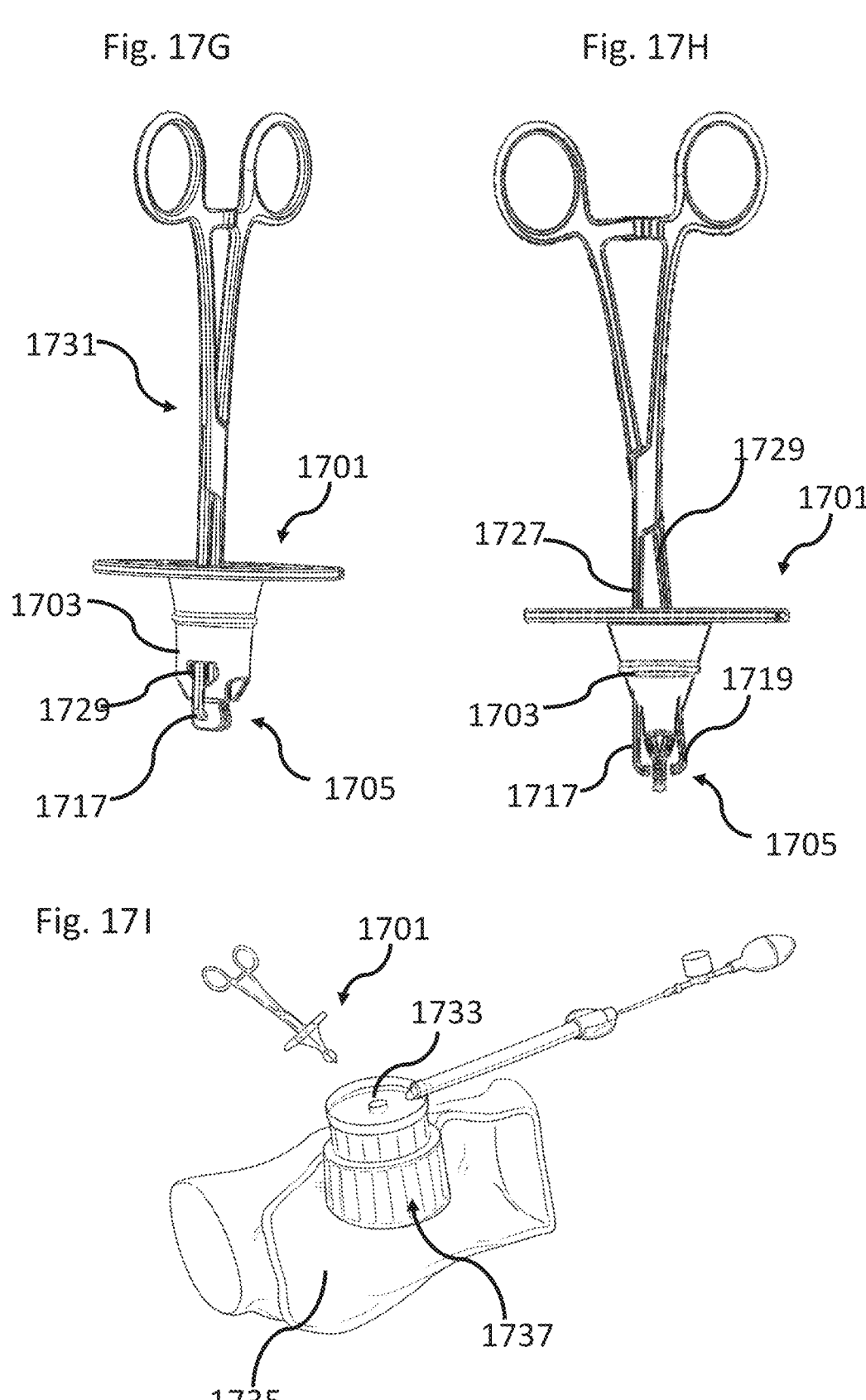
FIGS. 17G-17H are schematic illustrations showing interaction between the port having an expandable distal end and a clamp used to collapse the distal end of the port, according to some exemplary embodiments of the invention.
FIG. 17I is a schematic illustration showing the use of the port and the clamp when inserting the port through an incision in the body wall into a laparoscopic workspace device positioned within a body cavity, according to some exemplary embodiments of the invention.

According to some exemplary embodiments, the internal bolster 1715 is an expandable bolster, configured to move between a collapsed state, for example as shown in FIGS. 17F-17H and an expanded state, for example as shown in FIGS. 17D and 17E. In some embodiments, the internal bolster 1715 is expanded in a relaxed state. Optionally, at least a portion of the internal bolster is configured to move between a collapsed and an expanded state. In some embodiments, the internal bolster 1715 or the at least one expandable portion of the internal bolster 1715 is elastic. Optionally the internal bolster 1715 or the at least one expandable portion of the internal bolster 1715 is made from a flexible and/or elastic material.

According to some exemplary embodiments, the internal bolster 1715 comprises at least two wings, for example wings 1717 and 1719. In some embodiments, the wings are positioned are distributed on a circumference of the port body 1703 at the distal end 1705. In some embodiments, the wings are configured to move between a collapsed state and an expanded state. In some embodiments, the wings are elastic, and expand in a relaxed state.

According to some exemplary embodiments, in a collapsed state, for example as shown in FIG. 17F, the wings 1717 and 1719 face each other and are substantially axially aligned along a long axis 1721 of the port 1701. In some embodiments, in an expanded, optionally relaxed, state, the wings 1717 and 1719 extend laterally from the port body 1703.

In some embodiments, the at least two wings 1717 and 1719 are located at opposite sides of the port body 1703. In some embodiments, the port body comprises at least two slot cuts, for example slot cut 1723, on opposite sides of the tubular body distal end 1705, each slot cut is positioned between the wings 1717 and 1719. In some embodiments, the slot cuts define a bending axis 1725 passing in the middle of each slot cut, that allows, for example as shown in FIG. 17F, easy bending of the distal end 1705 placing the internal bolster in a collapsed state such that the two wings 1717 and 1719 face each other.

According to some exemplary embodiments, in a collapsed state a cross-section of the distal end 1705 is narrower than a cross-section of the proximal end 1707, allowing easier penetration of the distal end 1705 through the incision in the body wall into the body cavity. Optionally, for example as shown in FIGS. 17G and 17H, in a collapsed state of the internal bolster, the port body 1703 forms a structure, optionally a conical structure, converging at the distal end.

According to some exemplary embodiments, the port body 1703 comprises at least two side openings located in the port body wall proximally to the distal end 1705, for example openings 1727 and 1729 shown in FIG. 17E. Optionally, each side opening is positioned between a finger of the at least two fingers 1717 and 1719 and the proximal end 1707. In some embodiments, each side opening is shaped and sized to receive an end of a clamp member, for example an end of a scissors clamp member introduced via the inner lumen 1709 and through a side opening. Optionally each opening of openings 1727 and 1729 is shaped as a slot.

According to some exemplary embodiments, for example as shown in FIGS. 17G and 17H, each elongated member for example members 1727 and 1729 of a clamp 1731, is pushed via an inner lumen of the port 1701 through a side opening, for example side opening 1729, to press the wings 1717 and 1719 into a collapsed state. In some embodiments, the clamp 1731, for example a scissors clamp, is used for example as shown in FIG. 171 during the introduction of the body port 1701 through a body opening 1733 into a body cavity 1735 or into an inner lumen of a laparoscopic workspace device 1737.

According to some exemplary embodiments, for example as shown in FIG. 17D, an external bolster 1711 comprises one or more openings, or at least two openings, for example openings 1757 and 1759, shaped and sized to receive two different fingers, for holding and manipulating the port 17-1 with a single hand. In some embodiments, the openings 1757 and 1759 cross through the external bolster 1711. Alternatively or additionally, the openings, for example openings 1757 and 1759 allow, for example to reduce a contact area between the external bolster and the skin.

According to some exemplary embodiments, an overall length of the tubular body 1703 is in a range between 20 mm-80 mm, for example 20 mm-50 mm, 30 mm-70 mm, 40 mm-80 mm, or any intermediate, smaller or larger range of values. In some embodiments, an inner diameter of the tubular body is in a range between 20 mm-80 mm, for example 20 mm-50 mm, 30 mm-70 mm, 40 mm-80 mm, or any intermediate, smaller or larger range of values.

Exemplary Cutting Guide

According to some exemplary embodiments, during a surgery. For example a laparoscopic surgery, a surgeon perform an incision in the skin and through a body wall, in order to form a body opening to allow access into a body cavity, for example an abdominal cavity in a subject. In some embodiments, the incision is performed in order to allow introduction of surgical tools, for example a laparoscopic tissue containment device into the body cavity through the formed body opening. In some embodiments, a length of the incision is determined according to a maximal diameter of a port, for example a body of a port, that will be placed within the body opening formed by the incision. Reference is now made to FIGS. 17J-17M depicting a port having a cutting guide, according to some exemplary embodiments of the invention.

According to some exemplary embodiments, port 1701, also shown in FIGS. 17D-171, comprises a cutting guide, for example cutting guide 1751. In some embodiments, a cutting guide length provides an indication to a length of an incision that needs to be performed in order to introduce a specific port through the incision and the body wall. Optionally, the cutting guide provides an indication to a length of the incision. In some embodiments, the cutting guide is used to guide a cutting edge of a blade, for example a scalpel along a desired shape and/or length of a cut through the body wall. In some embodiments, a port comprises a cutting guide that is shaped and/or sized according to a shape and/or size of an incision that needs to performed in the body wall in order to introduce the specific port.

According to some exemplary embodiments, the cutting guide of a port comprises a slot having a size and/or shape of a desired incision, for example a surgical incision, that needs to be performed in a body wall. Optionally, the slot is placed at a selected cut location on the skin, and the blade travels within the slot according to the slot length and/or curvature to form the desired incision in the body wall.

Alternatively, in some embodiments, the cutting guide is an edge of the port body or an edge of the internal or external bolsters, that has a length or a contour that matches a desired incision length or shape. In some embodiments, for example as shown in FIGS. 17J-17M, a cutting guide 1751 of a port 1701 is a linear straight edge of the external bolster 1711 that has a length that matches a length of a desired incision in the body wall. In some embodiments, for example as shown in FIGS. 17L and 17M, a length of 1753 of the cutting guide 1751, is similar to an outer diameter 1755 of the port body 1703.

Exemplary Workspace Device Wall with a Tool Insertion Channel

According to some exemplary embodiments, a tool insertion channel of a workspace device is connected to a side opening in a wall of the workspace device. In some embodiments, the tool insertion channel bridges between an external surface of a skin and an internal lumen defined by the wall.

According to some exemplary embodiments, a wall of a workspace device comprises at least one side opening, for example 2, 3, 4 or any larger number of side openings connected to a channel that bridges a passage between the external surface of the skin and an internal lumen of the workspace device.

Reference is now made to FIGS. 18A-18D, depicting a workspace device wall with a side opening, for example for tool insertion, according to some exemplary embodiments of the invention.

According to some exemplary embodiments, a workspace device, for example workspace device 1802 comprises an expandable wall 1804. In some embodiments, the expandable wall comprises one or more, for example 2, 3, 4 or any larger number of expandable segments. In some embodiments, the expandable wall and/or the one or more expandable segments, for example expandable segments 1808 and 1809, are configured to expand when inflated. In some embodiments, when expanded the expandable wall 1804 defines an internal lumen 1806. In some embodiments, the expandable wall 1804 comprises a plurality of radial rigidizers, positioned or formed, near and/or within the expandable segments. Alternatively or additionally, the radial rigidizers are positioned between adjacent expandable segments, for example between expandable segments 1808 and 1809. Optionally, the radial rigidizers are integrated, and define at least some the expandable segments. In some embodiments, the expandable segments, for example expandable segments 1808 and 1809 are inwardly extending expandable segments facing the internal lumen 1806.

According to some exemplary embodiments, device 1802, comprising wall 1804, is configured to expand to an expanded state within a body cavity. In some embodiments, expansion of the wall 1804, for example laterally expansion of the device, defines a workspace axis, for example workspace axis 1840. In some embodiments, the workspace axis 1840 is positioned at an angle 1842 of at least 2 degrees, for example at least 20 degrees, at least 45 degrees, at least 80 degrees, or any intermediate, smaller or larger value relative to a proximal distal axis 1844 between a body opening and an internal lumen 1806 of the device 1802. In some embodiments, the angle 1822 is in a range of 2 degrees-180 degrees, for example 10 degrees-30 degrees, 30 degrees-50 degrees, 45 degrees-80 degrees, 45 degrees-100 degrees, or any intermediate, smaller or larger range of values.

According to some exemplary embodiments, a channel 1810, for example a tool insertion channel, is connected to a side opening in the wall 1804. In some embodiments, a proximal portion of the channel comprising opening 1812, for example a proximal portion closer to a wall of the body, is configured to pass through a body opening, positioning the channel opening 1812 outside the body of a subject. In some embodiments, the channel 1810 is formed from a flexible sleeve, optionally elastic. In some embodiments, the sleeve is collapsible, for example to allow passage of the sleeve through a narrow body opening.

According to some exemplary embodiments, for example as shown in FIGS. 18C and 18D, when the workspace device 1802 is deployed within a body cavity 1820, the expandable wall expands and forms the internal lumen 1806. In some embodiments, the wall 1804 comprises a single opening, for example a single side opening connected to the channel 1810. In some embodiments, the channel 1810 defines a passage between the external surface of the skin 1824 and the intern lumen 1820. In some embodiments, the defined passage allows for example insertion of surgical tools 1822, for example a manual or a motorized morcellator into the internal lumen 1820.

Exemplary Wall Formation

According to some exemplary embodiments, a wall of a workspace device is formed, for example by attaching at least two layers of sheet material to each other, for example by welding. In some embodiments, the at least two layers are spaced-apart by a plurality of spacers, for example ribs. In some embodiments, the ribs are attached, for example welded to the at least two layers, for example to define a plurality of expandable segments between the at least two layers.

Figure 19A:
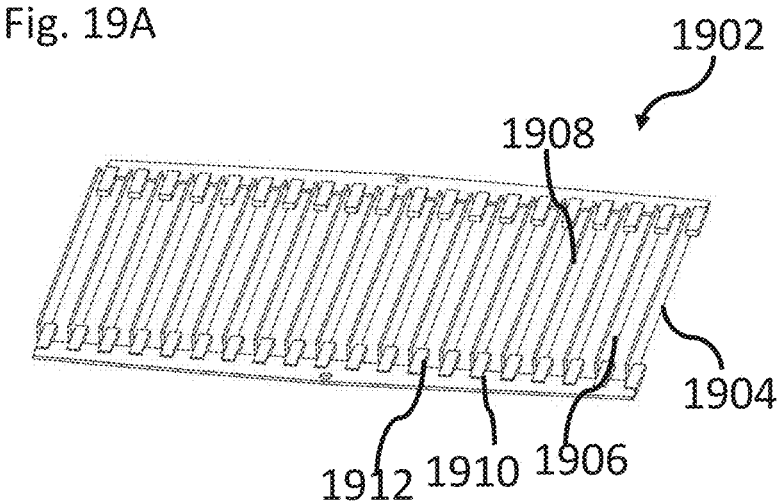
FIGS. 19A and 19B are schematic illustrations of a planar ribs aligner, according to some exemplary embodiments of the invention.
Figure 19B:
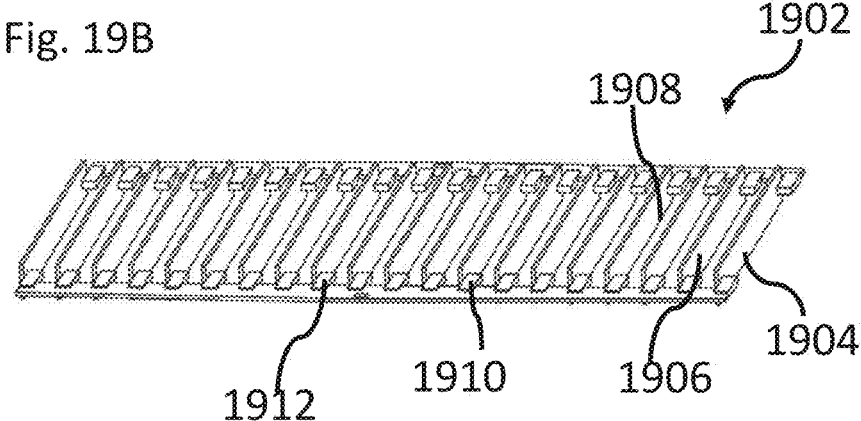

Reference is now made to FIGS. 19A-19B, depicting a ribs aligner, according to some exemplary embodiments of the invention.

According to some exemplary embodiments, a ribs aligner, for example electrode array 1902 comprises a plurality of spaced apart spacers for example spacers 1906 and 1908. In some embodiments, the spacers are configured to reversibly hold a series of ribs, for example radial rigidizers, in a predetermined distance between each other. In some embodiments, the distance between adjacent spacers is fixed. Alternatively, the distance between at least some adjacent spacers is variable. In some embodiments, the spacers are electrodes used during welding, for example RF welding. Alternatively, the spacers are used to determine a position of the ribs during a gluing process.

Figures 20A, 20B, 20C:
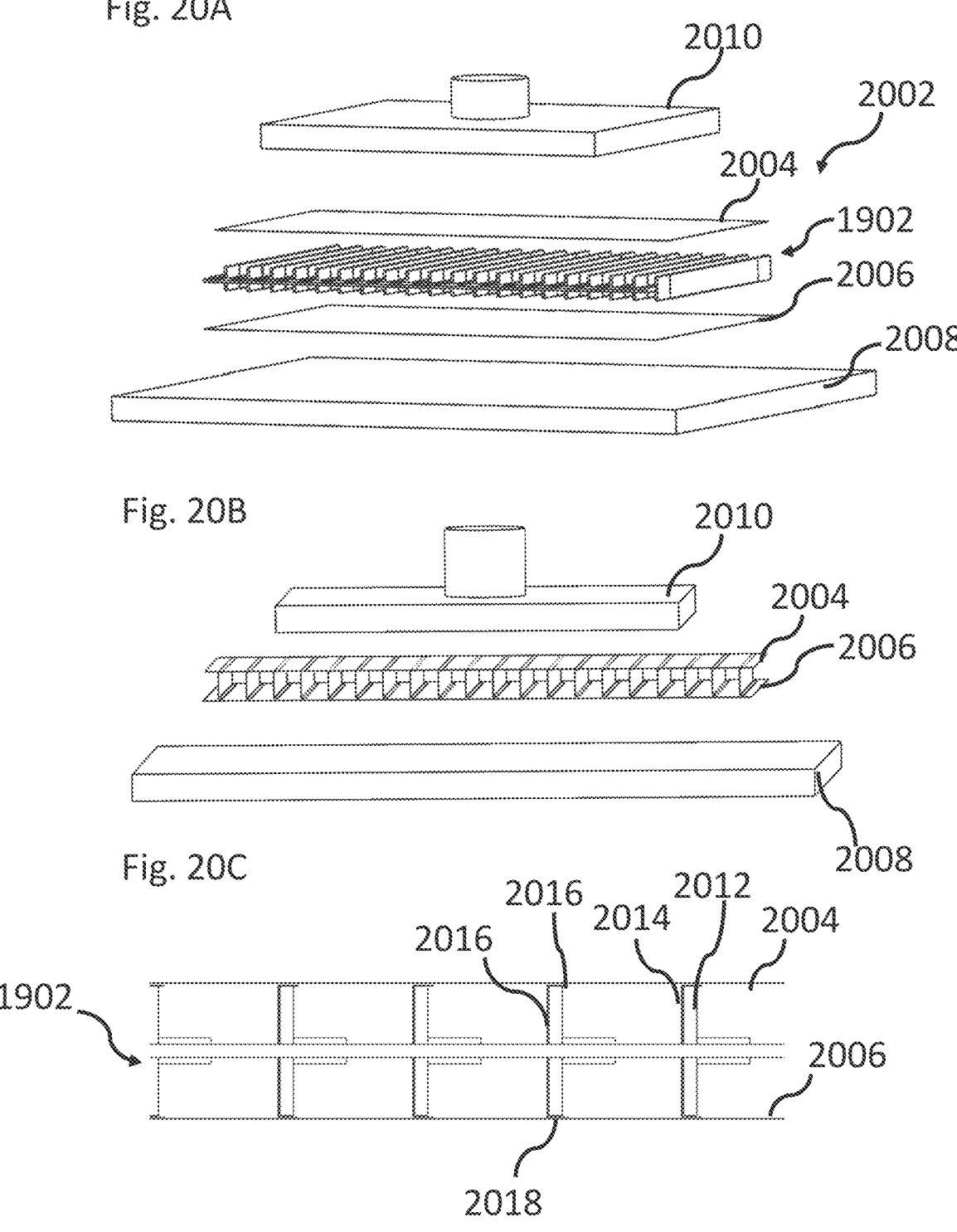
FIGS. 20A-20B are schematic illustrations of a welding assembly, according to some exemplary embodiments of the invention.
FIG. 20C is a schematic illustration of a planar ribs aligner connected to ribs and layers, according to some exemplary embodiments of the invention.

Reference is now made to FIGS. 20A-20C, depicting a welding assembly for attaching at least two layers of sheet material to two opposite ends of ribs, according to some exemplary embodiments of the invention.

According to some exemplary embodiments, a welding assembly, for example welding assembly 2002 comprises an electrode array 1902, where at least some of the spacers of the ribs aligner 1902 are reversibly attached to ribs. In some embodiments, a single spacer is attached to a single rib. Optionally, a single spacer is attached to two ribs, each to an opposite side of the spacer.

Additionally, at least one layer of sheet material, for example layers 2004 and 2006 are positioned on opposite sides of the ribs aligner 1902. In some embodiments, both layers 2004 and 2006 are planar. In some embodiments, both layers 2004 and 2006 have a similar length. In some embodiments, the assembly 2002 comprises a first external plate 2008 and a second external plate 2010, for example rigid plates. In some embodiments, each of the first external plate and the second external plate are positioned to face a surface of a sheet material which is opposite to the ribs aligner 1902.

According to some exemplary embodiments, each of the first external plate and the second external plate, press a layer of sheet material against the ribs aligner 1902, for example against ribs that are reversible fixed to the spacers of the ribs aligner 1902. In some embodiments, during the welding process, an electric field is delivered through electrodes of the ribs aligner to weld ribs held by the ribs aligner to a layer of sheet material pressed against the ribs. In some embodiments, an electric field is delivered through electrodes of the ribs aligner 1902, and at least one electrode attached to each of the first external plate, for example a first welding plate 2008 and a second external plate, for example a second welding plate 2010.

According to some exemplary embodiments, each of the welding plates 2008 and 2010 press a layer of sheet material against the electrode array 1902 during welding. In some embodiments, each of the layers of sheet material, for example layers 2004 and 2006 is welded separately to the ribs in the electrode array 1902, for example by delivering an electric field through the electrode array and one of the welding plates 2008 and 2010. Alternatively, the two layers 2004 and 2006 are welded simultaneously to the ribs in the ribs aligner by simultaneously delivering an electric field through both of the welding plates 2008 and 2010, for example through electrodes attached to the welding plates 2008 and 2010.

According to some exemplary embodiments, for example as shown in FIGS. 20B and 20C, after the delivery of the electric field, the layers 2004 and 2006 are welded to the ribs, for example ribs 2014 and 2016 of the ribs aligner 1902 that are reversibly connected to spacers, for example spacer 2012. In some embodiments, each rib is connected, for example welded to both layers of sheet material by two opposite welding points 2016 and 2018. In some embodiments, once welding is over, the ribs aligner is detached from the welded ribs and layers.

Figure 20D:
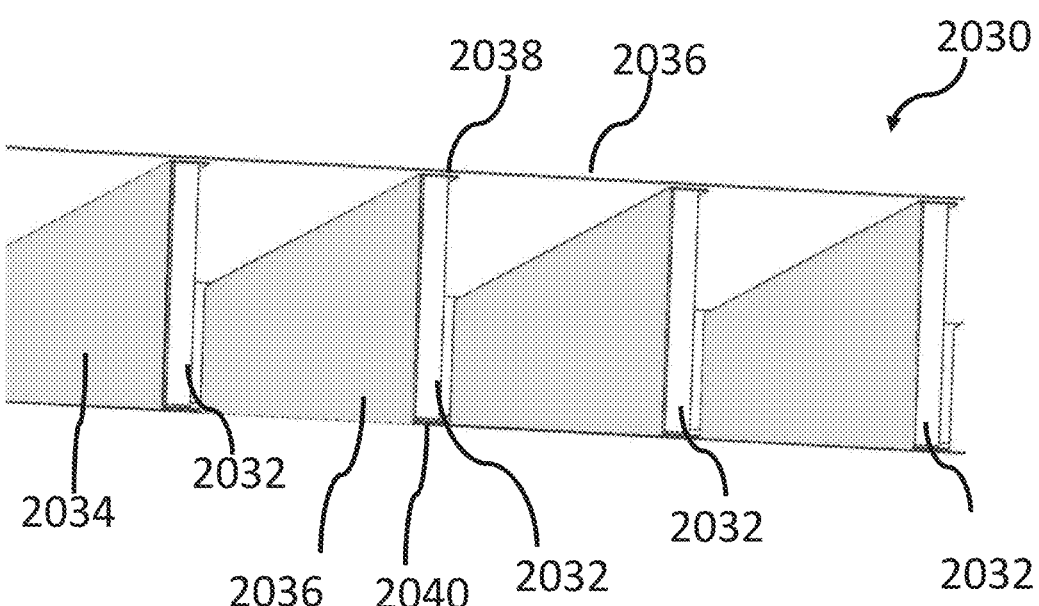
FIG. 20D is a schematic illustration of an electrode array attached to radially extending rigidizers, for example ribs, according to some exemplary embodiments of the invention.

According to some exemplary embodiments, for example as shown in FIG. 20D, an electrode array 2030 comprises a plurality of electrodes 2032. In some embodiments, each of the electrodes 2032 holds and fixes a position of a different rib, for example ribs 2034 and 2036, during a welding process. In some embodiments, each rib is bent at an end of an electrode, for example ends 2038 to face a different layer during the welding process.

Figures 21A, 21B:
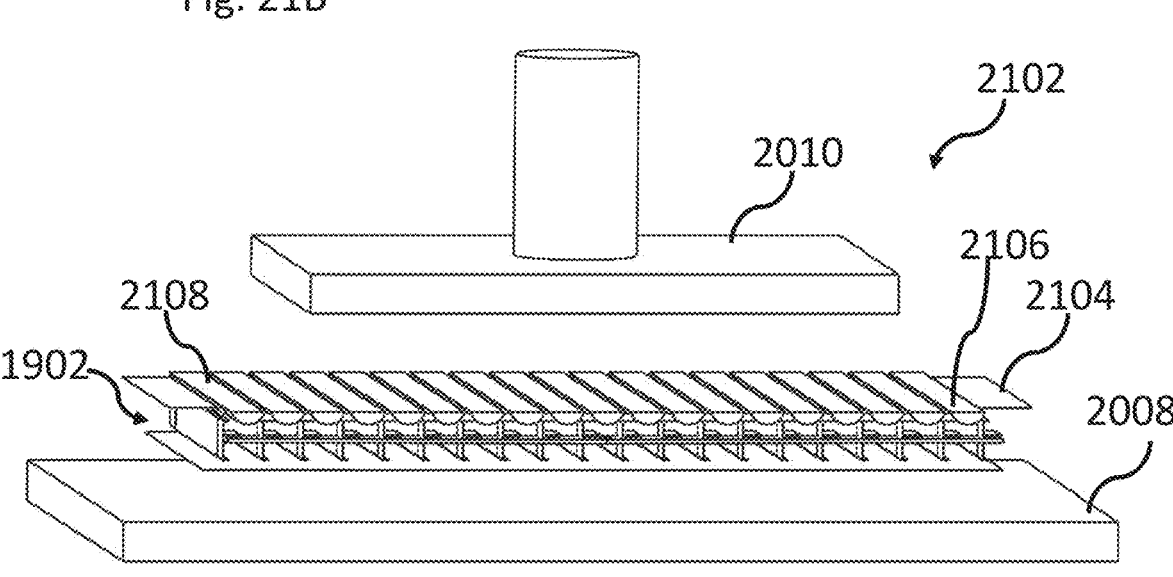
FIGS. 21A and 21B are schematic illustration of a welding assembly including a layer shaper, according to some exemplary embodiments of the invention

According to some exemplary embodiments, for example as shown in FIGS. 21A and 21B, at least one of the layers of sheet material is preshaped during the welding to the ribs. In some embodiments, in an unfolded state, the preshaped layer has a larger length than the planar layer. Optionally, at least one layer is preshaped, while a different layer is planar. In some embodiments, layer 2104 is preshaped into a wavy or curved shape, prior to the welding. In some embodiments, for example as shown in FIG. 21B, at least one shaper, or a plurality of shapers for example shapers 2106 and 2108 are pressed and held against layer 2104, while attaching the layer 2104 to the ribs aligner 1902 during the welding process. In some embodiments, once welding is completed the plurality of shapers are disconnected from the preshaped layer.

Reference is now made to FIGS. 22A-22D, depicting a rotational welding assembly, according to some exemplary embodiments of the invention.

According to some exemplary embodiments, a welding assembly, for example welding assembly 2202 comprises a rotating shaft 2203, and an electrode, for example a cylindrical electrode 2204 connected to the rotating shaft 2203. In some embodiments, the cylindrical electrode 2204 is configured to rotate and turn with the rotating shaft 2203, for example in synchronization with the rotating shaft. In some embodiments, at least one inner cylindrical layer of sheet material, for example layer 2208 is attached to a surface of the cylindrical electrode 2204. In some embodiments, a first inner surface of the inner layer 2208 is attached to the cylindrical electrode 220. In some embodiments, the inner layer 2208 is shaped as a cylinder.

According to some exemplary embodiments, two or more ribs are positioned around a circumference of the inner layer 2208, contacting a second outer surface of the inner layer 2208. In some embodiments, the two or more ribs are disposed between the first inner layer and at least one cylindrical outer layer 2212.

According to some exemplary embodiments, the assembly 2202 comprises at least one additional electrode, for example electrode 2206, configured to press the at least one outer cylindrical layer 2212 against the ribs 2210 and the at least one inner layer 2208. In some embodiments, during welding, an electric field is delivered between the electrode 2206 and the cylindrical electrode 2204, for example when the electrode 2206 presses the at least one outer layer 2212 towards the ribs 2210 and the inner cylindrical layer 2208.

According to some exemplary embodiments, the cylindrical electrode 2204 turns sequentially, optionally to position a different rib in front of the electrode 2206. In some embodiments, when the rotation of the cylindrical electrode 2204 stops, the electrode 2206 is pushed against the outer cylindrical layer while delivering an electric field, for example to weld the rib to the outer cylindrical layer and to the inner cylindrical layer.

Figure 22A:
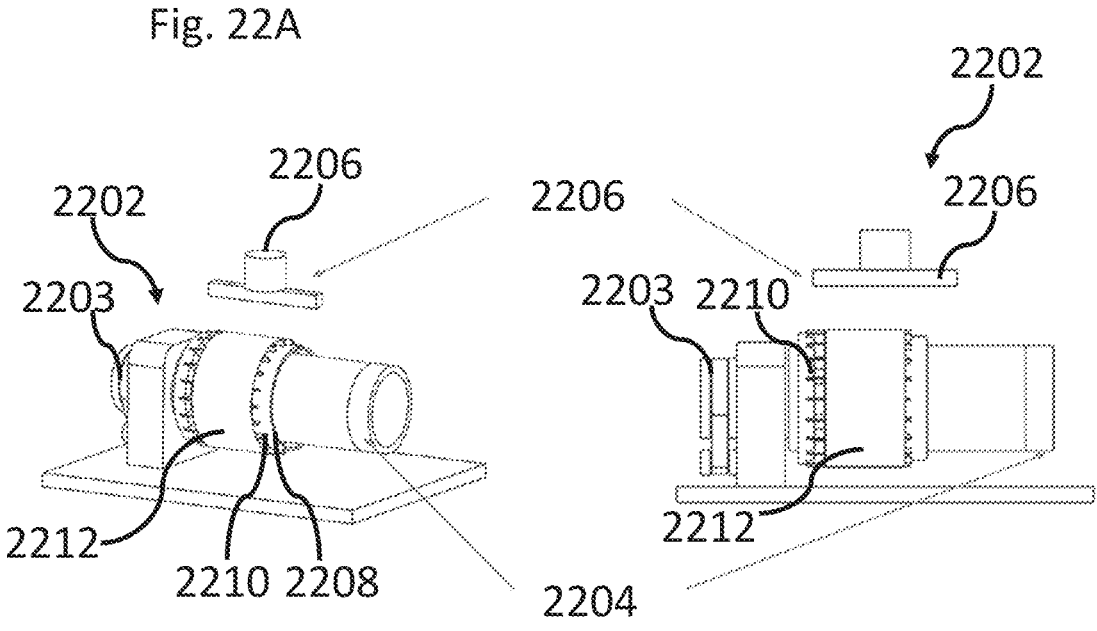
FIGS. 22A and 22B are schematic illustrations of a rotating welding assembly, according to some exemplary embodiments of the invention.
Figure 22B:
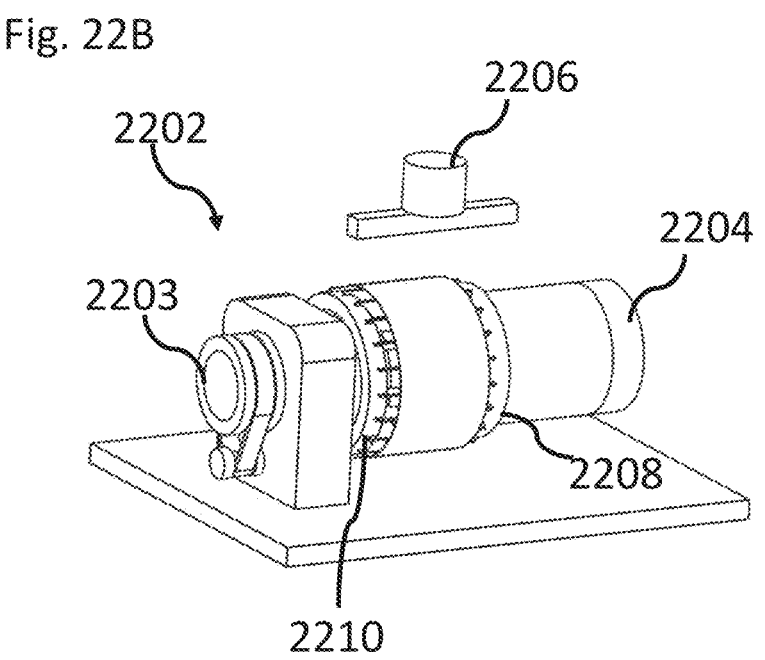
Figure 22C:
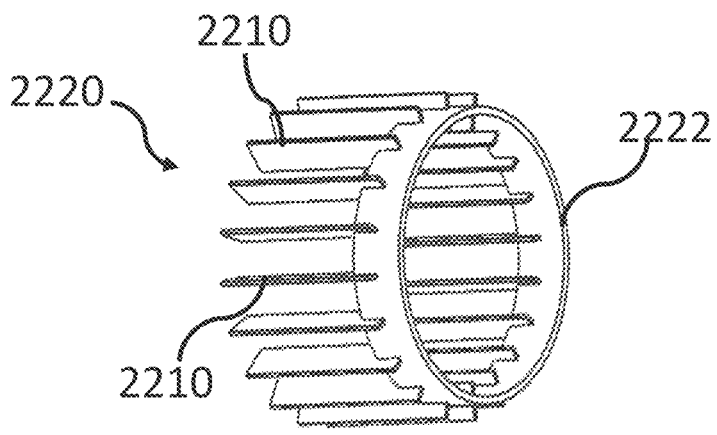
FIG. 22C is a schematic illustration of a round ribs aligner, according to some exemplary embodiments of the invention.
Figure 22D:
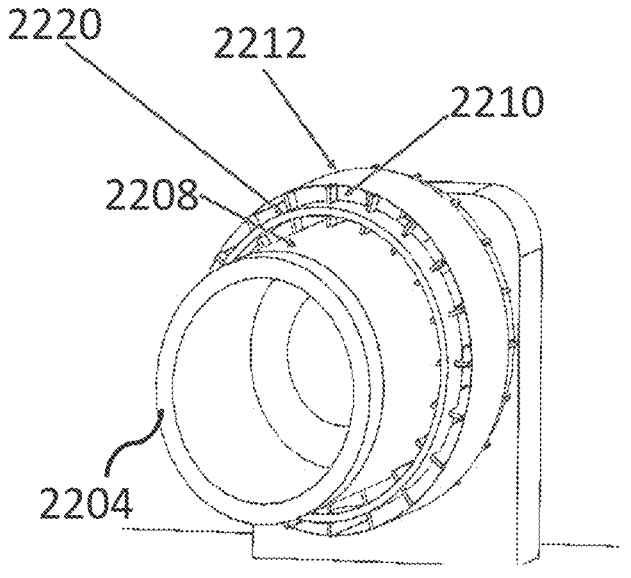
FIG. 22D is a schematic illustration of the round ribs aligner of FIG. 22C in a coupled to a rotating welding assembly, according to some exemplary embodiments of the invention.

Reference is now made to FIGS. 22C and 22D, depicting a round electrode array, according to some exemplary embodiments of the invention.

According to some exemplary embodiments, a round electrode array, 2220 comprises a rim 2222 which is configured to hold a plurality of electrodes 2210. In some embodiments, during the welding process ribs are attached to the electrodes 2210. Optionally, the rim 2222 comprises a plurality of slots arranged on a circumference of the rim 2222. In some embodiments, each of the slots is shaped and sized to receive a single electrode. In some embodiments, the slots are formed at predetermined distances on the rim 2222 circumference, for example according to a desired distance between the ribs.

According to some exemplary embodiments, for example as shown in FIG. 22D, the round electrode array 2220 is positioned between the inner cylindrical layer 2208 attached to the cylindrical electrode 2204, and the outer cylindrical layer 2212. In some embodiments, when welding of the two layers to the ribs is completed, the rim 2222 of the round ribs aligner is removed.

Exemplary Laparoscopic Workspace Device Introducer

According to some exemplary embodiments, the laparoscopic workspace device, for example devices 200, 402 and 420 shown in FIGS. 2A, 2B, and 4A-4D, are introduced into a body cavity using an introducing device. In some embodiments, the workspace device is introduced into the body cavity, for example into an abdominal cavity via an opening in the body formed during a surgical procedure, for example a laparoscopic surgical procedure or through a natural orifice such as a birth canal.

According to some exemplary embodiments, after forming an incision through the skin and the body wall, a distal end of the introducer penetrates through the incision into the body cavity. In some embodiments, the introducer keeps the workspace device in a collapsed, folded state, when passing within the introducer into the body cavity. In some embodiments, once the workspace device is within the body cavity, the introducer expands an opening of the workspace device, for example to allow insertion of tissue or organs through the workspace device opening into an inner lumen of the workspace device. In some embodiments, the introducer is operationally coupled to a fluid source, and controls the inflation and/or a deflation of the expandable wall of the workspace device.

Figures 23A, 23B, 23C:
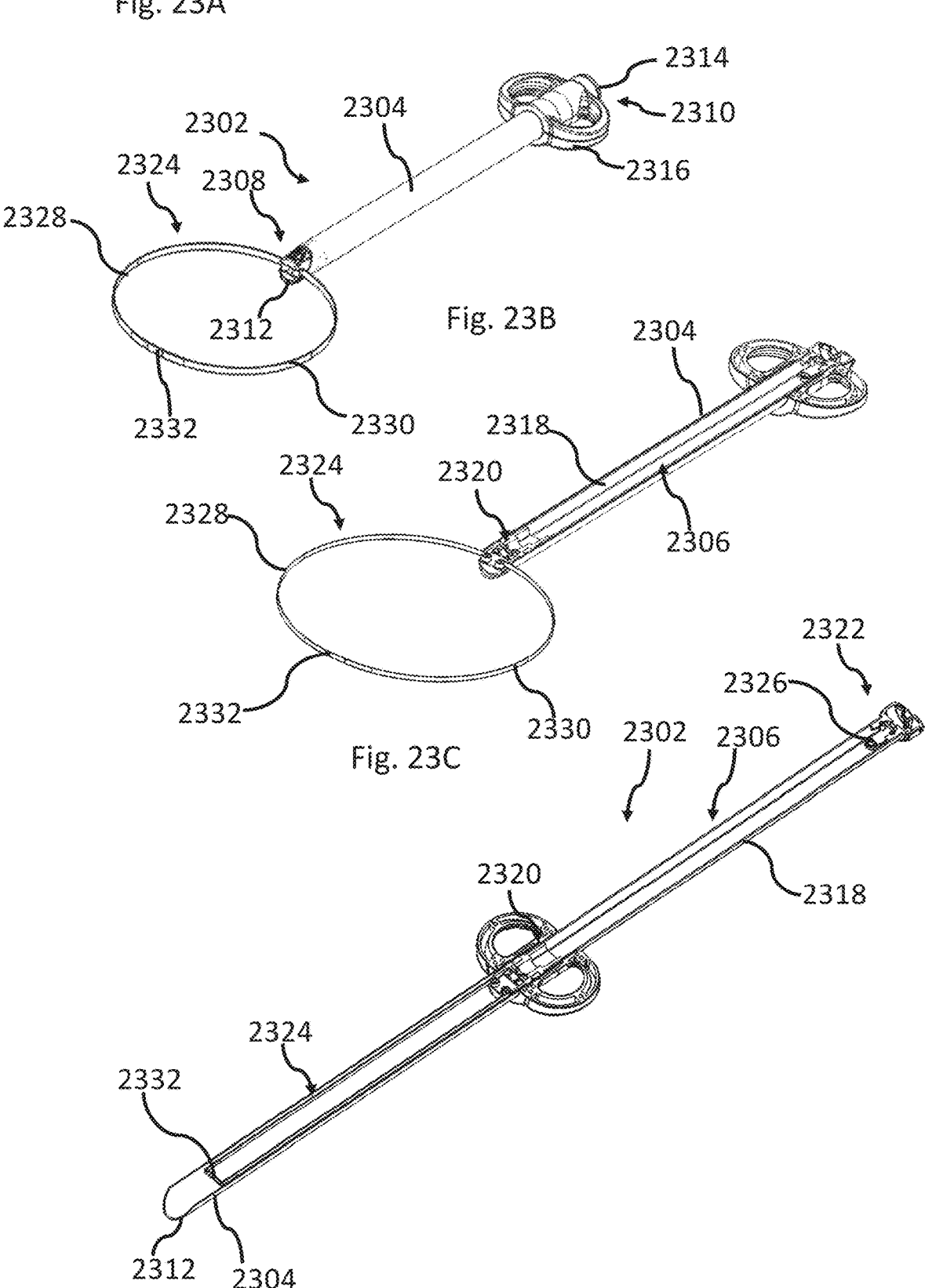
FIGS. 23A-23E are schematic illustrations of an introducer of a workspace device, according to some exemplary embodiments of the invention.

Reference is now made to FIGS. 23A-23C depicting an introducer of a laparoscopic workspace device, according to some exemplary embodiments of the invention.

According to some exemplary embodiments, an introducer, for example introducer 2302 comprises an external tubular body 2304 and an internal member 2306 configured to slide within the external tubular body 2304. In some embodiments, the external tubular body 2304 is a cylindrical body. In some embodiments, the external tubular body 2304 is an elongated body having a distal end 2308 shaped and sized to penetrate through a body opening, for example into a body cavity, and proximal end 2310. In some embodiments, penetration of the external tubular body 2304 into the body cavity forms a channel between the body cavity and the outer surface of the skin. In some embodiments, a distal opening 2312 of the channel is located at the distal end 2308 and a proximal opening 2314 of the channel is located at the proximal end 2310. In some embodiments, an inner lumen of the external tubular body 2304 defines the channel.

According to some exemplary embodiments, the introducer 2302 comprises a gripping member 2316, for example a handle. In some embodiments, the gripping member 2316 is coupled to the external tubular body 2304, for example between the distal end 2310 and the proximal end 2308. In some embodiments, the gripping member 2316 is coupled to the external tubular body 2304 at the distal end 2310 or at a distance smaller than 35 cm, for example smaller than 30 cm, smaller than 25 cm, smaller than 20 cm or any intermediate, smaller or larger distance from the distal end 2310.

According to some exemplary embodiments, the internal member 2306 comprises an elongated body 2318, optionally a tubular body, having a distal end 2320 and a proximal end 2322. In some embodiments, the internal member comprises an expandable workspace device holder 2324 coupled to the distal end 2320 of the internal member elongated body 2318. In some embodiments, the internal member 2306 comprises at least one stopper 2326 at the proximal end 2322, for limiting the extension length of the internal member 2306 out from the distal opening 2312. Optionally, the at least one stopper 2326 is used as a fastener or comprises a fastener, for example a latch, for fastening the internal member 2306 proximal end 2322 to the external tubular body 2304, for example to a proximal end 2310 of the external tubular body 2304.

Figures 23D, 23E:
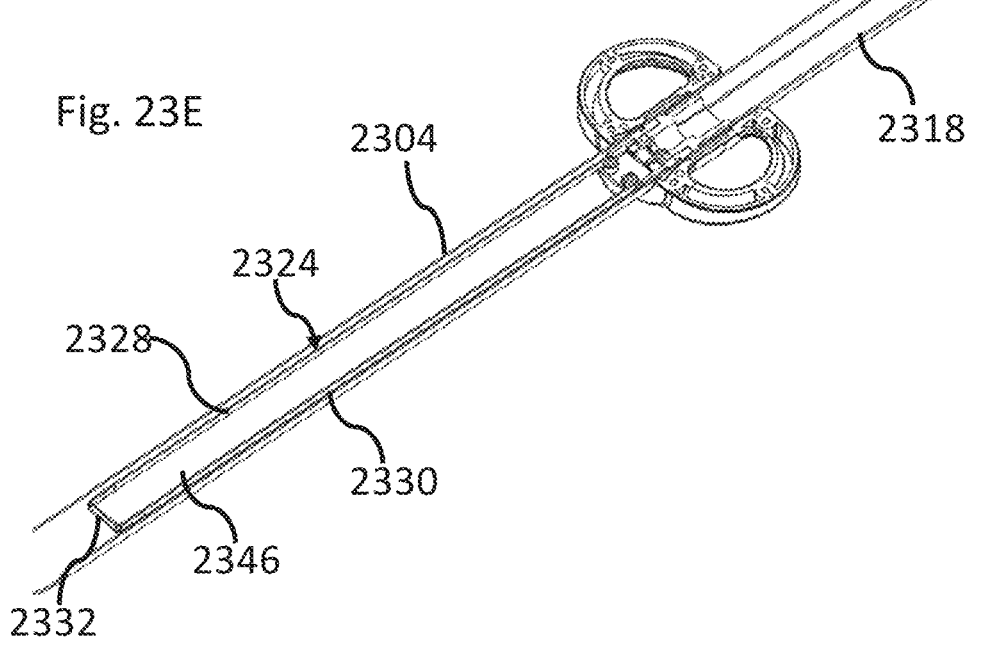

According to some exemplary embodiments, for example as shown in FIGS. 23D and 23E, the holder 2324 comprises at least two elongated elastic members, 2328 and 2330. In some embodiments, the at least two elongated elastic members comprises an elastic strip, for example an elastic metal strip. Alternatively, the at least two elongated elastic members comprise elastic wires and/or elastic cables.

According to some exemplary embodiments, a distal end of each of the at least two elastic members 2328 and 2330 is coupled to at least one spacer 2332, for example a rigid spacer. In some embodiments, the spacer comprises a rigid metal strip, a rigid plastic strip, a rigid wire, or a rigid cable. In some embodiments, a length of the rigid member 2332 is smaller than an inner width, for example an inner diameter, of the external tubular body 2304.

According to some exemplary embodiments, each elastic member is optionally coupled to the at least one spacer 2332 by a bending region, for example an elastic region, configured to allow bending of each elastic member, for example members 2328 and 2330, relative to the at least one spacer 2332. In some embodiments, each elastic region comprises an elastic tube, a shrink, for example a plastic shrink. Alternatively, each end of the at least one spacer 2332 comprises an elastic region connectable to an elastic member of the members 2328 and 2330. Optionally, the at least one spacer comprises a plastic tube or a plastic strip, having openings in each end, to allow connection to the elastic members 2328 and 2330.

According to some exemplary embodiments, a proximal end of each of the at least two elastic members is coupled to a distal end 2320 of the internal member body 2318 via at least one connector. In some embodiments, the elastic member 2328 is coupled to the body 2318 by a connector 2334, and elastic member 2330 is coupled to the body 2318 by a connector 2336. In some embodiments, the at least two elastic members are coupled to the body 2318 at two spaced-apart connection regions. Optionally, each connector comprises a pin, and a proximal end of each elastic member comprises an opening, a hole or is curved, for example as a hook, to be placed around the pin. In some embodiments, each connector of the connectors 2334 and 2336 comprises a hinge, for example to allow rotation of a proximal end of each elastic member relative to the distal end 2320 of the internal member body 2318, for example when the holder expands.

Figure 23F:
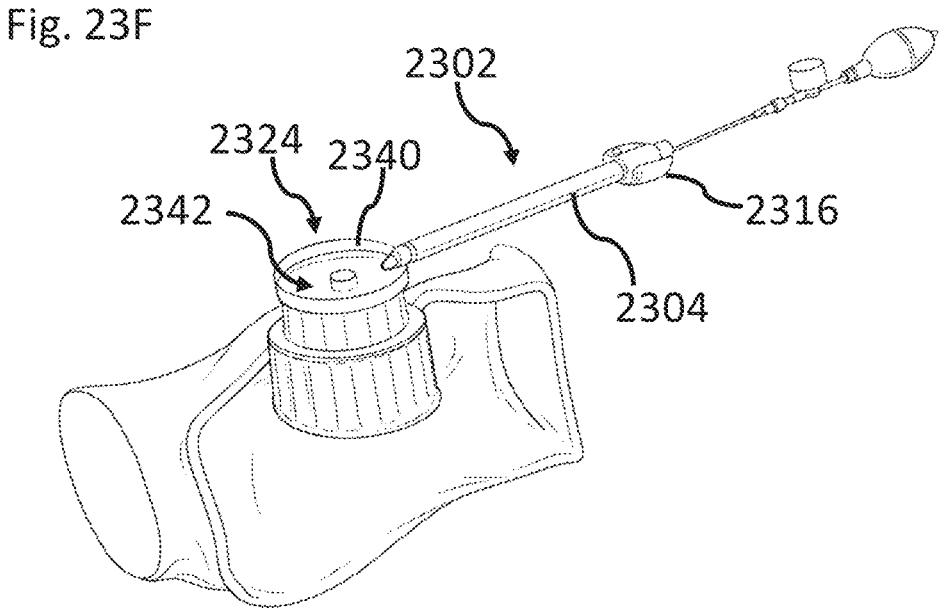
FIG. 23F is a schematic illustration showing an introducer holder surrounding an opening of a workspace device, while the holder is in an expanded state forcing the workspace device to open, according to some exemplary embodiments of the invention.

According to some exemplary embodiments, for example as shown in FIG. 23F the expandable holder 2324 is coupled to a circumference 2340 of a workspace device opening 2342. Optionally, the expandable holder surrounds the opening 2328 of the workspace device. In some embodiments, in a collapsed state, for example as shown in FIG. 23E, the holder 2324 forms a frame 2346, for example by keeping the elastic members 2328 and 2330 spaced-apart, within the inner lumen, for example an inner channel, of the external tubular body 2304. In some embodiments, the workspace device coupled to the holder 2324 is positioned within the frame 2346 between the elastic members, in a collapsed folded state. In some embodiments, the frame formation allows, for example to prevent pressure on the collapsed workspace device by the at least two elastic members that may damage the workspace device during storage or delivery into the body cavity.

According to some exemplary embodiments, the at least one spacer 2332, and/or the spaced-apart connectors are configured to keep the elastic members 2328 and 2330 spaced-apart, for example at a desired distance between each other, when the holder 2324 is collapsed within the external tubular body 2304.

According to some exemplary embodiments, for example as shown in FIGS. 23D and 23F, in an expanded state, for example when the holder 2324 is in a relaxed state, the elastic members 2328 and 2330 expand and the holders acquires a rim shape, forcing the workspace device opening 2328 to open, as shown in FIG. 23F.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A workspace device having a body which is collapsible to a collapsed state to fit through a laparoscopic passageway in a body cavity wall, and expandable to an expanded state within a body cavity into which said passageway extends, comprising:
   a workspace body having a workspace wall defining an internal lumen, wherein said workspace wall includes a plurality of vertical expandable segments and at least one radial rigidizer positioned within said wall;
   wherein in said expanded state:
   said workspace device extends defining a workspace axis, and has an opening to said internal volume; and
   said plurality of vertical expandable segments rigidize said workspace body to resist collapse by intra-abdominal forces, and said at least one radial rigidizer positioned within said wall rigidize said workspace body to resists radial forces;
   wherein in said expanded state, two adjacent vertical expandable segments contact each other along an interface region having a length larger than 0.2 cm.

2. A device according to claim 1, wherein said workspace wall comprises at least one inflatable chamber, and wherein said at least one radial rigidizer divides said at least one inflatable chamber into said plurality of vertical expandable segments which are fluidically connected to each other.

3. A device according to claim 2, wherein said at least one radial rigidizer comprises a plurality of radial rigidizers dividing said at least one inflatable chamber into said plurality of vertical expandable segments, and wherein at least some or all of the plurality of radial rigidizers are perforated for fluidcally connecting said plurality of vertical expandable segments.

4. A device according to claim 1, wherein in said expanded state said at least one radial rigidizer is smaller than a length of said workspace wall.

5. A device according to claim 1, wherein said workspace wall comprises at least one inner layer of sheet material forming said inner surface facing in an expanded state the internal lumen of the workspace device, and at least one outer layer of sheet material forming said outer surface of said workspace wall, and wherein said at least one radial rigidizer interconnects said at least one inner layer and said at least one outer layer.

6. A device according to claim 5, wherein said at least one radial rigidizer comprises at least one additional bendable layer of sheet material attached to said inner layer and said outer layer.

7. A device according to claim 5, wherein in an expanded state, said at least one inner layer and said at least one outer layer are smooth.

8. A device according to claim 5, wherein, in an expanded state, said at least one inner layer is smoother than said at least one outer layer, and wherein said vertical expandable segments extend radially outwardly to a distance larger than 1 cm from said internal lumen.

9. A device according to claim 5, wherein, in an expanded state, said at least one outer layer is smoother than said at least one inner layer, and wherein said vertical expandable segments extend radially inwardly into said at least one internal lumen of said workspace device to a distance larger than 1 cm from said at least one outer layer.

10. A device according to claim 5, wherein in an expanded state, a portion of said at least one radial rigidizer interconnecting said at least one inner layer and said at least one outer layer is perpendicular to a tangent of at least one or both of said at least one inner layer and said at least one outer layer.

11. A device according to claim 5, wherein in an expanded state, a portion of said at least one radial rigidizer interconnecting said at least one inner layer and said at least one outer layer is positioned at an angle smaller than 90 degrees relative to a tangent of at least one or both of said at least one inner layer and said at least one outer layer.

12. A device according to claim 5, wherein in an unfolded state, a length of said at least one outer layer is larger than a length of said at least one inner layer.

13. A device according to claim 5, wherein in an unfolded, a length of said at least one outer layer is similar to a length of said at least one inner layer.

14. A device according to claim 1, wherein said at least one radial rigidizer comprises a plurality of radial rigidizers, and wherein a sidewall of at least one vertical expandable segments of said plurality of vertical expandable segments is formed by at least one radial rigidizer of said plurality of radial rigidizers.

15. A device according to claim 1, comprising one or more inflation channels shaped to supply inflation fluid to said workspace device body and to said vertical expandable segments to expand said workspace body to said expanded state.

16. A device according to claim 1, comprising one or more visualization channels in said workspace body penetrating at least 1 cm into said internal lumen through an opening in an outer surface of said body; wherein said one or more visualization channels are sized to receive an end of a visualization tool.

17. A device according to claim 1, wherein in said expanded state said workspace device extends axially from a proximal to a distal direction defining said workspace axis, and wherein said vertical expandable segments are vertical expandable segments oriented along said workspace axis and arranged around a circumference of said internal lumen.

18. A device according to claim 1, wherein said body comprises a distal base coupled to said wall, and a proximal cylindrical sleeve extending from said body and defining a channel to said internal lumen, and wherein in said expanded state, said plurality of vertical expandable segments are positioned between said proximal cylindrical sleeve and said distal base.

19. A device according to claim 1, wherein said workspace wall comprises at least one horizontal expandable segment surrounding said internal lumen, and wherein in said expanded state said at least one horizontal expandable segment is shaped as a ring.

* * * * *